US012678419B2

(12) United States Patent
Fyfe et al.

(10) Patent No.: US 12,678,419 B2
(45) Date of Patent: Jul. 14, 2026

(54) COMPOUNDS

(71) Applicant: Sitryx Therapeutics Limited, Oxford (GB)

(72) Inventors: Matthew Colin Thor Fyfe, Oxford (GB); Barry John Teobald, Oxford (GB)

(73) Assignee: Sitryx Therapeutics Limited, Oxford (GB)

( * ) Notice: Subject to any disclaimer, the term of this patent is extended or adjusted under 35 U.S.C. 154(b) by 565 days.

(21) Appl. No.: 18/034,122

(22) PCT Filed: Oct. 27, 2021

(86) PCT No.: PCT/GB2021/052791

§ 371 (c)(1),
(2) Date: Apr. 27, 2023

(87) PCT Pub. No.: WO2022/090714

PCT Pub. Date: May 5, 2022

(65) Prior Publication Data

US 2023/0381132 A1 Nov. 30, 2023

(30) Foreign Application Priority Data

Oct. 27, 2020 (EP) .................................... 20204136
Feb. 26, 2021 (EP) .................................... 21159744

(51) Int. Cl.

| | |
|---|---|
| ***A61K 31/225*** | (2006.01) |
| ***A61K 45/06*** | (2006.01) |
| ***A61P 37/06*** | (2006.01) |
| ***C07C 67/08*** | (2006.01) |
| ***C07C 69/593*** | (2006.01) |

(52) U.S. Cl.

CPC ............ *A61K 31/225* (2013.01); *A61K 45/06* (2013.01); *A61P 37/06* (2018.01); *C07C 67/08* (2013.01); *C07C 69/593* (2013.01)

(58) Field of Classification Search

None

See application file for complete search history.

(56) References Cited

U.S. PATENT DOCUMENTS

2022/0265595 A1 8/2022 Cooke et al.

FOREIGN PATENT DOCUMENTS

| | | | |
|---|---|---|---|
| EP | 3357924 | A1 | 8/2018 |
| WO | 2019/036509 | A1 | 2/2019 |
| WO | 2020222010 | A1 | 11/2020 |
| WO | 2020222011 | A1 | 11/2020 |
| WO | 2021130492 | A1 | 7/2021 |
| WO | 2022029438 | A1 | 2/2022 |
| WO | 2022038365 | A2 | 2/2022 |
| WO | 2022090714 | A1 | 5/2022 |
| WO | 2022090723 | A1 | 5/2022 |
| WO | 2022090724 | A1 | 5/2022 |

*Primary Examiner* — Juliet C Switzer
*Assistant Examiner* — Dawanna Shar-Day White
(74) *Attorney, Agent, or Firm* — Faegre Drinker Biddle & Reath LLP

(57) ABSTRACT

The invention relates to compounds of formula (I) and to their use in treating or preventing an inflammatory disease or a disease associated with an undesirable immune response:

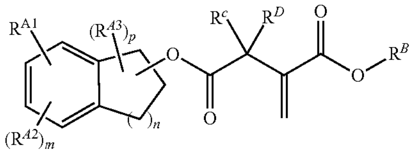

wherein $R^{A1}$, $R^{A2}$, $R^{A3}$, $R^B$, $R^C$, $R^D$, m, n and p are as defined herein.

15 Claims, No Drawings

COMPOUNDS

CROSS-REFERENCE TO RELATED APPLICATIONS

This application is the National Stage of International Application No. PCT/GB2021/052791 filed Oct. 27, 2021, which claims priority to and benefit of European Application Nos. 20204136.4 filed Oct. 27, 2020, and 21159744.8 filed Feb. 26, 2021, each of which is herein incorporated by reference in its entirety.

FIELD OF THE INVENTION

The present invention relates to compounds and their use in treating or preventing inflammatory diseases or diseases associated with an undesirable immune response, and to related compositions, methods and intermediate compounds.

BACKGROUND OF THE INVENTION

Chronic inflammatory diseases such as rheumatoid arthritis, systemic lupus erythematosus (SLE), multiple sclerosis, psoriasis, Crohn's disease, ulcerative colitis, uveitis and chronic obstructive pulmonary disease (COPD) represent a significant burden to society because of life-long debilitating illness, increased mortality and high costs for therapy and care (Straub R. H. and Schradin C., 2016). Non-steroidal anti-inflammatory drugs (NSAIDs) are the most widespread medicines employed for treating inflammatory disorders, but these agents do not prevent the progression of the inflammation and only treat the accompanying symptoms. Glucocorticoids are powerful anti-inflammatory agents, making them emergency treatments for acute inflammatory flares, but given longer term these medicines give rise to a plethora of unwanted side-effects and may also be subject to resistance (Straub R. H. and Cutolo M., 2016). Thus, considerable unmet medical need still exists for the treatment of inflammatory disorders and extensive efforts to discover new medicines to alleviate the burden of these diseases is ongoing (Hanke T. et al., 2016).

Dimethyl fumarate (DMF), a diester of the citric acid cycle (CAC) intermediate fumaric acid, is utilised as an oral therapy for treating psoriasis (Brück J. et al., 2018) and multiple sclerosis (Mills E. A. et al., 2018). Importantly, following oral administration, none of this agent is detected in plasma (Dibbert S. et al., 2013), the only drug-related compounds observed being the hydrolysis product monomethyl fumarate (MMF) and glutathione (GSH) conjugates of both the parent (DMF) and metabolite (MMF). DMF's mechanism of action is complex and controversial. This compound's efficacy has been attributed to a multiplicity of different phenomena involving covalent modification of proteins and the conversion of "prodrug" DMF to MMF. In particular, the following pathways have been highlighted as being of relevance to DMF's anti-inflammatory effects: 1) activation of the anti-oxidant, anti-inflammatory, nuclear factor (erythroid-derived 2)-like 2 (NRF2) pathway as a consequence of reaction of the electrophilic α,β-unsaturated ester moiety with nucleophilic cysteine residues on kelch-like ECH-associated protein 1 (KEAP1) (Brennan M. S. et al., 2015); 2) induction of activating transcription factor 3 (ATF3), leading to suppression of pro-inflammatory cytokines interleukin (IL)-6 and IL-8 (Müller S. et al., 2017); 3) inactivation of the glycolytic enzyme glyceraldehyde 3-phosphate dehydrogenase (GAPDH) through succination of its catalytic cysteine residue with a Michael accepting unsaturated ester (Kornberg M. D. et al., 2018; Angiari S. and O'Neill L. A., 2018); 4) inhibition of nuclear factor-kappaB (NF-κB)-driven cytokine production (Gillard G. O. et al., 2015); 5) preventing the association of PKCθ with the costimulatory receptor CD28 to reduce the production of IL-2 and block T-cell activation (Blewett M. M. et al., 2016); 6) reaction of the electrophilic α,β-unsaturated ester with the nucleophilic thiol group of anti-oxidant GSH, impacting cellular responses to oxidative stress (Lehmann J. C. U. et al., 2007); 7) agonism of the hydroxycarboxylic acid receptor 2 (HCA2) by the MMF generated in vivo through DMF hydrolysis (von Glehn F. et al., 2018); 8) allosteric covalent inhibition of the p90 ribosomal S6 kinases (Andersen J. L. et al., 2018); 9) inhibition of the expression and function of hypoxia-inducible factor-1α (HIF-1α) and its target genes, such as IL-8 (Zhao G. et al., 2014); and 10) inhibition of Toll-like receptor (TLR)-induced M1 and K63 ubiquitin chain formation (McGuire V. A. et al., 2016). In general, with the exception of HCA2 agonism (Tang H. et al., 2008), membrane permeable diester DMF tends to exhibit much more profound biological effects in cells compared to its monoester counterpart MMF. However, the lack of systemic exposure of DMF in vivo has led some researchers to assert that MMF is, in fact, the principal active component following oral DMF administration (Mrowietz U. et al., 2018). As such, it is evident that some of the profound biology exerted by DMF in cells is lost because of hydrolysis in vivo to MMF.

Recently, it has been discovered that, during inflammatory macrophage activation, the CAC becomes anaplerotic and is diverted such that the unsaturated diacid itaconic acid, "itaconate", is generated (Murphy M. P. and O'Neill L. A. J., 2018; O'Neill L. A. J. and Artyomov M. N., 2019; Yu X.-H. et al., 2019). Instead of being hydrated to isocitrate by aconitate hydratase, the CAC intermediate aconitate is decarboxylated by the protein product of immune-responsive gene 1 (IRG1), one of the most highly upregulated genes in macrophages under proinflammatory conditions, subsequently named aconitate decarboxylase 1, to produce itaconic acid (Michelucci A. et al., 2013). This unsaturated diacid is an inhibitor of the bacterial enzyme isocitrate lyase and, as such, it exerts anti-bacterial activity. In addition, itaconic acid has been shown to inhibit the CAC enzyme succinate dehydrogenase (SDH) (Ackermann et al., 1949), leading accordingly to succinate accumulation (Cordes T. et al., 2016). By inhibiting SDH, an enzyme critical for the inflammatory response (E. L. Mills et al., 2016), itaconate ameliorates inflammation in vitro and in vivo during macrophage activation and ischemia-reperfusion injury (Lampropoulou V. et al., 2016).

Like fumaric acid, itaconic acid is an α,β-unsaturated carboxylic acid. As such, it is a Michael acceptor which induces a global electrophilic stress response. In this regard, the itaconic acid diester dimethyl itaconate (DMI), like DMF, produces an anti-inflammatory response, reducing the expression levels of pro-inflammatory cytokines IL-1β, IL-6, IL-12 and IL-18 in lipopolysaccharide (LPS)-stimulated bone marrow-derived macrophages (WO2017/142855A1, incorporated herein by reference). This response appears to be mediated, in part, by NRF2 activation, via alkylation of KEAP1 cysteine residues by the electrophilic α,β-unsaturated ester moiety (Mills E. L. et al., 2018), which enhances the expression of downstream genes with anti-oxidant and anti-inflammatory capacities. Nevertheless, not all of the pronounced immunoregulatory effects engendered by DMI can be attributed to NRF2 activation. In particular, the modulation of IκBζ by DMI is independent of NRF2 and is mediated via upregulation of ATF3, a global negative regulator of immune activation that downregulates various cytokines, such as IL-6 (Bambouskova M. et al., 2018). Moreover, by inhibiting IκBζ protein production, DMI ameliorates IL-17-mediated pathologies, highlighting the therapeutic potential of this regulatory pathway (WO2019/036509A1, incorporated herein by reference). Further highlighting its pharmacologic potential, DMI has recently been reported to 1) demonstrate a protective effect on cerebral ischemia/reperfusion injury, thereby offering potential for the treatment of ischemic stroke (Zhang D. et al., 2019); 2) provide protection from the cardiotoxic effects of doxorubicin (Shan Q. et al., 2019); and 3) protect against lippolysacchride-induced mastitis in mice by activating MAPKs and NRFrf2 while inhibiting NF-κB signaling pathways (Zhao C. et al., 2019). Furthermore, DMI is said to have utility in preventing and treating ulcerative colitis and canceration thereof (CN110731955, Sun Yat-sen University Cancer Center); and has been reported to protect against fungal keratitis by activating the NRF2/HO-1 signalling pathway (Gu L. et al., 2020). Nevertheless, it should be noted that DMI is not metabolised to itaconic acid intracellularly (ElAzzouny M. et al., 2017). Other α,β-unsaturated esters exhibit IL-1β-lowering effects in macrophages by inhibiting the NLRP3 inflammasome (Cocco M. et al., 2017 and 2014), and have been demonstrated to inhibit the TLR4 pathway, leading ultimately to suppression of LPS-induced stimulation of NF-κB, tumour necrosis factor (TNF)-α, IL-1β and nitric oxide release (Zhang S. et al., 2012).

Other itaconic acid derivatives have been demonstrated to elicit anti-inflammatory effects (Bagavant G. et al., 1994). A notable example is 4-octyl itaconic acid (4OI), an itaconate derivative with improved cellular uptake. Since the α,β-unsaturated carboxylic acid is not esterified in 401, this electrophile exhibits low reactivity with biological thiols (Schmidt T. J. et al., 2007), much like the situation encountered with itaconic acid itself. As a result of its low reactivity/electrophilicity, the NRF2-activating effects of 401 are not attenuated by GSH, in contrast to the findings with the much more reactive DMI. In this latter case, the α,β-unsaturated carboxylic acid is esterified and, as a consequence, the IL-6-lowering and NRF2-activating effects of DMI are reversed by the thiols N-acetylcysteine and GSH, respectively. Through the reaction with KEAP1 and the resulting NRF2 activation, as well as GAPDH inhibition (Liao S.-T. et al., 2019), 401 has been demonstrated to produce a wide range of interesting biological effects, including: 1) protection of neuronal cells from hydrogen peroxide (Liu H. et al., 2018); 2) inhibition of proinflammatory cytokine production in peripheral blood mononuclear cells of SLE patients (Tang C. et al., 2018); and 3) protection of human umbilical vein endothelial cells from high glucose (Tang C. et al., 2019); 4) inhibition of osteoclastogenesis by suppressing the E3 ubiquitin ligase Hrd1 and activating NRF2 signaling (Sun X. et al., 2019); 5) induction of repression of STING by NRF2 and type I IFN production in cells from patients with STING-dependent interferonopathies (Olagnier D. et al., 2018); 6) protection against renal fibrosis via inhibiting the TGF-beta/Smad pathway, autophagy and reducing generation of reactive oxygen species (Tian F. et al., 2020); 7) reduction of brain viral burden in mice intracranially injected with Zika virus (Daniels B. P. et al. 2019); and 8) protection against liver ischemia-reperfusion injury (Yi F. et al. 2020). Furthermore, itaconate has been reported to modulate tricarboxylic acid and redox metabolism to mitigate reperfusion injury (Cordes T. et al., 2020). In addition, raised plasma itaconate levels demonstrate a clear correlation with reduction in rheumatoid arthritis disease activity scores following commencement of therapy with conventional disease modifying anti-rheumatic drug (cDMARD) therapy (Daly R. et al. 2019).

Artyomov et al. (WO2017/142855; WO2019/036509) disclose the use of itaconate, malonate or a derivative thereof as an immunomodulatory agent.

In spite of the above findings, there remains a need to identify and develop new itaconate derivatives possessing enhanced properties compared to currently marketed anti-inflammatory agents, such as DMF. The present inventors have now discovered, surprisingly, that certain itaconate diesters with good metabolic stability are highly effective at reducing cytokine release in cells and/or in activating NRF2-driven effects. These properties, amongst others, make them potentially more effective than dimethyl itaconate and/or dimethyl fumarate. Such compounds therefore possess excellent anti-inflammatory properties.

SUMMARY OF THE INVENTION

The present invention provides a compound of formula (I):

(I)

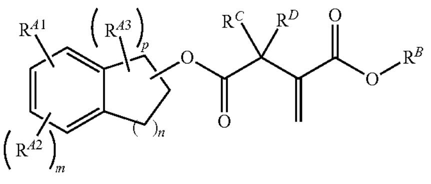

wherein:

$R^{A1}$ is selected from the group consisting of H, halo, $C_{1-4}$alkyl, $C_{1-4}$haloalkyl, $C_{1-4}$alkoxy, $C_{1-4}$haloalkoxy, —$SC_{1-4}$alkyl, —$SC_{1-4}$haloalkyl and $SF_5$;

$R^{A2}$ is selected from the group consisting of halo, $C_{1-4}$alkyl, $C_{1-4}$haloalkyl, $C_{1-4}$alkoxy and $C_{1-4}$haloalkoxy;

$R^{A3}$ is $C_{1-2}$alkyl;

m is 0, 1 or 2;

n is 1 or 2;

p is 0, 1, 2, 3 or 4; and $R^B$ is selected from the group consisting of $CH_2COOH$, $CH_2CH_2COOH$, $CH_2$tetrazolyl and $CH_2CH_2$tetrazolyl, wherein $R^B$ is optionally substituted on an available carbon atom by one or more $R^{B1}$ wherein $R^{B1}$ is selected from the group consisting of difluoromethyl, trifluoromethyl and methyl, and/or wherein $R^B$ is optionally substituted by two $R^{B1}$ groups, attached to the same carbon atom, that are joined to form a $C_{3-6}$ cycloalkyl or a 4-6-membered heterocyclyl ring; and $R^C$ and $R^D$ are each independently H, $C_{1-2}$ alkyl, hydroxy, methoxy or fluoro; or a pharmaceutically acceptable salt and/or solvate thereof.

The present invention provides a pharmaceutical composition comprising a compound of formula (I) or a pharmaceutically acceptable salt and/or solvate thereof.

The present invention provides a compound of formula (I) or a pharmaceutically acceptable salt and/or solvate thereof for use as a medicament.

The present invention provides a compound of formula (I) or a pharmaceutically acceptable salt and/or solvate thereof for use in treating or preventing an inflammatory disease or a disease associated with an undesirable immune response.

The present invention provides the use of a compound of formula (I) or a pharmaceutically acceptable salt and/or solvate thereof in the manufacture of a medicament for treating or preventing an inflammatory disease or a disease associated with an undesirable immune response.

The present invention provides a method of treating or preventing an inflammatory disease or a disease associated with an undesirable immune response, which comprises administering a compound of formula (I) or a pharmaceutically acceptable salt and/or solvate thereof.

Also provided are intermediate compounds of use in the preparation of compounds of formula (I).

DETAILED DESCRIPTION OF THE INVENTION

Compounds of Formula (I)

Embodiments and preferences set out herein with respect to the compound of formula (I) apply equally to the pharmaceutical composition, compound for use, use and method aspects of the invention.

In one embodiment, there is provided a compound of formula (I):

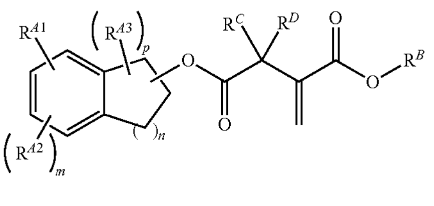

(I)

wherein:

$R^{A1}$ is selected from the group consisting of H, halo, $C_{1-4}$alkyl, $C_{1-4}$haloalkyl, $C_{1-4}$alkoxy, $C_{1-4}$haloalkoxy, —$SC_{1-4}$alkyl, —$SC_{1-4}$haloalkyl and $SF_5$;

$R^{A2}$ is selected from the group consisting of halo, $C_{1-4}$alkyl, $C_{1-4}$haloalkyl, $C_{1-4}$alkoxy and $C_{1-4}$haloalkoxy;

$R^{A3}$ is $C_{1-2}$alkyl;

m is 0, 1 or 2;

n is 1 or 2;

p is 0 or 1; and $R^B$ is selected from the group consisting of $CH_2COOH$, $CH_2CH_2COOH$, $CH_2$tetrazolyl and $CH_2CH_2$tetrazolyl, wherein $R^B$ is optionally substituted on an available carbon atom by one or more $R^{B1}$ wherein $R^{B1}$ is selected from the group consisting of difluoromethyl, trifluoromethyl and methyl, and/or wherein $R^B$ is optionally substituted by two $R^{B1}$ groups, attached to the same carbon atom, that are joined to form a $C_{3-6}$ cycloalkyl or a 4-6-membered heterocyclyl ring; and $R^C$ and $R^D$ are each independently H, $C_{1-2}$ alkyl, hydroxy, methoxy or fluoro; or a pharmaceutically acceptable salt and/or solvate thereof.

In another embodiment there is provided a compound of formula (I):

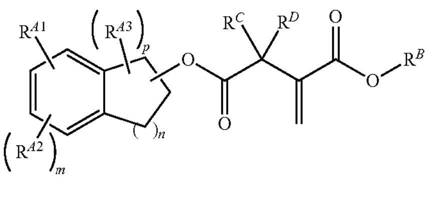

(I)

wherein:

$R^{A1}$ is selected from the group consisting of halo, $C_{1-4}$alkyl, $C_{1-4}$haloalkyl, $C_{1-4}$alkoxy, $C_{1-4}$haloalkoxy, —$SC_{1-4}$alkyl, —$SC_{1-4}$haloalkyl and $SF_5$;

$R^{A2}$ is selected from the group consisting of halo, $C_{1-4}$alkyl, $C_{1-4}$haloalkyl, $C_{1-4}$alkoxy and $C_{1-4}$haloalkoxy;

$R^{A3}$ is $C_{1-2}$alkyl;

m is 0, 1 or 2;

n is 1 or 2;

p is 0 or 1; and $R^B$ is selected from the group consisting of $CH_2COOH$, $CH_2CH_2COOH$, $CH_2$tetrazolyl and $CH_2CH_2$tetrazolyl, wherein $R^B$ is optionally substituted on an available carbon atom by one or more $R^{B1}$ wherein $R^{B1}$ is selected from the group consisting of difluoromethyl, trifluoromethyl and methyl, and/or wherein $R^B$ is optionally substituted by two $R^{B1}$ groups, attached to the same carbon atom, that are joined to form a $C_{3-6}$ cycloalkyl or a 4-6-membered heterocyclyl ring; and $R^C$ and $R^D$ are each independently H, $C_{1-2}$ alkyl, hydroxy, methoxy or fluoro; or a pharmaceutically acceptable salt and/or solvate thereof.

The term "$C_{1-4}$ alkyl" such as "$C_{1-2}$alkyl" refers to a straight or branched fully saturated hydrocarbon group having from 1 to 4 carbon atoms. The term encompasses methyl, ethyl, n-propyl, isopropyl, n-butyl, isobutyl, sec-butyl and tert-butyl. Suitably, the $C_{1-4}$ alkyl group is methyl.

The term "$C_{1-4}$ alkoxy" refers to a $C_{1-4}$ alkyl group (e.g. $C_{1-3}$ alkyl group, $C_{1-2}$ alkyl group or C, alkyl group) as defined above, singularly bonded to oxygen. The term encompasses methoxy, ethoxy, 1-propoxy and 2-propoxy, and is suitably methoxy.

The term "$C_{1-4}$ haloalkyl" as used herein refers to a straight or a branched fully saturated hydrocarbon chain containing the specified number of carbon atoms and at least one halogen atom, such as fluoro or chloro, especially fluoro. An example of haloalkyl is $CF_3$. Further examples of haloalkyl are $CHF_2$ and $CH_2CF_3$.

The term "$C_{1-4}$ haloalkoxy" refers to a $C_{1-4}$ haloalkyl group as defined above, singularly bonded to oxygen. Examples of $C_{1-4}$ haloalkoxy include $OCF_3$, $OCHF_2$ and $OCH_2CF_3$.

The term "$C_{3-6}$ cycloalkyl" refers to a fully saturated cyclic hydrocarbon group having from 3 to 6 carbon atoms. The term encompasses cyclopropyl, cyclobutyl, cyclopentyl and cyclohexyl. Suitably, $C_{3-6}$ cycloalkyl is cyclopropyl.

The term "4-6 membered heterocyclyl" refers to a non-aromatic cyclic group having 4 to 6 ring atoms and at least one heteroatom selected from N, O, S and B. The term "heterocyclyl" is interchangeable with "heterocyclic ring". The term encompasses oxetanyl, thietanyl, azetidinyl, pyrrolidinyl, tetrahydrofuranyl, tetrahydrothienyl, tetrahydropyranyl, piperidinyl, piperazinyl, morpholinyl and thiomorpholinyl. 4-6 membered heterocyclyl groups can typically be substituted by one or more oxo (=O) groups. Suitably, thietanyl is substituted by one or two oxo groups.

The term "hydroxy" (which may also be referred to as "hydroxyl") refers to an —OH group.

The term "halo" as used herein, refers to fluorine, chlorine, bromine or iodine. Particular examples of halo are fluorine and chlorine, especially fluorine.

In one embodiment, $R^{A1}$ is H.

In one embodiment, $R^{A1}$ is halo, such as chloro. In a second embodiment, $R^{A1}$ is $C_{1-4}$alkyl, such as methyl. In a third embodiment, $R^{A1}$ is $C_{1-4}$haloalkyl such as $CF_3$. In a fourth embodiment, $R^{A1}$ is $C_{1-4}$alkoxy, such as $OCH_3$. In a fifth embodiment, $R^{A1}$ is $C_{1-4}$haloalkoxy, such as $OCF_3$. In a sixth embodiment, $R^{A1}$ is —$SC_{1-4}$alkyl, such as —$SCH_3$. In a seventh embodiment, $R^{A1}$ is —$SC_{1-4}$haloalkyl, such as —$SCF_3$. In an eighth embodiment, $R^{A1}$ is $SF_5$.

Suitably, $R^{A1}$ is halo, such as chloro.

In one embodiment, $R^{A2}$ is halo, such as chloro. In a second embodiment, $R^{A2}$ is $C_{1-4}$alkyl, such as methyl. In a third embodiment, $R^{A2}$ is $C_{1-4}$haloalkyl such as $CF_3$, In a fourth embodiment, $R^{A2}$ is $C_{1-4}$alkoxy, such as $OCH_3$. In a fifth embodiment, $R^{A2}$ is $C_{1-4}$haloalkoxy, such as $OCF_3$.

Suitably, $R^{A2}$ is halo, such as chloro.

In one embodiment, m is 0. In a second embodiment, m is 1. In a third embodiment, m is 2.

Suitably, m is 0 or 1.

In one embodiment, n is 1. In a second embodiment, n is 2.

Suitably, n is 1.

When n is 1, compounds of formula (I) with the following moiety form:

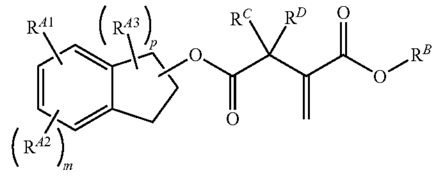

wherein $R^{A1}$, $R^{A2}$, $R^{A3}$, $R^B$, $R^C$, $R^D$, m and p are as defined elsewhere herein.

When n is 2, compounds of formula (I) with the following structure form:

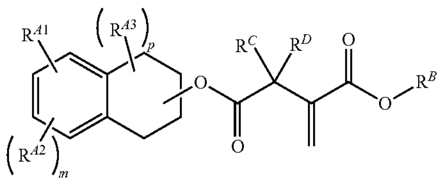

wherein $R^{A1}$, $R^{A2}$, $R^{A3}$, $R^B$, $R^C$, $R^D$, m and p are as defined elsewhere herein.

In one embodiment, p is 0. In a second embodiment, p is 1. In a third embodiment, p is 2. In a fourth embodiment, p is 3. In a fifth embodiment, p is 4. Suitably, p is 0. Alternatively, p is 4. When p is 4, suitably two $R^{A3}$ groups (such as methyl) are attached to one carbon atom of the cycloalkyl ring and two $R^{A3}$ groups (such as methyl) are attached to another carbon atom of the cycloalkyl ring. In this embodiment, suitably the cycloalkyl ring is cyclopentyl:

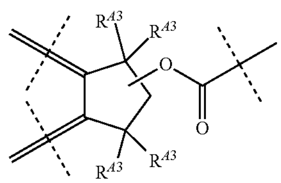

wherein the dashed lines indicate connection to the rest of the compound of formula (I).

In one embodiment, $R^{A3}$ is methyl. In another embodiment, $R^{A3}$ is ethyl. Suitably, $R^{A3}$ is methyl.

When p is 1, suitably $R^{A3}$ is attached to the same carbon atom as the cycloalkyl oxygen atom of the left hand side ester group.

The oxygen atom of the left hand side ester group may be attached to any one of the carbon atoms of the cyclopentyl or cyclohexyl ring in the 6,5- or 6,6-bicyclic moiety.

In one embodiment, the oxygen atom of the left hand side ester group is attached as follows:

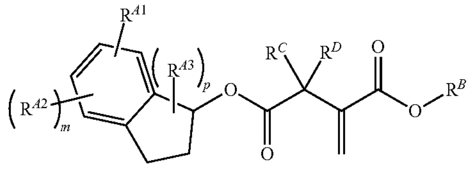

wherein $R^{A1}$, $R^{A2}$, $R^{A3}$, $R^B$, $R^C$, $R^D$, m and p are as defined elsewhere herein.

In a second embodiment, the oxygen atom of the left hand side ester group is attached as follows:

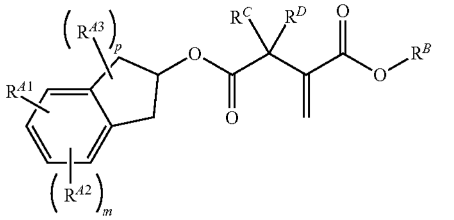

wherein $R^{A1}$, $R^{A2}$, $R^{A3}$, $R^B$, $R^C$, $R^D$, m and p are as defined elsewhere herein.

In a third embodiment, the oxygen atom of the left hand side ester group is attached as follows:

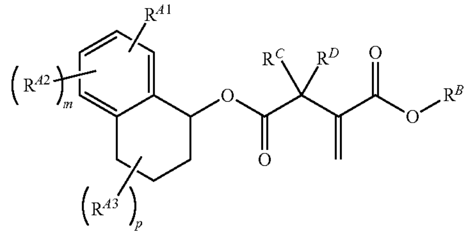

wherein $R^{A1}$, $R^{A2}$, $R^{A3}$, $R^B$, $R^C$, $R^0$, m and p are as defined elsewhere herein.

In a fourth embodiment, the oxygen atom of the left hand side ester group is attached as follows:

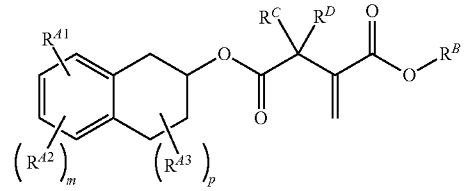

wherein $R^{A1}$, $R^{A2}$, $R^{A3}$, $R^B$, $R^C$, $R^D$, m and p are as defined elsewhere herein.

In one embodiment, $R^B$ is $CH_2COOH$ optionally substituted on an available carbon atom by one or more $R^{B1}$. In another embodiment, $R^B$ is $CH_2CH_2COOH$ optionally substituted on an available carbon atom by one or more $R^{B1}$.

In one embodiment, $R^B$ is $CH_2$tetrazolyl optionally substituted on an available carbon atom by one or more $R^{B1}$. In another embodiment, $R^B$ is $CH_2CH_2$tetrazolyl optionally substituted on an available carbon atom by one or more $R^{B1}$.

Suitably, $R^B$ is $CH_2COOH$ optionally substituted on an available carbon atom by one or more $R^{B1}$.

In one embodiment, $R^B$ is not substituted.

In another embodiment, $R^B$ is substituted on an available carbon atom by one or more (such as one, two or three, e.g. one) $R^{B1}$.

As used herein, the term "available carbon" means any C—H bond in $R^B$ wherein the H atom may be replaced by $R^{B1}$. In particular, a C—H bond of $CH_2$ or $CH_2CH_2$ within the $R^B$ moiety is replaced by C—$R^{B1}$.

In one embodiment, $R^{B1}$ is difluoromethyl. In a second embodiment, $R^{B1}$ is trifluoromethyl. In a third embodiment, $R^{B1}$ is methyl.

Suitably, the $R^{B1}$ group is to the carbon atom of $R^B$ adjacent to the ester oxygen atom i.e. such that the following moiety forms:

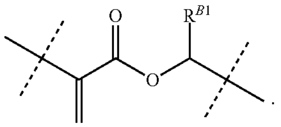

In a fourth embodiment, $R^B$ is substituted by two $R^{B1}$ groups, attached to the same carbon atom, that are joined to form a $C_{3-6}$ cycloalkyl or a 4-6-membered heterocyclyl ring. Suitably, the two $R^{B1}$ groups are joined to form a $C_{3-6}$ cycloalkyl ring (such as a cyclopropyl ring). Alternatively, the two $R^{B1}$ groups are joined to form a 4-6-membered heterocyclyl ring.

Suitably, $R^B$ is not substituted.

In one embodiment, $R^C$ and $R^D$ are independently selected from the group consisting of H, $C_{1-2}$ alkyl, hydroxy, methoxy and fluoro.

In one embodiment, $R^C$ is H. In a second embodiment, $R^C$ is $C_{1-2}$ alkyl, in particular methyl. In a third embodiment, $R^C$ is hydroxy. In a fourth embodiment, $R^C$ is methoxy. In a fifth embodiment, $R^C$ is fluoro.

In one embodiment, $R^D$ is H. In a second embodiment, $R^D$ is $C_{1-2}$ alkyl, in particular methyl. In a third embodiment, $R^D$ is hydroxy. In a fourth embodiment, $R^D$ is methoxy. In a fifth embodiment, $R^D$ is fluoro.

Suitably, $R^C$ and $R^D$ are both H.

In one embodiment, the molecular weight of the compound of formula (I) is 300 Da-450 Da.

In one embodiment there is provided a compound of formula (I), selected from the group consisting of:

2-((4-((5-chloro-2,3-dihydro-1H-inden-2-yl)oxy)-2-methylene-4-oxobutanoyl)oxy)acetic acid;

2-((4-((4,6-dichloro-2,3-dihydro-1H-inden-1-yl)oxy)-2-methylene-4-oxobutanoyl)oxy)acetic acid (Enantiomer 1);

2-((4-((4,6-dichloro-2,3-dihydro-1H-inden-1-yl)oxy)-2-methylene-4-oxobutanoyl)oxy)acetic acid (Enantiomer 2);

2-((4-((5,6-dichloro-2,3-dihydro-1H-inden-2-yl)oxy)-2-methylene-4-oxobutanoyl)oxy)acetic acid;

2-((4-((5,6-dichloro-2,3-dihydro-1H-inden-1-yl)oxy)-2-methylene-4-oxobutanoyl)oxy)acetic acid (Enantiomer 1);

2-((4-((5,6-dichloro-2,3-dihydro-1H-inden-1-yl)oxy)-2-methylene-4-oxobutanoyl)oxy)acetic acid (Enantiomer 2);

2-((4-((5-chloro-2-methyl-2,3-dihydro-1H-inden-2-yl)oxy)-2-methylene-4-oxobutanoyl)oxy)acetic acid;

2-((4-((5,7-dichloro-2,3-dihydro-1H-inden-1-yl)oxy)-2-methylene-4-oxobutanoyl)oxy)acetic acid (Enantiomer 1); and 2-((4-((5,7-dichloro-2,3-dihydro-1H-inden-1-yl)oxy)-2-methylene-4-oxobutanoyl)oxy)acetic acid (Enantiomer 2);

or a pharmaceutically acceptable salt and/or solvate of any one thereof.

In another embodiment, there is provided a compound of formula (I), selected from the group consisting of:

2-((4-((6,8-dichloro-1,2,3,4-tetrahydronaphthalen-2-yl)oxy)-2-methylene-4-oxobutanoyl)oxy)acetic acid (Enantiomer 1);

2-((4-((6,8-dichloro-1,2,3,4-tetrahydronaphthalen-2-yl)oxy)-2-methylene-4-oxobutanoyl)oxy)acetic acid (Enantiomer 2);

2-((4-((5-bromo-6-methoxy-2,3-dihydro-1H-inden-1-yl)oxy)-2-methylene-4-oxobutanoyl)oxy)acetic acid (Enantiomer 1);

2-((4-((5-bromo-6-methoxy-2,3-dihydro-1H-inden-1-yl)oxy)-2-methylene-4-oxobutanoyl)oxy)acetic acid (Enantiomer 2);

3-((4-((4,6-dichloro-2,3-dihydro-1H-inden-1-yl)oxy)-2-methylene-4-oxobutanoyl)oxy)propanoic acid (Enantiomer 1);

2-((4-((4-bromo-6-fluoro-2,3-dihydro-1H-inden-1-yl)oxy)-2-methylene-4-oxobutanoyl)oxy)acetic acid (Enantiomer 1);

2-((4-((4-bromo-6-fluoro-2,3-dihydro-1H-inden-1-yl)oxy)-2-methylene-4-oxobutanoyl)oxy)acetic acid (Enantiomer 2);

2-((2-methylene-4-oxo-4-((5-(trifluoromethyl)-2,3-dihydro-1H-inden-1-yl)oxy)butanoyl)oxy)acetic acid;

2-((2-methylene-4-oxo-4-((6-(trifluoromethoxy)-2,3-dihydro-1H-inden-1-yl)oxy)butanoyl)oxy)acetic acid;

2-((4-((4-chloro-6-fluoro-2,3-dihydro-1H-inden-1-yl)oxy)-2-methylene-4-oxobutanoyl)oxy)acetic acid (Enantiomer 1);

2-((4-((4-chloro-6-fluoro-2,3-dihydro-1H-inden-1-yl)oxy)-2-methylene-4-oxobutanoyl)oxy)acetic acid (Enantiomer 2);

2-((4-((5,6-dichloro-2-methyl-2,3-dihydro-1H-inden-2-yl)oxy)-2-methylene-4-oxobutanoyl)oxy)acetic acid;

(3R)-3-((4-((4,6-dichloro-2,3-dihydro-1H-inden-1-yl)oxy)-2-methylene-4-oxobutanoyl)oxy)-4,4,4-trifluorobutanoic acid (Diastereomer A);

(3S)-3-((4-((4,6-dichloro-2,3-dihydro-1H-inden-1-yl)oxy)-2-methylene-4-oxobutanoyl)oxy)-4,4,4-trifluorobutanoic acid (Diastereomer B);

2-((4-((5,7-dichloro-1,2,3,4-tetrahydronaphthalen-1-yl)oxy)-2-methylene-4-oxobutanoyl)oxy)acetic acid (Enantiomer 1);

2-((4-((5,7-dichloro-1,2,3,4-tetrahydronaphthalen-1-yl)oxy)-2-methylene-4-oxobutanoyl)oxy)acetic acid (Enantiomer 2);

2-((4-((5,6-difluoro-1,1,3,3-tetramethyl-2,3-dihydro-1H-inden-2-yl)oxy)-2-methylene-4-oxobutanoyl)oxy)acetic acid;

2-((2-methylene-4-oxo-4-((5-(trifluoromethyl)-2,3-dihydro-1H-inden-1-yl)oxy)butanoyl)oxy)acetic acid (Enantiomer 1);

2-((2-methylene-4-oxo-4-((6-(trifluoromethoxy)-2,3-dihydro-1H-inden-1-yl)oxy)butanoyl)oxy)acetic acid (Enantiomer 1); and 2-((2-methylene-4-oxo-4-((5-(trifluoromethyl)-2,3-dihydro-1H-inden-1-yl)oxy)butanoyl)oxy)acetic acid (Enantiomer 2);

or a pharmaceutically acceptable salt and/or solvate of any one thereof.

In another embodiment, there is provided a compound of formula (I), selected from the group consisting of:

2-((2-methylene-4-oxo-4-((6-(trifluoromethoxy)-2,3-dihydro-1H-inden-1-yl)oxy)butanoyl)oxy)acetic acid (Enantiomer 2); and 2-((2-methylene-4-oxo-4-((6-(trifluoromethyl)-1,2,3,4-tetrahydronaphthalen-1-yl)oxy)butanoyl)oxy)acetic acid (Enantiomer 1);

or a pharmaceutically acceptable salt and/or solvate of any one thereof.

Compounds of formula (I) may be prepared using the following route:

(VI), or (b) X—$R^{B'}$ wherein X represents a leaving group, such as chloro, bromo, iodo, alkanesulfonate, e.g., methanesulfonate, or arenesulfonate, e.g., para-toluenesulfonate or benzenesulfonate, and $R^{B'}$ represents a protected derivative of $R^B$ (wherein the $R^B$ protecting group may be for example $C_{1-4}$alkyl, e.g., tBu, or $CH_2CCl_3$), under basic conditions, such as in the presence of potassium carbonate in DMF, to give compounds of formula (VI). When $R^B$ comprises tetrazolyl, the tetrazolyl is suitably protected with a protecting group, such as para-methoxybenzyl.

Step (iii): The orthogonal protecting group PG is removed using conditions known to the person skilled in the art (such as Zn/AcOH when PG is $CH_2CCl_3$; acidic conditions when PG is PMB) to give itaconate (V) possessing a free carboxyl group at the 4-position.

Step (iv): Itaconate (V) is coupled with alcohol (III) under standard coupling conditions, to give monoester (II).

Step (v): The protecting group of $R^{B'}$ in compounds of formula (II) is removed, for example under acidic conditions, such as TFA in DCM (when $R^B$ is protected with

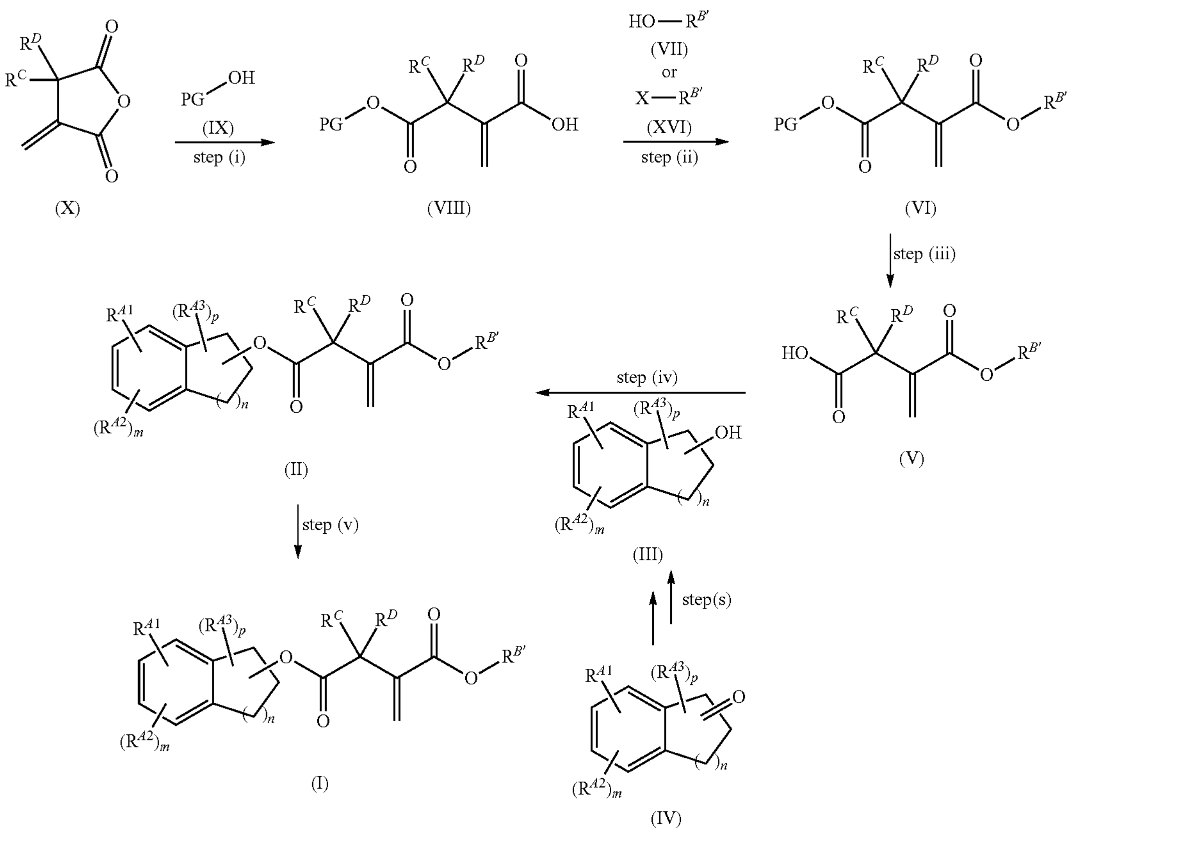

$R^{A1}$, $R^{A2}$, $R^{A3}$, $R^B$, $R^C$, $R^D$, m, n and p are as defined elsewhere herein.

Step (i): itaconate anhydride (X) can be reacted with alcohol (IX), wherein PG represents a protecting group (such as $CH_2CCl_3$ or PMB), in the presence of a catalyst such as $BF_3 \cdot Et_2O$ to give monoester (VIII).

Step (ii): Monoester (VIII) is coupled with either (a) HO—$R^{B'}$, wherein $R^{B'}$ represents a protected derivative of $R^B$ (wherein the $R^B$ protecting group may be for example $C_{1-4}$alkyl e.g. tBu, or $CH_2CCl_3$), using a coupling agent, like HATU or EDCI, in the presence of a base, such as DIPEA, and a catalyst, e.g., DMAP, to give compounds of formula $C_{1-4}$alkyl e.g. tBu) or Zn/AcOH (when $R^B$ is protected with $CH_2CCl_3$) to give compounds of formula (I).

Compounds of formula (III) may be accessed in a single step by reduction of the carbonyl group in cycloalkanone (IV) under standard carbonyl reduction conditions, or in multiple steps via a reduction-elimination-epoxidation-ring opening-reduction sequence as shown in the Example section.

Compounds of formula (I) may additionally be made by the following route:

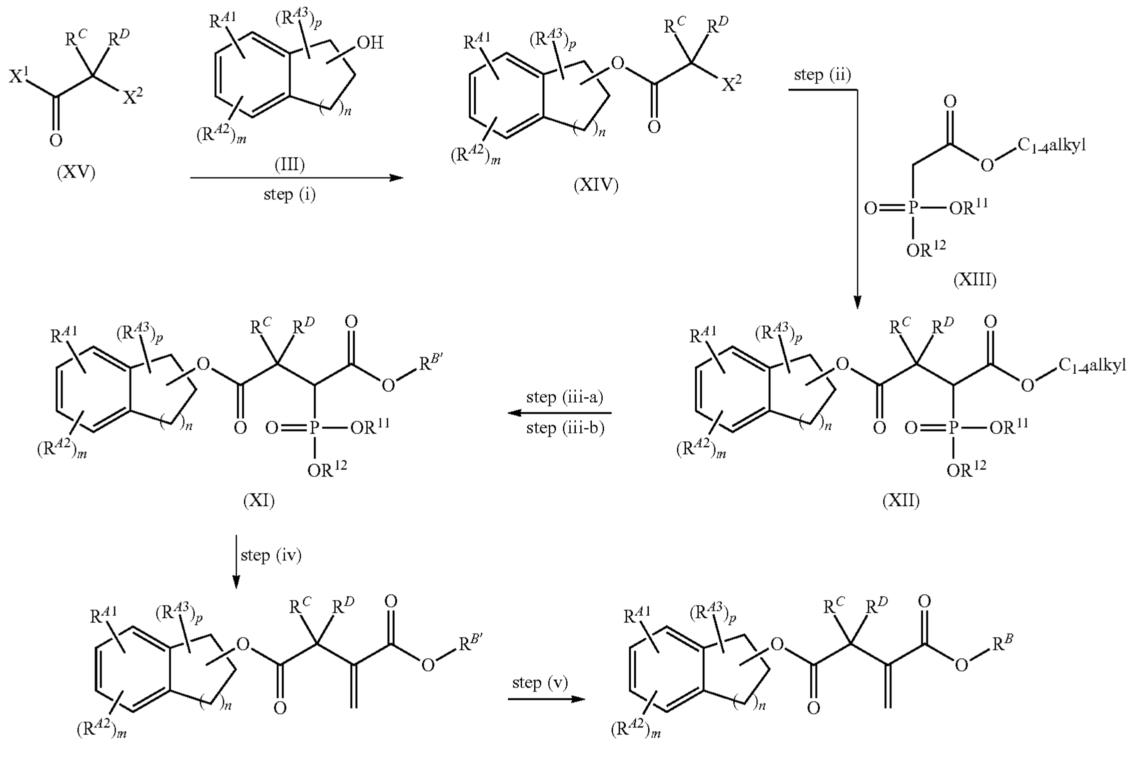

(XV) (III) (XIV) (XIII) (XII) (XI) (II) (I)

$R^{A1}$, $R^{A2}$, $R^{A3}$, $R^{B}$, $R^{C}$, $R^{D}$, m, n and p are as defined elsewhere herein.

This route is particularly favoured when compounds of formula (III) comprise a tertiary alcohol moiety.

Step (i): Alcohol (Ill) is condensed with compound (XV), wherein $X^1$ and $X^2$ represent leaving groups, such as halo e.g., chloro, bromo or iodo, to give monoester (XIV).

Step (ii): Monoester (XIV) is reacted with a trialkylphosphonoacetate of formula (XIII), wherein $R^{11}$ and $R^{12}$ independently represent $C_{1-4}$ alkyl optionally substituted with halo, to provide a compound of formula (XII).

Step (iii): The $C_{1-4}$alkyl ester in compounds of formula (XII) may undergo basic hydrolysis to give the corresponding acid (step (iii-a)) before the acid is coupled under standard conditions to introduce $R^{B'}$ (step (iii-b)) wherein $R^{B'}$ is defined elsewhere herein, to give compounds of formula (XI).

Step (iv): Condensation of a compound of formula (XI) with formaldehyde or a formaldehyde equivalent thereof e.g., paraformaldehyde, provides compounds of formula (II).

Step (v): The protecting group of $R^{B'}$ in compounds of formula (II) is removed, for example under acidic conditions, such as TFA in DCM (when PG is $C_{1-4}$alkyl e.g. tBu), or using Zn/AcOH (when PG is $CH_2CCl_3$) to give compounds of formula (I).

Compounds of formula (II) may also be made via the following route:

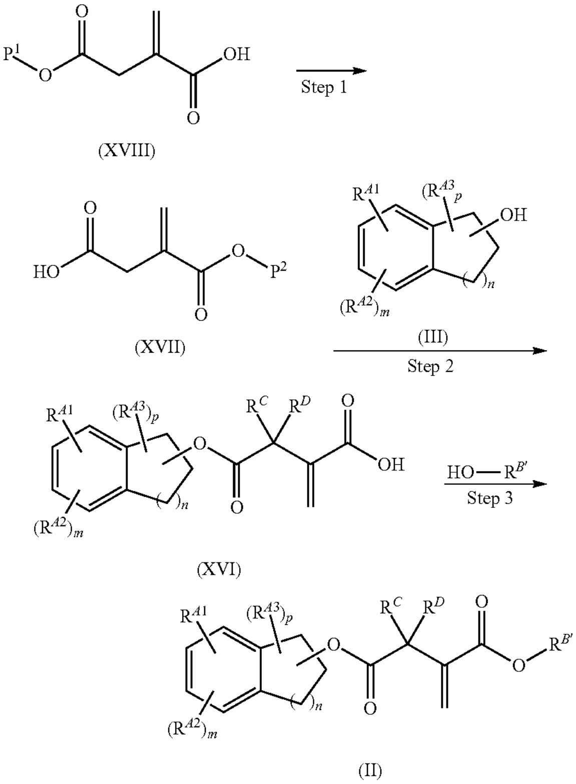

(XVIII) (XVII) (III) (XVI) (II)

$R^{A1}$, $R^{A2}$, $R^{A3}$, $R^{B'}$, $R^C$, $R^D$, m, n and p are as defined elsewhere herein, and $P^1$ and $P^2$ are orthogonal carboxylic acid protecting groups e.g. $P^1$ is PMB and $P^2$ is $CH_2CCl_3$.

Step 1: Compounds of formula (XVIII) may be converted to compounds of formula (XVII) by protection with $P^2$ and removal of $P^1$ using conditions known to the skilled person.

Step 2: Compounds of formula (XVI) may be obtained via coupling compounds of formula (III) (synthesised as described above from compounds of formula (IV)) with compounds of formula (XVII) using conditions described elsewhere herein such as EDC·HCl and DMAP (see e.g. conversion of compounds of formula (V) to compounds of formula (II)).

Step 3: Compounds of formula (XVI) are coupled with HO—$R^{B'}$ to give compounds of formula (II) under standard coupling conditions such as EDC·HCl and DMAP in the presence of a base such as DIPEA in a solvent such as THF.

The skilled person will appreciate that protecting groups may be used throughout the synthetic schemes described herein to give protected derivatives of any of the above compounds or generic formulae. Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540. Examples of nitrogen protecting groups include trityl (Tr), tert-butyloxycarbonyl (BOC), 9-fluorenylmethyloxycarbonyl (Fmoc), acetyl (Ac), benzyl (Bn) and para-methoxy benzyl (PMB). Examples of oxygen protecting groups include acetyl (Ac), methoxymethyl (MOM), para-methoxybenzyl (PMB), benzyl, tert-butyl, methyl, ethyl, tetrahydropyranyl (THP), and silyl ethers and esters (such as trimethylsilyl (TMS), tert-butyldimethylsilyl (TBDMS), tri-iso-propylsilyloxymethyl (TOM), and triisopropylsilyl (TIPS) ethers and esters). Specific examples of carboxylic acid protecting groups include alkyl esters (such as $C_{1-5}$ alkyl e.g. $C_{1-4}$ alkyl esters), benzyl esters and silyl esters.

Thus, in one embodiment there is provided a process for preparing a compound of formula (I) or a salt such as a pharmaceutically acceptable salt thereof, which comprises reacting a compound of formula (V):

(V)

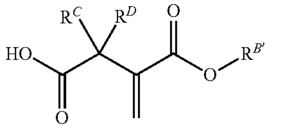

or a salt thereof;
with a compound of formula (III):

(III)

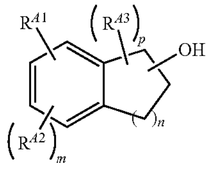

or a salt thereof;
followed by deprotection of $R^{B'}$;
wherein $R^{A1}$, $R^{A2}$, $R^{A3}$, $R^{B'}$, $R^C$, $R^D$, m, n and p are defined elsewhere herein.

In a second embodiment there is provided a process for preparing a compound of formula (I) or a salt such as a pharmaceutically acceptable salt thereof, which comprises reacting a compound of formula (XI):

(XI)

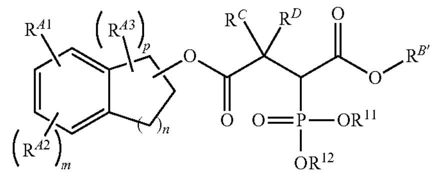

or a salt thereof;
with formaldehyde or a formaldehyde equivalent thereof e.g., paraformaldehyde; followed by deprotection of $R^{B'}$;
wherein $R^{A1}$, $R^{A2}$, $R^{A3}$, $R^C$, $R^D$, m, n, p, $R^{11}$, $R^{12}$ and $R^{B'}$ are defined elsewhere herein.

In one embodiment, there is provided a compound of formula (II):

(II)

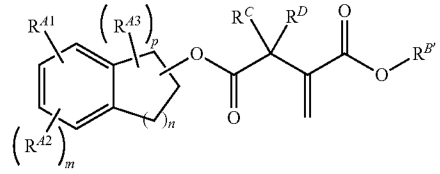

or a salt thereof;
wherein $R^{A1}$, $R^{A2}$, $R^{A3}$, $R^C$, $R^D$, m, n, p and $R^{B'}$ are defined elsewhere herein.

In another embodiment, there is provided a compound of formula (XI):

(XI)

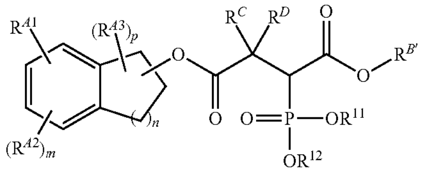

or a salt thereof;
wherein $R^{A1}$, $R^{A2}$, $R^{A3}$, $R^C$, $R^D$, m, n, p, $R^{B'}$, $R^{11}$ and $R^{12}$ are defined elsewhere herein.

In another embodiment, there is provided a compound of formula (XII):

(XII)

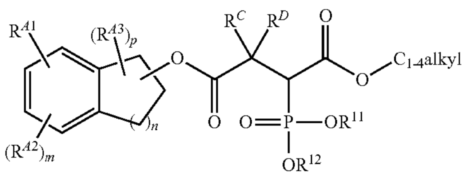

or a salt thereof;

wherein $R^{A1}$, $R^{A2}$, $R^{A3}$, $R^C$, $R^D$, m, n, p, $R^{11}$ and $R^{12}$ are defined elsewhere herein.

In another embodiment, there is provided a compound of formula (XIV):

(XIV)

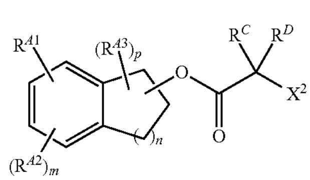

or a salt thereof;

wherein $R^{A1}$, $R^{A2}$, $R^{A3}$, $R^C$, $R^D$, m, n, p and $X^2$ are defined elsewhere herein.

In another embodiment, there is provided a compound of formula (XVI):

(XVI)

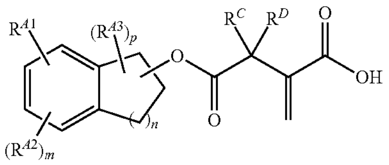

or a salt thereof;

wherein $R^{A1}$, $R^{A2}$, $R^{A3}$, $R^C$, $R^D$, m, n and p are defined elsewhere herein.

In another embodiment, there is provided a compound which is selected from the group consisting of:

1-(2-(tert-butoxy)-2-oxoethyl) 4-(5-chloro-2,3-dihydro-1H-inden-2-yl) 2-methylenesuccinate;

1-(2-(tert-butoxy)-2-oxoethyl) 4-(4,6-dichloro-2,3-dihydro-1H-inden-1-yl) 2-methylenesuccinate (enantiomer 1);

1-(2-(tert-butoxy)-2-oxoethyl) 4-(4,6-dichloro-2,3-dihydro-1H-inden-1-yl) 2-methylenesuccinate (enantiomer 2);

1-(2-(tert-butoxy)-2-oxoethyl) 4-(5,6-dichloro-2,3-dihydro-1H-inden-2-yl) 2-methylenesuccinate;

4-(5,6-dichloro-2,3-dihydro-1H-inden-1-yl) 1-(2-oxo-2-(2,2,2-trichloroethoxy)ethyl) 2-methylenesuccinate (enantiomer 1);

4-(5,6-dichloro-2,3-dihydro-1H-inden-1-yl) 1-(2-oxo-2-(2,2,2-trichloroethoxy)ethyl) 2-methylenesuccinate (enantiomer 2);

4-(5-chloro-2-methyl-2,3-dihydro-1H-inden-2-yl) 1-(2-oxo-2-(2,2,2-trichloroethoxy)ethyl) 2-methylenesuccinate;

4-(5,7-dichloro-2,3-dihydro-1H-inden-1-yl) 1-(2-oxo-2-(2,2,2-trichloroethoxy)ethyl) 2-methylenesuccinate (enantiomer 1);

4-(5,7-dichloro-2,3-dihydro-1H-inden-1-yl) 1-(2-oxo-2-(2,2,2-trichloroethoxy)ethyl) 2-methylenesuccinate (enantiomer 2);

or a salt thereof.

In another embodiment, there is provided a compound which is selected from the group consisting of:

3-((3-oxo-3-(2,2,2-trichloroethoxy)propoxy)carbonyl)but-3-enoic acid;

3-((2,2,2-trichloroethoxy)carbonyl)but-3-enoic acid;

4-(4,6-dichloro-2,3-dihydro-1H-inden-1-yl) 1-(3-oxo-3-(2,2,2-trichloroethoxy)propyl) 2-methylenesuccinate;

4-(4,6-dichloro-2,3-dihydro-1H-inden-1-yl) 1-((R)-1,1,1-trifluoro-4-oxo-4-(2,2,2-trichloroethoxy)butan-2-yl) 2-methylenesuccinate;

5,6-difluoro-1,1,3,3-tetramethyl-2,3-dihydro-1H-inden-2-ol;

5-(trifluoromethyl)-2,3-dihydro-1H-inden-1-ol (Enantiomer 1);

5-(trifluoromethyl)-2,3-dihydro-1H-inden-1-ol (Enantiomer 2); and 6-(trifluoromethoxy)-2,3-dihydro-1H-inden-1-ol (Enantiomer 1);

or a salt thereof.

In another embodiment, there is provided a compound which is selected from the group consisting of:

4-((4,6-dichloro-2,3-dihydro-1H-inden-1-yl)oxy)-2-methylene-4-oxobutanoic acid Enantiomer 1;

2-methylene-4-oxo-4-((5-(trifluoromethyl)-2,3-dihydro-1H-inden-1-yl)oxy)butanoic acid;

2-methylene-4-oxo-4-((6-(trifluoromethyl)-1,2,3,4-tetrahydronaphthalen-1-yl)oxy)butanoic acid Enantiomer 1; and 2-methylene-4-oxo-4-((6-(trifluoromethyl)-1,2,3,4-tetrahydronaphthalen-1-yl)oxy)butanoic acid Enantiomer 2;

or a salt thereof.

It will be appreciated that for use in therapy the salts of the compounds of formula (I) should be pharmaceutically acceptable. Suitable pharmaceutically acceptable salts will be apparent to those skilled in the art. Pharmaceutically acceptable salts include acid addition salts, suitably salts of compounds of the invention comprising a basic group such as an amino group, formed with inorganic acids e.g. hydrochloric acid, hydrobromic acid, sulfuric acid, nitric acid or phosphoric acid. Also included are salts formed with organic acids e.g. succinic acid, maleic acid, acetic acid, fumaric acid, citric acid, tartaric acid, benzoic acid, p-toluenesulfonic acid, methanesulfonic acid, naphthalenesulfonic acid and 1,5-naphthalenedisulfonic acid. Other salts e.g. oxalates or formates, may be used, for example in the isolation of compounds of formula (I) and are included within the scope of this invention, as are basic addition salts such as sodium, potassium, calcium, aluminium, zinc, magnesium and other metal salts.

Pharmaceutically acceptable salts may also be formed with organic bases such as basic amines e.g. with ammonia, meglumine, tromethamine, piperazine, arginine, choline, diethylamine, benzathine or lysine. Thus, in one embodiment there is provided a compound of formula (I) in the form of a pharmaceutically acceptable salt. Alternatively, there is provided a compound of formula (I) in the form of a free acid. When the compound contains a basic group as well as the free acid it may be Zwitterionic.

Suitably, the compound of formula (I) is not a salt e.g. is not a pharmaceutically acceptable salt.

Suitably, where the compound of formula (I) is in the form of a salt, the pharmaceutically acceptable salt is a basic addition salt such as a carboxylate salt formed with a group 1 metal (e.g. a sodium or potassium salt), a group 2 metal (e.g. a magnesium or calcium salt) or an ammonium salt of a basic amine (e.g. an $NH_4^+$ salt), such as a sodium salt.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water). Suitably, the compound of formula (I) is not a solvate.

The invention extends to a pharmaceutically acceptable derivative thereof, such as a pharmaceutically acceptable prodrug of compounds of formula (I). Typical prodrugs of compounds of formula (I) which comprise a carboxylic acid include ester (e.g. $C_{1-6}$ alkyl e.g. $C_{1-4}$ alkyl ester) derivatives thereof. Thus, in one embodiment, the compound of formula (I) is provided as a pharmaceutically acceptable prodrug. In another embodiment, the compound of formula (I) is not provided as a pharmaceutically acceptable prodrug.

Certain compounds of formula (I) may metabolise under certain conditions such as by hydrolysis of the $R^B$ ester group. Without wishing to be bound by theory, formation of an active metabolite (such as in vivo) of a compound of formula (I) may be beneficial by contributing to the biological activity observed of the compound of formula (I). Thus, in one embodiment, there is provided an active metabolite of the compound of formula (I) and its use as a pharmaceutical e.g. for the treatment or prevention of the diseases mentioned herein.

It is to be understood that the present invention encompasses all isomers of compounds of formula (I) including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present invention also includes all isotopic forms of the compounds provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 ($^{18}O$), phosphorus-32 ($^{32}P$), sulphur-35 ($^{35}S$), chlorine-36 ($^{36}Cl$), chlorine-37 ($^{37}Cl$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Unnatural variant isotopic forms which incorporate deuterium i.e. $^2H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in positron emission topography (PET) studies for examining substrate receptor occupancy.

In one embodiment, the compounds of formula (I) are provided in a natural isotopic form. In one embodiment, the compounds of formula (I) are provided in an unnatural variant isotopic form. In a specific embodiment, the unnatural variant isotopic form is a form in which deuterium (i.e. $^2H$ or D) is incorporated where hydrogen is specified in the chemical structure in one or more atoms of a compound of formula (I). In one embodiment, the atoms of the compounds of formula (I) are in an isotopic form which is not radioactive. In one embodiment, one or more atoms of the compounds of formula (I) are in an isotopic form which is radioactive. Suitably radioactive isotopes are stable isotopes. Suitably the unnatural variant isotopic form is a pharmaceutically acceptable form.

In one embodiment, a compound of formula (I) is provided whereby a single atom of the compound exists in an unnatural variant isotopic form. In another embodiment, a compound of formula (I) is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Therapeutic Indications

Compounds of formula (I) are of use in therapy, particularly for treating or preventing an inflammatory disease or a disease associated with an undesirable immune response. Compounds of formula (XVI) are also of use in therapy, particularly for treating or preventing an inflammatory disease or a disease associated with an undesirable immune response. As shown in Biological Example 1 below, example compounds of formula (I) and (XVI) reduced cytokine release more effectively than dimethyl itaconate, as demonstrated by lower $IC_{50}$ values. Cytokines are important mediators of inflammation and immune-mediated disease as evidenced by the therapeutic benefit delivered by antibodies targeting them.

Thus, in a first aspect, the present invention provides a compound of formula (I) or a pharmaceutically acceptable salt and/or solvate thereof as defined herein, for use as a medicament. In a second aspect, the present invention provides a compound of formula (XVI) or a pharmaceutically acceptable salt and/or solvate thereof, as defined herein, for use as a medicament. In a third aspect the present invention provides a pharmaceutical composition comprising a compound of formula (I) or a pharmaceutically acceptable salt and/or solvate thereof as defined herein. Such a pharmaceutical composition contains the compound of formula (I) and a pharmaceutically acceptable carrier or excipient. In a fourth aspect, the present invention provides a pharmaceutical composition comprising a compound of formula (XVI) or a pharmaceutically acceptable salt and/or solvate thereof, as defined herein. Such a pharmaceutical composition contains the compound of formula (XVI) and a pharmaceutically acceptable carrier or excipient.

In a further aspect, the present invention provides a compound of formula (I) or a pharmaceutically acceptable salt and/or solvate thereof as defined herein, for use in treating or preventing an inflammatory disease or a disease associated with an undesirable immune response. In a further aspect, the present invention provides the use of a compound of formula (I) or a pharmaceutically acceptable salt and/or solvate thereof as defined herein, in the manufacture of a medicament for treating or preventing an inflammatory disease or a disease associated with an undesirable immune response. In a further aspect, the present invention provides a method of treating or preventing an inflammatory disease or a disease associated with an undesirable immune response, which comprises administering a compound of formula (I) or a pharmaceutically acceptable salt and/or solvate thereof as defined herein.

In a further aspect, the present invention provides a compound of formula (XVI) or a pharmaceutically acceptable salt and/or solvate thereof, as defined herein, for use in treating or preventing an inflammatory disease or a disease associated with an undesirable immune response. In a further aspect, the present invention provides the use of a compound of formula (XVI) or a pharmaceutically acceptable salt and/or solvate thereof, as defined herein, in the manufacture of a medicament for treating or preventing an inflammatory disease or a disease associated with an undesirable immune response. In a further aspect, the present invention provides a method of treating or preventing an inflammatory disease or a disease associated with an undesirable immune response, which comprises administering a compound of formula (XVI) or a pharmaceutically acceptable salt and/or solvate thereof, as defined herein.

For all aspects of the invention, suitably the compound is administered to a subject in need thereof, wherein the subject is suitably a human subject.

In one embodiment is provided a compound of formula (I) or a pharmaceutically acceptable salt and/or solvate thereof as defined herein, for use in treating an inflammatory disease or disease associated with an undesirable immune response. In one embodiment of the invention is provided the use of a compound of formula (I) or a pharmaceutically acceptable salt and/or solvate thereof as defined herein, in the manufacture of a medicament for treating an inflammatory disease or a disease associated with an undesirable immune response. In one embodiment of the invention is provided a method of treating an inflammatory disease or a disease associated with an undesirable immune response, which comprises administering a compound of formula (I) or a pharmaceutically acceptable salt and/or solvate thereof as defined herein.

In one embodiment is provided a compound of formula (XVI) or a pharmaceutically acceptable salt and/or solvate thereof, as defined herein, for use in treating an inflammatory disease or disease associated with an undesirable immune response. In one embodiment of the invention is provided the use of a compound of formula (XVI) or a pharmaceutically acceptable salt and/or solvate thereof, as defined herein, in the manufacture of a medicament for treating an inflammatory disease or a disease associated with an undesirable immune response. In one embodiment of the invention is provided a method of treating an inflammatory disease or a disease associated with an undesirable immune response, which comprises administering a compound of formula (XVI) or a pharmaceutically acceptable salt and/or solvate thereof, as defined herein.

In one embodiment is provided a compound of formula (I) or a pharmaceutically acceptable salt and/or solvate thereof as defined herein, for use in preventing an inflammatory disease or a disease associated with an undesirable immune response. In one embodiment of the invention is provided the use of a compound of formula (I) or a pharmaceutically acceptable salt and/or solvate thereof as defined herein, in the manufacture of a medicament for preventing an inflammatory disease or a disease associated with an undesirable immune response. In one embodiment of the invention is provided a method of preventing an inflammatory disease or a disease associated with an undesirable immune response, which comprises administering a compound of formula (I) or a pharmaceutically acceptable salt and/or solvate thereof as defined herein.

In one embodiment is provided a compound of formula (XVI) or a pharmaceutically acceptable salt and/or solvate thereof, as defined herein, for use in preventing an inflammatory disease or a disease associated with an undesirable immune response. In one embodiment of the invention is provided the use of a compound of formula (XVI) or a pharmaceutically acceptable salt and/or solvate thereof, as defined herein, in the manufacture of a medicament for preventing an inflammatory disease or a disease associated with an undesirable immune response. In one embodiment of the invention is provided a method of preventing an inflammatory disease or a disease associated with an undesirable immune response, which comprises administering a compound of formula (XVI) or a pharmaceutically acceptable salt and/or solvate thereof, as defined herein.

In one embodiment is provided a compound of formula (I) or a pharmaceutically acceptable salt and/or solvate thereof as defined herein, for use in treating or preventing an inflammatory disease. In one embodiment of the invention is provided the use of a compound of formula (I) or a pharmaceutically acceptable salt and/or solvate thereof as defined herein, in the manufacture of a medicament for treating or preventing an inflammatory disease. In one embodiment of the invention is provided a method of treating or preventing an inflammatory disease, which comprises administering a compound of formula (I) or a pharmaceutically acceptable salt and/or solvate thereof as defined herein.

In one embodiment is provided a compound of formula (XVI) or a pharmaceutically acceptable salt and/or solvate thereof, as defined herein, for use in treating or preventing an inflammatory disease. In one embodiment of the invention is provided the use of a compound of formula (XVI) or a pharmaceutically acceptable salt and/or solvate thereof, as defined herein, in the manufacture of a medicament for treating or preventing an inflammatory disease. In one embodiment of the invention is provided a method of treating or preventing an inflammatory disease, which comprises administering a compound of formula (XVI) or a pharmaceutically acceptable salt and/or solvate thereof, as defined herein.

In one embodiment is provided a compound of formula (I) or a pharmaceutically acceptable salt and/or solvate thereof as defined herein, for use in treating or preventing a disease associated with an undesirable immune response. In one embodiment of the invention is provided the use of a compound of formula (I) or a pharmaceutically acceptable salt and/or solvate thereof as defined herein, in the manufacture of a medicament for treating or preventing a disease associated with an undesirable immune response. In one embodiment of the invention is provided a method of treating or preventing a disease associated with an undesirable immune response, which comprises administering a compound of formula (I) or a pharmaceutically acceptable salt and/or solvate thereof as defined herein.

In one embodiment is provided a compound of formula (XVI) or a pharmaceutically acceptable salt and/or solvate thereof, as defined herein, for use in treating or preventing a disease associated with an undesirable immune response. In one embodiment of the invention is provided the use of a compound of formula (XVI) or a pharmaceutically acceptable salt and/or solvate thereof, as defined herein, in the manufacture of a medicament for treating or preventing a disease associated with an undesirable immune response. In one embodiment of the invention is provided a method of treating or preventing a disease associated with an undesirable immune response, which comprises administering a compound of formula (XVI) or a pharmaceutically acceptable salt and/or solvate thereof, as defined herein.

An undesirable immune response will typically be an immune response which gives rise to a pathology, i.e., is a pathological immune response or reaction.

In one embodiment, the inflammatory disease or disease associated with an undesirable immune response is an auto-immune disease.

In one embodiment, the inflammatory disease or disease associated with an undesirable immune response is, or is associated with, a disease selected from the group consisting of: psoriasis (including chronic plaque, erythrodermic, pustular, guttate, inverse and nail variants), asthma, chronic obstructive pulmonary disease (COPD, including chronic bronchitis and emphysema), heart failure (including left ventricular failure), myocardial infarction, angina pectoris, other atherosclerosis and/or atherothrombosis-related disorders (including peripheral vascular disease and ischaemic stroke), a mitochondrial and neurodegenerative disease (such as Parkinson's disease, Alzheimer's disease, Huntington's disease, amyotrophic lateral sclerosis, retinitis pigmentosa or mitochondrial encephalomyopathy), autoimmune paraneoplastic retinopathy, transplantation rejection (including antibody-mediated and T cell-mediated forms), multiple sclerosis, transverse myelitis, ischaemia-reperfusion injury (e.g. during elective surgery such as cardiopulmonary bypass for coronary artery bypass grafting or other cardiac surgery, following percutaneous coronary intervention, following treatment of acute ST-elevation myocardial infarction or ischaemic stroke, organ transplantation, or acute compartment syndrome), AGE-induced genome damage, an inflammatory bowel disease (e.g. Crohn's disease or ulcerative colitis), primary sclerosing cholangitis (PSC), PSC-autoimmune hepatitis overlap syndrome, non-alcoholic fatty liver disease (non-alcoholic steatohepatitis), rheumatica, granuloma annulare, cutaneous lupus erythematosus (CLE), systemic lupus erythematosus (SLE), lupus nephritis, drug-induced lupus, autoimmune myocarditis or myopericarditis, Dressler's syndrome, giant cell myocarditis, post-pericardiotomy syndrome, drug-induced hypersensitivity syndromes (including hypersensitivity myocarditis), eczema, sarcoidosis, erythema nodosum, acute disseminated encephalomyelitis (ADEM), neuromyelitis optica spectrum disorders, MOG (myelin oligodendrocyte glycoprotein) antibody-associated disorders (including MOG-EM), optic neuritis, CLIPPERS (chronic lymphocytic inflammation with pontine perivascular enhancement responsive to steroids), diffuse myelinoclastic sclerosis, Addison's disease, alopecia areata, ankylosing spondylitis, other spondyloarthritides (including peripheral spondyloarthritis, that is associated with psoriasis, inflammatory bowel disease, reactive arthritis or juvenile onset forms), antiphospholipid antibody syndrome, autoimmune hemolytic anaemia, autoimmune hepatitis, autoimmune inner ear disease, pemphigoid (including bullous pemphigoid, mucous membrane pemphigoid, cicatricial pemphigoid, herpes gestationis or pemphigoid gestationis, ocular cicatricial pemphigoid), linear IgA disease, Behçet's disease, celiac disease, Chagas disease, dermatomyositis, diabetes mellitus type I, endometriosis, Goodpasture's syndrome, Graves' disease, Guillain-Barre syndrome and its subtypes (including acute inflammatory demyelinating polyneuropathy, AIDP, acute motor axonal neuropathy (AMAN), acute motor and sensory axonal neuropathy (AMSAN), pharyngeal-cervical-brachial variant, Miller-Fisher variant and Bickerstaff's brainstem encephalitis), progressive inflammatory neuropathy, Hashimoto's disease, hidradenitis suppurativa, inclusion body myositis, necrotising myopathy, Kawasaki disease, IgA nephropathy, Henoch-Schonlein purpura, idiopathic thrombocytopenic purpura, thrombotic thrombocytopenic purpura (TTP), Evans' syndrome, interstitial cystitis, mixed connective tissue disease, undifferentiated connective tissue disease, morphea, myasthenia gravis (including MuSK antibody positive and seronegative variants), narcolepsy, neuromyotonia, pemphigus vulgaris, pernicious anaemia, psoriatic arthritis, polymyositis, primary biliary cholangitis (also known as primary biliary cirrhosis), rheumatoid arthritis, palindromic rheumatism, schizophrenia, autoimmune (meningo-)encephalitis syndromes, scleroderma, Sjogren's syndrome, stiff person syndrome, polymylagia rheumatica, giant cell arteritis (temporal arteritis), Takayasu arteritis, polyarteritis nodosa, Kawasaki disease, granulomatosis with polyangitis (GPA; formerly known as Wegener's granulomatosis), eosinophilic granulomatosis with polyangiitis (EGPA; formerly known as Churg-Strauss syndrome), microscopic polyarteritis/polyangiitis, hypocomplementaemic urticarial vasculitis, hypersensitivity vasculitis, cryoglobulinemia, thromboangiitis obliterans (Buerger's disease), vasculitis, leukocytoclastic vasculitis, vitiligo, acute disseminated encephalomyelitis, adrenoleukodystrophy, Alexander's disease, Alper's disease, balo concentric sclerosis or Marburg disease, cryptogenic organising pneumonia (formerly known as bronchiolitis obliterans organizing pneumonia), Canavan disease, central nervous system vasculitic syndrome, Charcot-Marie-Tooth disease, childhood ataxia with central nervous system hypomyelination, chronic inflammatory demyelinating polyneuropathy (CIDP), diabetic retinopathy, globoid cell leukodystrophy (Krabbe disease), graft-versus-host disease (GVHD) (including acute and chronic forms, as well as intestinal GVHD), hepatitis C (HCV) infection or complication, herpes simplex viral infection or complication, human immunodeficiency virus (HIV) infection or complication, lichen planus, monomelic amyotrophy, cystic fibrosis, pulmonary arterial hypertension (PAH, including idiopathic PAH), lung sarcoidosis, idiopathic pulmonary fibrosis, paediatric asthma, atopic dermatitis, allergic dermatitis, contact dermatitis, allergic rhinitis, rhinitis, sinusitis, conjunctivitis, allergic conjunctivitis, keratoconjunctivitis sicca, dry eye, xerophthalmia, glaucoma, macular oedema, diabetic macular oedema, central retinal vein occlusion (CRVO), macular degeneration (including dry and/or wet age related macular degeneration, AMD), post-operative cataract inflammation, uveitis (including posterior, anterior, intermediate and pan uveitis), iridocyclitis, scleritis, corneal graft and limbal cell transplant rejection, gluten sensitive enteropathy (coeliac disease), dermatitis herpetiformis, eosinophilic esophagitis, achalasia, autoimmune dysautonomia, autoimmune encephalomyelitis, autoimmune oophoritis, autoimmune orchitis, autoimmune pancreatitis, aortitis and periaortitis, autoimmune retinopathy, autoimmune urticaria, Behcet's disease, (idiopathic) Castleman's disease, Cogan's syndrome, IgG4-related disease, retroperitoneal fibrosis, juvenile idiopathic arthritis including systemic juvenile idiopathic arthritis (Still's disease), adult-onset Still's disease, ligneous conjunctivitis, Mooren's ulcer, pityriasis lichenoides et varioliformis acuta (PLEVA, also known as Mucha-Habermann disease), multifocal motor neuropathy (MMN), paediatric acute-onset neuropsychiatric syndrome (PANS) (including paediatric autoimmune neuropsychiatric disorders associated with streptococcal infections (PANDAS)), paraneoplastic syndromes (including paraneoplastic cerebellar degeneration, Lambert-Eaton myaesthenic syndrome, limbic encephalitis, brainstem encephalitis, opsoclonus myoclonus ataxia syndrome, anti-NMDA receptor encephalitis, thymoma-associated multiorgan autoimmunity), perivenous encephalomyelitis, reflex sympathetic dystrophy, relapsing polychondritis, sperm & testicular autoimmunity, Susac's syndrome, Tolosa-Hunt syndrome, Vogt-Koyanagi-Harada Disease, anti-synthetase syndrome, autoimmune enteropathy, immune dysregulation polyendocrinopathy enteropathy X-linked (IPEX), microscopic colitis, autoimmune lymphoproliferative syndrome (ALPS), autoimmune polyendocrinopathy-candidiasis-ectodermal dystrophy syndrome (APEX), gout, pseudogout, amyloid (including AA or secondary amyloidosis), eosinophilic fasciitis (Shulman syndrome) progesterone hypersensitivity (including progesterone dermatitis), familial Mediterranean fever (FMF), tumour necrosis factor (TNF) receptor-associated periodic fever syndrome (TRAPS), hyperimmunoglobulinaemia D with periodic fever syndrome (HIDS), PAPA (pyogenic arthritis, pyoderma gangrenosum, severe cystic acne) syndrome, deficiency of interleukin-1 receptor antagonist (DIRA), deficiency of the interleukin-36-receptor antagonist (DITRA), cryopyrin-associated periodic syndromes (CAPS) (including familial cold autoinflammatory syndrome [FCAS], Muckle-Wells syndrome, neonatal onset multisystem inflammatory disease [NOMID]), NLRP12-associated autoinflammatory disorders (NLRP12AD), periodic fever aphthous stomatitis (PFAPA), chronic atypical neutrophilic dermatosis with lipodystrophy and elevated temperature (CANDLE), Majeed syndrome, Blau syndrome (also known as juvenile systemic granulomatosis), macrophage activation syndrome, chronic recurrent multifocal osteomyelitis (CRMO), familial cold autoinflammatory syndrome, mutant adenosine deaminase 2 and monogenic interferonopathies (including Aicardi-Goutieres syndrome, retinal vasculopathy with cerebral leukodystrophy, spondyloenchondrodysplasia, STING [stimulator of interferon genes]-associated vasculopathy with onset in infancy, proteasome associated autoinflammatory syndromes, familial chilblain lupus, dyschromatosis symmetrica hereditaria), Schnitzler syndrome; familial cylindromatosis, congenital B cell lymphocytosis, OTULIN-related autoinflammatory syndrome, type 2 diabetes mellitus, insulin resistance and the metabolic syndrome (including obesity-associated inflammation), atherosclerotic disorders (e.g. myocardial infarction, angina, ischaemic heart failure, ischaemic nephropathy, ischaemic stroke, peripheral vascular disease, aortic aneurysm), renal inflammatory disorders (e.g. diabetic nephropathy, membranous nephropathy, minimal change disease, crescentic glomerulonephritis, acute kidney injury, renal transplantation).

In one embodiment, the inflammatory disease or disease associated with an undesirable immune response is, or is associated with, a disease selected from the following autoinflammatory diseases: familial Mediterranean fever (FMF), tumour necrosis factor (TNF) receptor-associated periodic fever syndrome (TRAPS), hyperimmunoglobulinaemia D with periodic fever syndrome (HIDS), PAPA (pyogenic arthritis, pyoderma gangrenosum, and severe cystic acne) syndrome, deficiency of interleukin-1 receptor antagonist (DIRA), deficiency of the interleukin-36-receptor antagonist (DITRA), cryopyrin-associated periodic syndromes (CAPS) (including familial cold autoinflammatory syndrome [FCAS], Muckle-Wells syndrome, and neonatal onset multisystem inflammatory disease [NOMID]), NLRP12-associated autoinflammatory disorders (NLRP12AD), periodic fever aphthous stomatitis (PFAPA), chronic atypical neutrophilic dermatosis with lipodystrophy and elevated temperature (CANDLE), Majeed syndrome, Blau syndrome (also known as juvenile systemic granulomatosis), macrophage activation syndrome, chronic recurrent multifocal osteomyelitis (CRMO), familial cold autoinflammatory syndrome, mutant adenosine deaminase 2 and monogenic interferonopathies (including Aicardi-Goutières syndrome, retinal vasculopathy with cerebral leukodystrophy, spondyloenchondrodysplasia, STING [stimulator of interferon genes]-associated vasculopathy with onset in infancy, proteasome associated autoinflammatory syndromes, familial chilblain lupus, dyschromatosis symmetrica hereditaria) and Schnitzler syndrome.

In one embodiment, the inflammatory disease or disease associated with an undesirable immune response is, or is associated with, a disease selected from the following diseases mediated by excess NF-κB or gain of function in the NF-κB signalling pathway or in which there is a major contribution to the abnormal pathogenesis therefrom (including non-canonical NF-κB signalling): familial cylindromatosis, congenital B cell lymphocytosis, OTULIN-related autoinflammatory syndrome, type 2 diabetes mellitus, insulin resistance and the metabolic syndrome (including obesity-associated inflammation), atherosclerotic disorders (e.g. myocardial infarction, angina, ischaemic heart failure, ischaemic nephropathy, ischaemic stroke, peripheral vascular disease, aortic aneurysm), renal inflammatory disorders (e.g. diabetic nephropathy, membranous nephropathy, minimal change disease, crescentic glomerulonephritis, acute kidney injury, renal transplantation), asthma, COPD, type 1 diabetes mellitus, rheumatoid arthritis, multiple sclerosis, inflammatory bowel disease (including ulcerative colitis and Crohn's disease), and SLE.

In one embodiment, the disease is selected from the group consisting of rheumatoid arthritis, psoriatic arthritis, ankylosing spondylitis, systemic lupus erythematosus, multiple sclerosis, psoriasis, Crohn's disease, ulcerative colitis, uveitis, cryopyrin-associated periodic syndromes, Muckle-Wells syndrome, juvenile idiopathic arthritis and chronic obstructive pulmonary disease.

In one embodiment, the disease is multiple sclerosis.

In one embodiment, the disease is psoriasis.

In one embodiment, the compound of formula (I) exhibits a lower $IC_{50}$ compared with dimethyl itaconate when tested in a cytokine assay e.g. as described in Biological Example 1. In one embodiment, the compound of formula (I) exhibits a lower $IC_{50}$ compared with dimethyl fumarate when tested in a cytokine assay e.g. as described in Biological Example 1.

In one embodiment, the compound of formula (I) exhibits a lower $EC_{50}$ compared with dimethyl itaconate when tested in an NRF2 assay e.g. as described in Biological Example 2. In one embodiment, the compound of formula (I) exhibits a higher $E_{max}$ compared with dimethyl itaconate when tested in an NRF2 assay e.g. as described in Biological Example 2. In one embodiment, the compound of formula (I) exhibits a lower $EC_{50}$ and/or higher $E_{max}$ compared with dimethyl itaconate when tested in an NRF2 assay e.g. as described in Biological Example 2. In one embodiment, the compound of formula (I) exhibits a lower $EC_{50}$ and higher $E_{max}$ compared with dimethyl itaconate when tested in an NRF2 assay e.g. as described in Biological Example 2.

In one embodiment, the compound of formula (I) exhibits lower intrinsic clearance ($Cl_{int}$) compared with 4-octyl itaconate when tested in a hepatocyte stability assay (such as in human hepatocytes), e.g., as described in Biological Example 3. In one embodiment, the compound of formula (I) exhibits a longer half-life ($T_{1/2}$) compared with 4-octyl itaconate when tested in a hepatocyte stability assay (such as in human hepatocytes), e.g. as described in Biological Example 3.

Administration

The compound of formula (I) is usually administered as a pharmaceutical composition. Thus, in one embodiment, is provided a pharmaceutical composition comprising a compound of formula (I) and one or more pharmaceutically acceptable diluents or carriers.

The compound of formula (XVI) is usually administered as a pharmaceutical composition. Thus, in one embodiment, is provided a pharmaceutical composition comprising a compound of formula (XVI) and one or more pharmaceutically acceptable diluents or carriers.

Details below regarding pharmaceutical compositions and administration thereof in respect of compounds of formula (I) apply equally to compounds of formula (XVI).

The compound of formula (I) may be administered by any convenient method, e.g. by oral, parenteral, buccal, sublingual, nasal, rectal, intrathecal or transdermal administration, and the pharmaceutical compositions adapted accordingly.

The compound of formula (I) may be administered topically to the target organ e.g. topically to the eye, lung, nose or skin. Hence the invention provides a pharmaceutical composition comprising a compound of formula (I) optionally in combination with one or more topically acceptable diluents or carriers.

A compound of formula (I) which is active when given orally can be formulated as a liquid or solid, e.g. as a syrup, suspension, emulsion, tablet, capsule or lozenge.

A liquid formulation will generally consist of a suspension or solution of the compound of formula (I) in a suitable liquid carrier(s). Suitably the carrier is non-aqueous e.g. polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatine capsule; alternatively, a dispersion or suspension can be prepared using any suitable pharmaceutical carrier(s), e.g. aqueous gums, celluloses, silicates or oils and the dispersion or suspension then filled into a soft gelatine capsule.

Typical parenteral compositions consist of a solution or suspension of the compound of formula (I) in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the compound of formula (I) in a pharmaceutically acceptable aqueous or non-aqueous solvent and are usually presented in single or multidose quantities in sterile form in a sealed container which can take the form of a cartridge or refill for use with an atomising device. Alternatively, the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a chlorofluorocarbon (CFC) or a hydrofluorocarbon (HFC). Aerosol dosage forms can also take the form of pump-atomisers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC).

Topical administration to the lung may also be achieved by use of a non-pressurised formulation such as an aqueous solution or suspension. These may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents.

Topical administration to the lung may also be achieved by use of a dry-powder formulation. The formulation will typically contain a topically acceptable diluent such as lactose, glucose or mannitol (preferably lactose).

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of the present invention will be about 0.0001 to less than 4.0% (w/w).

Preferably, for topical ocular administration, the compositions administered according to the present invention will be formulated as solutions, suspensions, emulsions and other dosage forms.

The compositions administered according to the present invention may also include various other ingredients, including, but not limited to, tonicity agents, buffers, surfactants, stabilizing polymer, preservatives, co-solvents and viscosity building agents. Suitable pharmaceutical compositions of the present invention include a compound of the invention formulated with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of the present invention. The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of compounds of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Compositions suitable for buccal or sublingual administration include tablets, lozenges and pastilles where the compound of formula (I) is formulated with a carrier such as sugar and acacia, tragacanth, or gelatine and glycerine.

Compositions suitable for transdermal administration include ointments, gels and patches.

The composition may contain from 0.1% to 100% by weight, for example from 10 to 60% by weight, of the compound of formula (I), depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, such as from 1.0 mg to 50 mg, e.g. about 10 mg of the compound of formula (I), depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, such as from 1.0 mg to 50 mg, e.g. about 10 mg and such unit doses may be administered more than once a day, for example two or three times a day. Such therapy may extend for a number of weeks or months.

In one embodiment of the invention, the compound of formula (I) is used in combination with a further therapeutic agent or agents. When the compound of formula (I) is used in combination with other therapeutic agents, the compounds may be administered either sequentially or simultaneously by any convenient route. Alternatively, the compounds may be administered separately.

Therapeutic agents which may be used in combination with the present invention include: corticosteroids (glucocorticoids), retinoids (e.g. acitretin, isotretinoin, tazarotene), anthralin, vitamin D analogues (e.g. cacitriol, calcipotriol), calcineurin inhibitors (e.g. tacrolimus, pimecrolimus), phototherapy or photochemotherapy (e.g. psoralen ultraviolet irradiation, PUVA) or other form of ultraviolet light irradiation therapy, ciclosporine, thiopurines (e.g. azathioprine, 6-mercaptopurine), methotrexate, anti-TNFα agents (e.g. infliximab, etanercept, adalimumab, certolizumab, golimumab and biosimilars), phosphodiesterase-4 (PDE4) inhibition (e.g. apremilast, crisaborole), anti-IL-17 agents (e.g. brodalumab, ixekizumab, secukinumab), anti-IL12/IL-23 agents (e.g. ustekinumab, briakinumab), anti-IL-23 agents (e.g. guselkumab, tildrakizumab), JAK (Janus Kinase) inhibitors (e.g. tofacitinib, ruxolitinib, baricitinib, filgotinib, upadacitinib), plasma exchange, intravenous immune globulin (IVIG), cyclophosphamide, anti-CD20 B cell depleting agents (e.g. rituximab, ocrelizumab, ofatumumab, obinutuzumab), anthracycline analogues (e.g. mitoxantrone), cladribine, sphingosine 1-phosphate receptor modulators or sphingosine analogues (e.g. fingolimod, siponimod, ozanimod, etrasimod), interferon beta preparations (including interferon beta 1b/1a), glatiramer, anti-CD3 therapy (e.g. OKT3), anti-CD52 targeting agents (e.g. alemtuzumab), leflunomide, teriflunomide, gold compounds, laquinimod, potassium channel blockers (e.g. dalfampridine/4-aminopyridine), mycophenolic acid, mycophenolate mofetil, purine analogues (e.g. pentostatin), mTOR (mechanistic target of rapamycin) pathway inhibitors (e.g. sirolimus, everolimus), anti-thymocyte globulin (ATG), IL-2 receptor (CD25) inhibitors (e.g. basiliximab, daclizumab), anti-IL-6 receptor or anti-IL-6 agents (e.g. tocilizumab, siltuximab), Bruton's tyrosine kinase (BTK) inhibitors (e.g. ibrutinib), tyrosine kinase inhibitors (e.g. imatinib), ursodeoxycholic acid, hydroxychloroquine, chloroquine, B cell activating factor (BAFF, also known as BLyS, B lymphocyte stimulator) inhibitors (e.g. belimumab, blisibimod), other B cell targeted therapy including fusion proteins targeting both APRIL (A PRoliferation-Inducing Ligand) and BLyS (e.g. atacicept), PI3K inhibitors including pan-inhibitors or those targeting the p110δ and/or p110γ containing isoforms (e.g. idelalisib, copanlisib, duvelisib), interferon α receptor inhibitors (e.g. anifrolumab, sifalimumab), T cell co-stimulation blockers (e.g. abatacept, belatacept), thalidomide and its derivatives (e.g. lenalidomide), dapsone, clofazimine, leukotriene antagonists (e.g. montelukast), theophylline, anti-IgE therapy (e.g. omalizumab), anti-IL-5 agents (e.g. mepolizumab, reslizumab), long-acting muscarinic agents (e.g. tiotropium, aclidinium, umeclidinium), PDE4 inhibitors (e.g. roflumilast), riluzole, free radical scavengers (e.g. edaravone), proteasome inhibitors (e.g. bortezomib), complement cascade inhibitors including those directed against C5 (e.g. eculizumab), immunoadsor, antithymocyte globulin, 5-aminosalicylates and their derivatives (e.g. sulfasalazine, balsalazide, mesalamine), anti-integrin agents including those targeting α4β1 and/or α4β7 integrins (e.g. natalizumab, vedolizumab), anti-CD11-α agents (e.g. efalizumab), non-steroidal anti-inflammatory drugs (NSAIDs) including the salicylates (e.g. aspirin), propionic acids (e.g. ibuprofen, naproxen), acetic acids (e.g. indomethacin, diclofenac, etodolac), oxicams (e.g. meloxicam) and fenamates (e.g. mefenamic acid), selective or relatively selective COX-2 inhibitors (e.g. celecoxib, etroxicoxib, valdecoxib and etodolac, meloxicam, nabumetone), colchicine, IL-4 receptor inhibitors (e.g. dupilumab), topical/contact immunotherapy (e.g. diphenylcyclopropenone, squaric acid dibutyl ester), anti-IL-1 receptor therapy (e.g. anakinra), IL-1β inhibitor (e.g. canakinumab), IL-1 neutralising therapy (e.g. rilonacept), chlorambucil, specific antibiotics with immunomodulatory properties and/or ability to modulate NRF2 (e.g. tetracyclines including minocycline, clindamycin, macrolide antibiotics), anti-androgenic therapy (e.g. cyproterone, spironolactone, finasteride), pentoxifylline, ursodeoxycholic acid, obeticholic acid, fibrate, cystic fibrosis transmembrane conductance regulator (CFTR) modulators, VEGF (vascular endothelial growth factor) inhibitors (e.g. bevacizumab, ranibizumab, pegaptanib, aflibercept), pirfenidone, and mizoribine.

Compounds of formula (I) and (XVI) may display one or more of the following desirable properties:

- low $IC_{50}$ values for inhibiting release of cytokines e.g. IL-1β and/or IL-6, from cells;
- low $EC_{50}$ and/or high $E_{max}$ values for activating the NRF2 pathway;
- enhanced efficacy through improved hydrolytic stability of carboxylic acid esters and/or augmented maximum response;
- reduced dose and dosing frequency through improved pharmacokinetics;
- improved oral systemic bioavailability;
- reduced plasma clearance following intravenous dosing;
- improved metabolic stability e.g. as demonstrated by improved stability in plasma and/or hepatocytes;
- augmented cell permeability;
- enhanced aqueous solubility;
- good tolerability, for example, by limiting the flushing and/or gastrointestinal side effects provoked by oral DMF (Hunt T. et al., 2015; WO2014/152494A1, incorporated herein by reference), possibly by reducing or eliminating HCA2 activity;
- low toxicity at the relevant therapeutic dose;
- distinct anti-inflammatory profiles resulting from varied electrophilicities, leading to differential targeting of the cysteine proteome (van der Reest J. et al., 2018) and, therefore, modified effects on gene activation;
- glutathione-sparing actions;
- avoiding the oncometabolite fumaric acid (Kulkarni R. A. et al., 2019).

Abbreviations

Ac acetyl
aq. aqueous
BBFO broadband fluorine observe
BEH ethylene bridged hybrid
CSH charged surface hybrid
d doublet
DAD diode array detector
DBU 1,8-diazabicyclo(5.4.0)undec-7-ene
DCM dichloromethane
DIPEA N,N-diisopropylethylamine
DMAP 4-dimethylaminopyridine
DMF dimethyl fumarate
DMSO dimethyl sulfoxide
EDC 1-ethyl-3-(3-dimethylaminopropyl)carbodiimide
ee enantiomeric excess
Et ethyl
ES+ electrospray
FBS fetal bovine serum
g gram(s)
GSH glutathione
h hour(s)
HATU 1-[bis(dimethylamino)methylene]-1H-1,2,3-triazolo[4,5-b]pyridinium 3-oxide hexafluorophosphate
HPLC high-performance liquid chromatography
IL interleukin
IPA isopropanol
K kelvin
LCMS liquid chromatography-mass spectrometry
m multiplet
M molar concentration/molar mass
m/z mass to charge ratio
mCPBA meta-chloroperoxybenzoic acid
Me methyl
(M)Hz (mega)hertz
min(s) minute(s)
mL millilitre
mm millimetre
mmol millimole
MS mass spectrometry
MTBE methyl tertiary-butyl ether
nm nanometre NMP N-methyl-2-pyrrolidone
NMR nuclear magnetic resonance
PBS phosphate buffered saline
PDA photodiode array
PMB para-methoxybenzyl
4OI 4-octyl itaconic acid
rpm revolutions per minute
RT room temperature
s singlet
t triplet
TBS tert-butyldimethylsilyl
TFA trifluoroacetic acid
THF tetrahydrofuran
Ts tosyl
µL microlitre
µM micromolar
UPLC ultra performance liquid chromatography
wt. weight
° C. degrees centigrade

EXAMPLES

Analytical Equipment

NMR spectra were recorded using a Bruker 400 MHz Avance III spectrometer fitted with a BBFO 5 mm probe, or a Bruker 500 MHz Avance III HD spectrometer equipped with a Bruker 5 mm SmartProbe™. Spectra were measured at 298 K, unless indicated otherwise, and were referenced relative to the solvent resonance. The chemical shifts are reported in parts per million. Data were acquired using Bruker TopSpin software.

UPLC/MS analysis was carried out on a Waters Acquity UPLC system using either a Waters Acquity CSH 018 or BEH 018 column (2.1×30 mm) maintained at a temperature of 40° C. and eluted with a linear acetonitrile gradient appropriate for the lipophilicity of the compound over 3 or 10 minutes at a constant flow rate of 0.77 mL/min. The aqueous portion of the mobile phase was either 0.1% Formic Acid (CSH 018 column) or 10 mM Ammonium Bicarbonate (BEH 018 column). LC-UV chromatograms were recorded using a Waters Acquity PDA detector between 210 and 400 nm. Mass spectra were recorded using a Waters Acquity Qda detector with electrospray ionisation switching between positive and negative ion mode. Sample concentration was adjusted to give adequate UV response.

The following analytical LCMS equipment and methods were used:

LCMS/HPLC Instrument Details

| System | Instrument Name | LC Detector | ELS detector | Mass detector |
|---|---|---|---|---|
| 2 | Agilent LCMS 1200 | G1315C DAD | 380 ELSD | Agilent G6110A |

LCMS/HPLC Method Details

| Method Name | Solvent System | Column | Gradient | UV range | Mass Range | Column Temp. ° C. | Flow Rate ml/min |
|---|---|---|---|---|---|---|---|
| B | A) water + 0.05% TFA B) acetonitrile + 0.05% TFA | Waters X-Bridge C18 (50 mm × 4.6 mm × 3.5 µm) | From 95:5 to 0:100 in 1.6 min, 0:100 for 1.4 min, from 0:100 to 95:5 in 0.05 min, 95:5 for 0.7 min | 190-400 nm | 100-1100 amu | 40 | 2.0 |
| C | A) water + 0.05% TFA B) acetonitrile + 0.05% TFA | Halo C18 (30 mm × 4.6 mm × 2.7 µm) | From 95:5 to 0:100 in 0.8 min, 0:100 for 0.4 min, from 0:100 to 95:5 in 0.01 min, 95:5 for 0.2 min | 190-400 nm | 100-1100 amu | 40 | 3.0 |

Commercial Materials

Dimethyl itaconate was purchased from Sigma-Aldrich (product number: 109533); 4-octyl itaconate was purchased from BOC biosciences (product number: B0001-007866); 4-methyl itaconate was purchased from Apollo Scientific (product number: OR10969).

Intermediate 1—3-((2-(tert-butoxy)-2-oxoethoxy) carbonyl)but-3-enoic acid

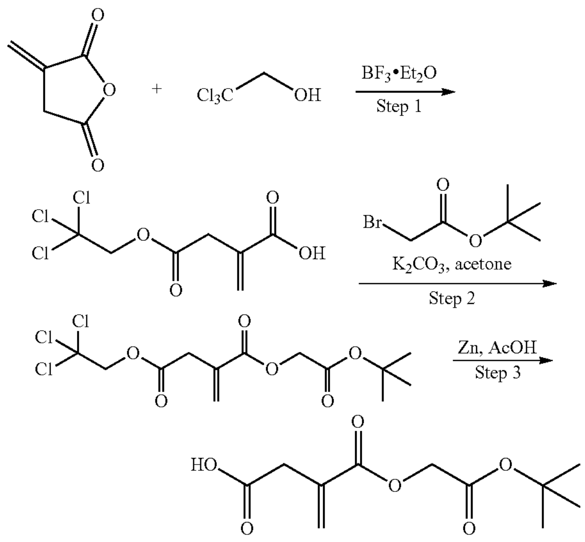

Step 1

Boron trifluoride diethyl etherate (1.43 mL, 11.6 mmol) was added to a mixture of itaconic anhydride (10 g, 89 mmol) and 2,2,2-trichloroethanol (15.4 mL, 161 mmol) under nitrogen at RT. The reaction mixture was heated to 95° C. for 30 mins, then cooled to RT. The residue was treated with sat. aq. $NaHCO_3$ (400 mL) and washed with EtOAc (3×100 mL). The aqueous phase was acidified to pH=2 with concentrated HCl and extracted with EtOAc (3×120 mL). The combined organic layers were dried ($MgSO_4$) and concentrated. The residue was recrystallised from a mixture of toluene and iso-hexane (1:1) (300 mL). The resulting solid was filtered, washed with iso-hexane and dried in vacuo to afford 2-methylene-4-oxo-4-(2,2,2-trichloroethoxy)butanoic acid (13.7 g, 51.3 mmol) as a white crystalline solid. $^1$H NMR (400 MHz, DMSO) δ 12.72 (br, 1H), 6.21 (s, 1H), 5.86 (s, 1H), 4.88 (s, 2H), 3.49 (s, 2H).

Step 2

Potassium carbonate (4.16 g, 30.1 mmol) was added portionwise to a solution of 2-methylene-4-oxo-4-(2,2,2-trichloroethoxy)butanoic acid (7.50 g, 28.7 mmol) in acetone (140 mL) at RT. After 5 min tert-butyl bromoacetate (4.45 mL, 30.1 mmol) was added dropwise. The reaction mixture was stirred at RT for 16 h, then diluted with EtOAc (150 mL) and filtered. The filtrate was concentrated to afford 1-(2-(tert-butoxy)-2-oxoethyl) 4-(2,2,2-trichloroethyl) 2-methylenesuccinate (10.7 g, 28.5 mmol) as a white solid. LCMS: (System 2, Method B) m/z 397.1/399.1 $(M+Na)^+$ (ES+).

Step 3

Zinc (11.2 g, 171 mmol) was added portionwise over 5 min to a solution of 1-(2-(tert-butoxy)-2-oxoethyl) 4-(2,2,2-trichloroethyl) 2-methylenesuccinate (10.7 g, 28.5 mmol) in acetic acid (160 mL). The reaction mixture was stirred at RT for 18 h then diluted with water (100 mL) and EtOAc (300 mL). The mixture was carefully decanted and the phases were separated. The aqueous phase was extracted with EtOAc (3×200 mL). The combined organic extracts were washed with brine (3×150 mL), dried ($Na_2SO_4$) and concentrated to afford 3-((2-(tert-butoxy)-2-oxoethoxy)carbonyl)but-3-enoic acid as a colourless solid (6.07 g). An analytically pure sample was obtained by recrystallisation of a small sample (300 mg) from toluene and isohexane (1:1). LCMS: (System 2, Method B) m/z 267.3 $(M+Na)^+$ (ES+). $^1$H NMR (400 MHz, DMSO) δ 12.34 (br, 1H), 6.25 (d, J=1.3 Hz, 1H), 5.89 (d, J=1.3 Hz, 1H), 4.61 (s, 2H), 3.29 (s, 2H), 1.41 (s, 9H).

Intermediate 2—5-chloro-2,3-dihydro-1H-inden-2-ol

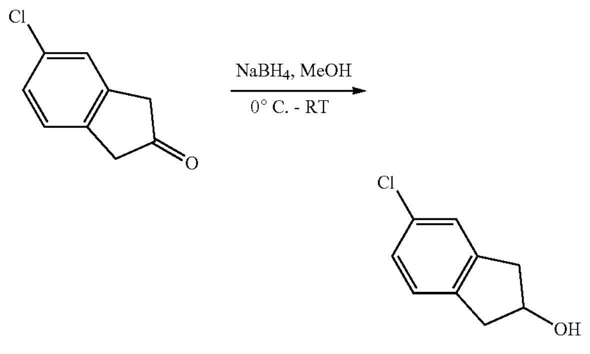

To a solution of 5-chloro-1,3-dihydro-2H-inden-2-one (400 mg, 2.40 mmol) in MeOH (12 mL) was added sodium borohydride (182 mg, 4.80 mmol) at 0° C., and the mixture was stirred at room temperature for 1 h. The mixture was concentrated under reduced pressure to remove the solvent, the residue was quenched with $H_2O$ (10 mL) and the resulting mixture was extracted with EtOAc (2×20 mL). The combined organic phases were washed with brine, dried over $Na_2SO_4$ and filtered. The filtrate was concentrated under reduced pressure at 30° C. to give 5-chloro-2,3-dihydro-1H-inden-2-ol (400 mg, 2.37 mmol, 98%, racemic) as a yellow oil. LCMS: (System 2, Method C) m/z 151.2 $(M-OH)^+$ $(ES^+)$.

Intermediate 3—4,6-dichloro-2,3-dihydro-1H-inden-1-ol Enantiomer 1 and Intermediate 4-4,6-dichloro-2,3-dihydro-1H-inden-1-ol Enantiomer 2

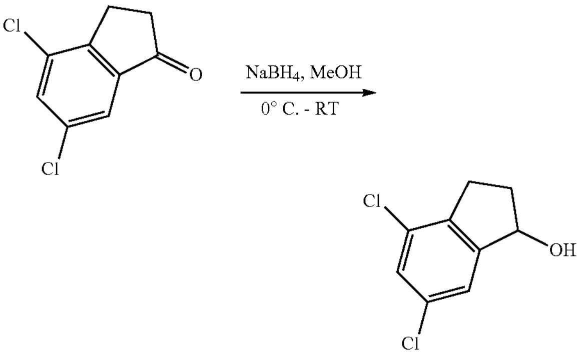

To a solution of 4,6-dichloro-2,3-dihydro-1H-inden-1-one (1 g, 4.97 mmol) in MeOH (30 mL) at 0° C. was added sodium borohydride (378 mg, 9.94 mmol), and the mixture was allowed to stir at room temperature for 1 h. The mixture was concentrated under reduced pressure to remove the solvent and the residue was quenched with $H_2O$ (30 mL) and extracted with EtOAc (2×40 mL). The separated organic phases were washed with brine, dried over $Na_2SO_4$ and filtered. The filtrate was concentrated under reduced pressure at 30° C., and the residue was purified by flash column chromatography (25 g $SiO_2$, 0-20% MTBE/petroleum ether) to give 4,6-dichloro-2,3-dihydro-1H-inden-1-ol (930 mg, 4.58 mmol, 92%) as a yellow oil. LCMS: (System 2, Method C) m/z 185.3/187.3 $(M-OH)^+$ $(ES^+)$.

Racemic 4,6-dichloro-2,3-dihydro-1H-inden-1-ol (930 mg, 4.6 mmol) was resolved using chiral SFC (Column: CHIRALCEL OD-5, 5 μm 30×250 mm; Column temperature: 35° C.; Flow Rate: 45 mL/min; solvent system: 25% $MeCN/CO_2$; collection wavelength: 215 nm). The SFC fractions were concentrated under reduced pressure at 35° C. to remove acetonitrile to give 4,6-dichloro-2,3-dihydro-1H-inden-1-ol Enantiomer 1 as the first eluting peak (400 mg, 2.0 mmol, 43%) and 4,6-dichloro-2,3-dihydro-1H-inden-1-ol Enantiomer 2 as the second eluting peak (450 mg, 2.2 mmol, 48%). Chiral SFC analysis (Column: CHIRALCEL OD-3 3 μm 4.6×100 mm; Column temperature: 35° C.; Flow rate: 2 mL/min; Solvent system: 25% $MeCN/CO_2$; Collection wavelength: 200-400 nm): 4,6-dichloro-2,3-dihydro-1H-inden-1-ol Enantiomer 1: Rt=1.808 min, 100% ee; 4,6-dichloro-2,3-dihydro-1H-inden-1-ol Enantiomer 2: Rt=2.407 min, 98.3% ee.

Intermediate 5—5,6-dichloro-2,3-dihydro-1H-inden-2-ol

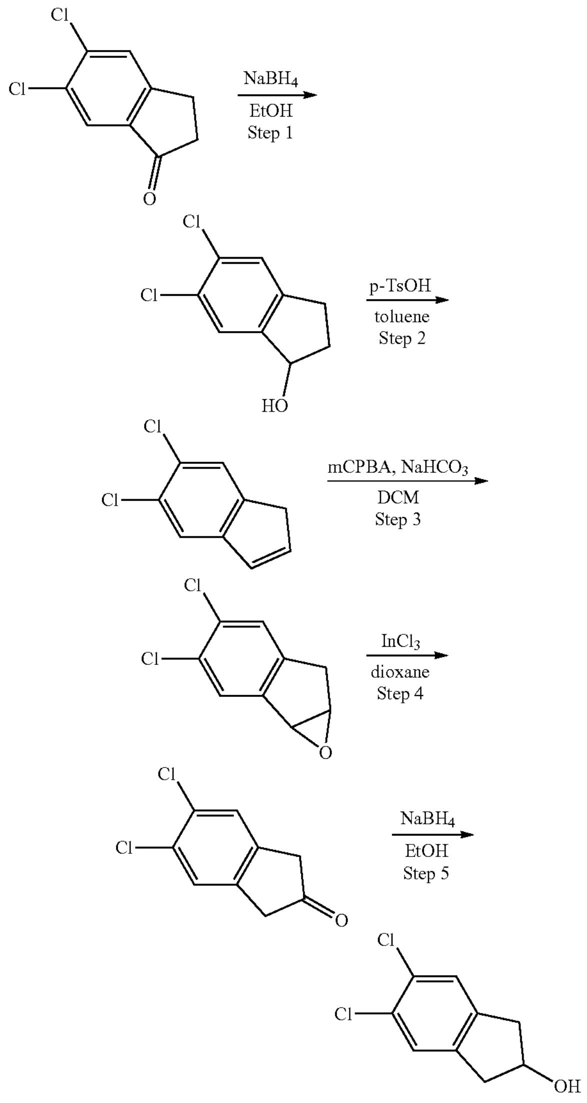

Step 1

To a solution of 5,6-dichloro-2,3-dihydro-1H-inden-1-one (15.0 g, 74.6 mmol) in ethanol (298 mL) was added $NaBH_4$ (2.82 g, 74.6 mmol) in portions, and the resulting mixture was stirred at room temperature overnight. The reaction mixture was concentrated under reduced pressure at 40° C. to give a residue which was poured into ice-water and extracted with EtOAc. The combined organic phase was washed with brine, dried over $Na_2SO_4$ and filtered. The filtrate was concentrated under reduced pressure at 40° C., and the residue was purified by flash column chromatography (120 g $SiO_2$, 25% EtOAc/petroleum ether) to give 5,6-dichloro-2,3-dihydro-1H-inden-1-ol (13.9 g, 68.4 mmol, 92%) as a white solid. LCMS: (System 2, Method C) m/z 185.2/187.2 $(M-OH)^+$ $(ES^+)$.

Step 2

To a solution of 5,6-dichloro-2,3-dihydro-1H-inden-1-ol (11 g, 54.2 mmol) in toluene (217 mL) was added p-toluenesulfonic acid (1.03 g, 5.41 mmol) at room temperature, and the resulting mixture was stirred at 130° C. using a Dean and Stark water trap for 2 h. The mixture was washed with saturated aqueous $NaHCO_3$ solution, dried over $Na_2SO_4$ and filtered. The filtrate was concentrated under reduced pressure at 45° C., and the residue was purified by flash column chromatography (80 g $SiO_2$, 5% EtOAc/petroleum ether) to give 5,6-dichloro-1H-indene (9.50 g, 51.3 mmol, 95%) as a white solid. No ionisation observed under LCMS method conditions. Used directly in the next step.

Step 3

To a solution of 5,6-dichloro-1H-indene (9.50 g, 51.3 mmol) in DCM (570 mL) was added m-CPBA (13.30 g, 77.1 mmol) and $NaHCO_3$ (6.50 g, 77.4 mmol), and the resulting mixture was stirred at room temperature overnight. The mixture was added to water (1000 mL) and extracted with DCM (3×500 mL). The combined organic phases were washed with brine, dried over $Na_2SO_4$ and filtered. The filtrate was concentrated under reduced pressure at 40° C., and the residue was purified by flash column chromatography (80 g $SiO_2$, 20% EtOAc/petroleum ether) to give 3,4-dichloro-1a,6a-dihydro-6H-indeno[1,2-b]oxirene (7.10 g, 35.3 mmol, 69%) as a yellow solid. No ionisation observed under LCMS method conditions. Used directly in the next step.

Step 4

To a solution of 3,4-dichloro-1a,6a-dihydro-6H-indeno[1,2-b]oxirene (7.10 g, 35.3 mmol) in dioxane (770 mL) was added $InCl_3$ (7.82 g, 35.4 mmol) at room temperature, and the resulting mixture was stirred at 60° C. for 3 h. The mixture was quenched with water (1000 mL) and extracted with DCM (3×100 mL). The combined organic phases were washed with brine, dried over $Na_2SO_4$ and filtered. The filtrate was concentrated under reduced pressure at 40° C., and the residue was purified by flash column chromatography (80 g $SiO_2$, 30% EtOAc/petroleum ether) to give 5,6-dichloro-1,3-dihydro-2H-inden-2-one (4.40 g, 21.9 mmol, 62%) as a yellow solid. No ionisation observed under LCMS method conditions. Used directly in the next step.

Step 5

To a solution of 5,6-dichloro-1,3-dihydro-2H-inden-2-one (250 mg, 1.24 mmol) in EtOH (5 mL) was added $NaBH_4$ (50 mg, 1.32 mmol) at room temperature, and the resulting mixture was stirred at room temperature for 3 h. The mixture was quenched with ice-water and extracted with DCM (2×20 mL). The combined organic phases were washed with brine, dried over $Na_2SO_4$ and filtered. The filtrate was concentrated under reduced pressure at 40° C., and the residue was purified by flash column chromatography (8 g $SiO_2$, 30% EtOAc/petroleum ether) to give 5,6-dichloro-2,3-dihydro-1H-inden-2-ol (191 mg, 0.94 mmol, 76%) as a white solid. LCMS: (System 2, Method C) m/z 185.2/187.2 $(M-OH)^+$ $(ES^+)$.

Intermediate 6—3-((2-oxo-2-(2,2,2-trichloroethoxy)ethoxy)carbonyl)but-3-enoic acid

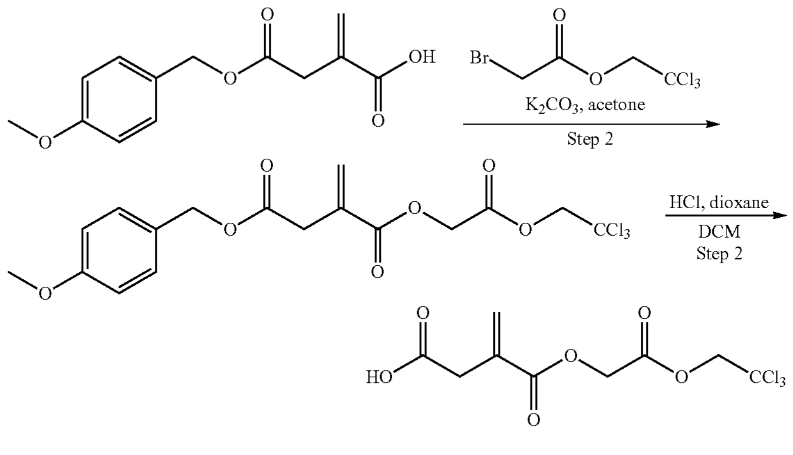

Step 1

A mixture of 4-((4-methoxybenzyl)oxy)-2-methylene-4-oxobutanoic acid (2.50 g, 9.99 mmol), 2,2,2-trichloroethyl 2-bromoacetate (2.70 g, 9.99 mmol) and potassium carbonate (1.52 g, 11.0 mmol) in acetone (50 mL) was stirred at room temperature for 16 h. The mixture was then filtered, and the filtrate was concentrated under reduced pressure at 30° C., and the residue was purified by flash column chromatography (40 g $SiO_2$, 0-15% MTBE/petroleum ether) to give 4-(4-methoxybenzyl) 1-(2-oxo-2-(2,2,2-trichloroethoxy)ethyl) 2-methylenesuccinate (4.30 g, 9.78 mmol, 98%) as a colorless oil. LCMS: (System 2, Method C) m/z 461.0/463.0 $(M+Na)^+$ $(ES^+)$.

Step 2

A mixture of 4-(4-methoxybenzyl) 1-(2-oxo-2-(2,2,2-trichloroethoxy)ethyl) 2-methylenesuccinate (4.30 g, 9.78 mmol) in HCl solution in 1,4-dioxane (4 M, 10 mL) and DCM (10 mL) was stirred at room temperature overnight. The mixture was concentrated under reduced pressure at 30° C. and the residue was purified by reversed phase column chromatography (120 g C18 silica; flow rate: 40 mL/min; 40-60% MeCN/10 mM HCl/water; collection wavelength: 214 nm). The collected fractions were concentrated under reduced pressure at 40° C. to remove MeCN, and the residue was lyophilized to give 3-((2-oxo-2-(2,2,2-trichloroethoxy)ethoxy)carbonyl)but-3-enoic acid (2.50 g, 7.82 mmol, 80%) as a colorless oil. LCMS: (System 2, Method B) m/z 341.0/343.0 $(M+Na)^+$ $(ES^+)$. $^1H$ NMR (400 MHz, DMSO-$d_6$) δ: 12.39 (br, 1H), 6.29 (d, J=1.2 Hz, 1H), 5.93 (d, J=0.9 Hz, 1H), 4.97 (s, 2H), 4.95 (s, 2H), 3.30 (s, 2H).

Intermediate 7—5,6-dichloro-2,3-dihydro-1H-inden-1-ol Enantiomer 1 and Intermediate 8-5,6-dichloro-2,3-dihydro-1H-inden-1-ol Enantiomer 2

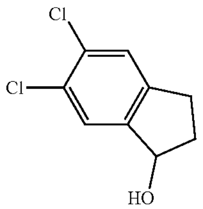 [SMILES: OC1CCc2cc(Cl)c(Cl)cc21]

Racemic 5,6-dichloro-2,3-dihydro-1H-inden-1-ol (Intermediate 5 Step 1, 1.0 g, 4.92 mmol) was resolved using chiral SFC (Column: CHIRALCEL OJ-5, 5 μm 30×250 mm; Column temperature: 35° C.; Flow Rate: 45 mL/min; solvent system: 15% $MeOH/CO_2$; collection wavelength: 215 nm). The SFC fractions were concentrated under reduced pressure at 40° C. to remove MeOH to give 5,6-dichloro-2,3-dihydro-1H-inden-1-ol Enantiomer 1 as the first eluting peak (480 mg, 2.4 mmol, 48%) and 5,6-dichloro-2,3-dihydro-1H-inden-1-ol Enantiomer 2 as the second eluting peak (470 mg, 2.3 mmol, 47%). Chiral SFC analysis (Column: CHIRALCEL OJ-3 3 μm 4.6×100 mm; Column temperature: 35° C.; Flow rate: 2 mL/min; Solvent system: 15% $MeOH/CO_2$; Collection wavelength: 200-400 nm): 5,6-dichloro-2,3-dihydro-1H-inden-1-ol Enantiomer 1: Rt=1.502 min, 100% ee; 5,6-dichloro-2,3-dihydro-1H-inden-1-ol Enantiomer 2: Rt=1.844 min, 99.0% ee.

Intermediate 9—5-chloro-2-methyl-2,3-dihydro-1H-inden-2-ol

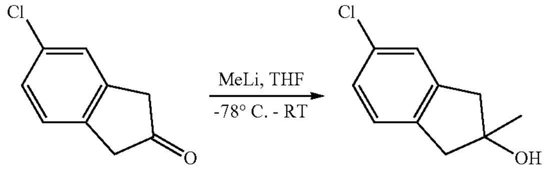

To a solution of 5-chloro-1,3-dihydro-2H-inden-2-one (4.00 g, 24.0 mmol) in THF (80 mL) at −78° C. was slowly added a solution of methyllithium in diethyl ether (1.6 M, 18.0 mL, 28.8 mmol) dropwise, and the mixture was stirred at room temperature overnight. The reaction mixture was quenched with saturated aqueous $NH_4Cl$ solution (50 mL), the phases were separated and the aqueous layer was extracted with MTBE (2×50 mL). The combined organic layers were washed by brine, dried over $Na_2SO_4$, filtered, and concentrated under reduced pressure at 30° C. The residue was purified by flash column chromatography (40 g $SiO_2$, 0-15% MTBE/petroleum ether) to give 5-chloro-2-methyl-2,3-dihydro-1H-inden-2-ol (690 mg, 3.8 mmol, 16%) as a colorless oil. LCMS: (System 2, Method C) m/z 165.4/167.2 $(M-OH)^+$ $(ES^+)$.

Intermediate 10—5,7-dichloro-2,3-dihydro-1H-inden-1-ol Enantiomer 1 and Intermediate 11-5,7-dichloro-2,3-dihydro-1H-inden-1-ol Enantiomer 2

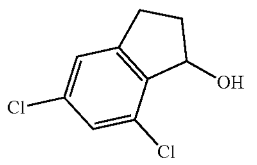 [SMILES: OC1CCc2cc(Cl)cc(Cl)c21]

Racemic 5,7-dichloro-2,3-dihydro-1H-inden-1-ol was prepared by an analogous method as that used in the preparation of Intermediate 3 and Intermediate 4. LCMS: (System 2, Method C) m/z 185.0/187.2 $(M-OH)^+$ $(ES^+)$.

Racemic 5,7-dichloro-2,3-dihydro-1H-inden-1-ol (930 mg, 4.6 mmol) was resolved using chiral SFC (Column: CHIRALCEL OJ-5, 5 μm 30×250 mm; Column temperature: 35° C.; Flow Rate: 45 mL/min; solvent system: 15% IPA/$CO_2$; collection wavelength: 215 nm). The SFC fractions were concentrated under reduced pressure at 35° C. to remove IPA to give 5,7-dichloro-2,3-dihydro-1H-inden-1-ol Enantiomer 1 as the first eluting peak (450 mg, 2.2 mmol, 48%) and 5,7-dichloro-2,3-dihydro-1H-inden-1-ol Enantiomer 2 as the second eluting peak (500 mg, 2.5 mmol, 54%). Chiral SFC analysis (Column: CHIRALCEL OJ-3 3 μm 4.6×100 mm; Column temperature: 35° C.; Flow rate: 2 mL/min; Solvent system: 15% IPA/$CO_2$; Collection wavelength: 200-400 nm): 5,7-dichloro-2,3-dihydro-1H-inden-1-ol Enantiomer 1: Rt=1.184 min, 100% ee; 5,7-dichloro-2,3-dihydro-1H-inden-1-ol Enantiomer 2: Rt=1.440 min, 98.6% ee.

Intermediate 12—6,8-dichloro-1,2,3,4-tetrahydronaphthalen-2-ol Enantiomer 1 and Intermediate 13—6,8-dichloro-1,2,3,4-tetrahydronaphthalen-2-ol Enantiomer 2

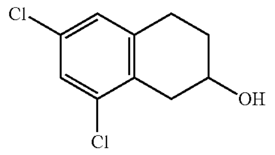 [SMILES: OC1CCc2cc(Cl)cc(Cl)c2C1]

Racemic 6,8-dichloro-1,2,3,4-tetrahydronaphthalen-2-ol was prepared by an analogous method as that used in the preparation of Intermediate 3 and Intermediate 4. LCMS: (System 2, Method C) m/z 199.2/201.2 $(M-OH)^+$ $(ES^+)$.

Racemic 6,8-dichloro-1,2,3,4-tetrahydronaphthalen-2-ol (880 mg, 4.95 mmol) was resolved using chiral SFC (Column: CHIRALPAK AD-5, 5 μm 30×250 mm; Column temperature: 35° C.; Flow Rate: 45 mL/min; solvent system: 15% MeOH/$CO_2$; collection wavelength: 214 nm). The SFC fractions were concentrated under reduced pressure at 35° C. to remove MeOH to give 6,8-dichloro-1,2,3,4-tetrahydronaphthalen-2-ol Enantiomer 1 as the first eluting peak (380 mg, 1.8 mmol, 43%) and 6,8-dichloro-1,2,3,4-tetrahydronaphthalen-2-ol Enantiomer 2 as the second eluting peak (410 mg, 1.9 mmol, 46%). Chiral SFC analysis (Column: CHIRALPAK AD-3 3 μm 4.6×100 mm; Column temperature: 35° C.; Flow rate: 2 mL/min; Solvent system: 25% MeOH/$CO_2$; Collection wavelength: 200-400 nm): 6,8-dichloro-1,2,3,4-tetrahydronaphthalen-2-ol Enantiomer 1: Rt=1.674 min, 100% ee; 6,8-dichloro-1,2,3,4-tetrahydronaphthalen-2-ol Enantiomer 2: Rt=2.103 min, 98.9% ee.

Intermediate 14—5-bromo-6-methoxy-2,3-dihydro-1H-inden-1-ol Enantiomer 1 and Intermediate 15—5-bromo-6-methoxy-2,3-dihydro-1H-inden-1-ol Enantiomer 2

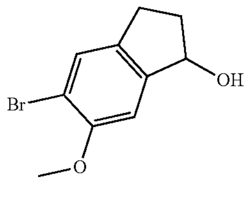

Racemic 5-bromo-6-methoxy-2,3-dihydro-1H-inden-1-ol was prepared by an analogous method as that used in the preparation of Intermediate 3 and Intermediate 4. LCMS: (System 2, Method C) m/z 225.1/227.1 $(M-OH)^+$ $(ES^+)$.

Racemic 5-bromo-6-methoxy-2,3-dihydro-1H-inden-1-ol (1.0 g, 4.13 mmol) was resolved using chiral SFC (Column: CHIRALCEL OJ-5, 5 μm 30×250 mm; Column temperature: 35° C.; Flow Rate: 45 mL/min; solvent system: 15% MeOH/$CO_2$; collection wavelength: 215 nm). The SFC fractions were concentrated under reduced pressure at 35° C. to remove MeOH to give 5-bromo-6-methoxy-2,3-dihydro-1H-inden-1-ol Enantiomer 1 as the first eluting peak (480 mg, 2.0 mmol, 48%) and 5-bromo-6-methoxy-2,3-dihydro-1H-inden-1-ol Enantiomer 2 as the second eluting peak (500 mg, 2.1 mmol, 50%). Chiral SFC analysis (Column: CHIRALCEL OJ-3 3 μm 4.6×100 mm; Column temperature: 35° C.; Flow rate: 2 mL/min; Solvent system: 15% MeOH/$CO_2$; Collection wavelength: 200-400 nm): 5-bromo-6-methoxy-2,3-dihydro-1H-inden-1-ol Enantiomer 1: Rt=1.572 min, 100% ee; 5-bromo-6-methoxy-2,3-dihydro-1H-inden-1-ol Enantiomer 2: Rt=2.154 min, 100% ee.

Intermediate 16—3-((3-oxo-3-(2,2,2-trichloroethoxy)propoxy)carbonyl)but-3-enoic acid

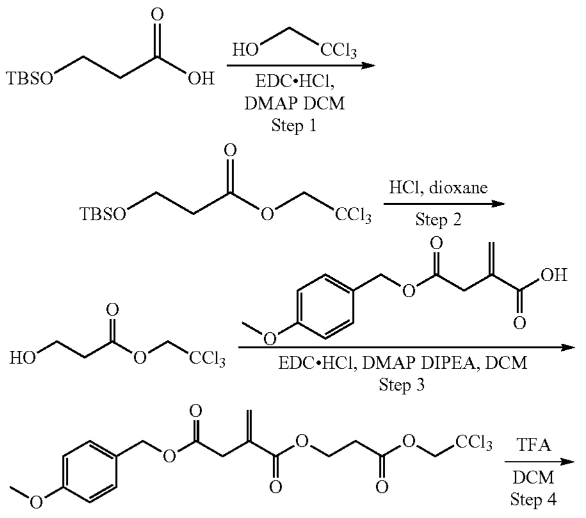

-continued

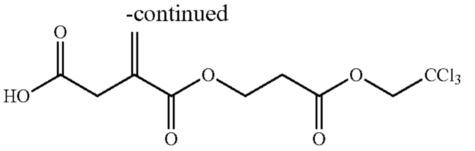

Step 1

To a solution of 3-((tert-butyldimethylsilyl)oxy)propanoic acid (1.9 g, 9.3 mmol), 2,2,2-trichloroethan-1-ol (1.27 g, 8.5 mmol) and DMAP (1.56 g, 12.8 mmol) in DCM (47 mL) at 0° C. was added EDC·HCl (2.45 g, 12.8 mmol) and the resulting pale yellow mixture was stirred at room temperature for 16 h. The mixture was quenched with saturated aqueous $NH_4Cl$ solution (30 mL), the phases were separated, and the aqueous phase was extracted with EtOAc (2×40 mL). The separated organic phase was washed with brine, dried over $Na_2SO_4$ and filtered. The filtrate was concentrated under reduced pressure at 35° C., and the residue was purified by flash column chromatography (40 g silica, 0-9% MTBE/petroleum ether) to give 2,2,2-trichloroethyl 3-((tert-butyldimethylsilyl)oxy)propanoate (800 mg, 2.38 mmol, 25%) as a colorless oil. $^1H$ NMR (400 MHz, $CDCl_3$) δ: 4.75 (s, 2H), 3.95 (t, J=6.2 Hz, 2H), 2.68 (t, J=6.3 Hz, 2H), 0.87 (s, 9H), 0.06 (s, 6H).

Step 2

A solution of 2,2,2-trichloroethyl 3-((tert-butyldimethylsilyl)oxy)propanoate (800 mg, 2.38 mmol) in HCl solution in 1,4-dioxane (4 M, 10 mL) was stirred at room temperature for 16 h. The mixture was concentrated under reduced pressure at 30° C. and the residue was purified by flash column chromatography (40 g silica, 0-10% MTBE/petroleum ether) to give 2,2,2-trichloroethyl 3-hydroxypropanoate (400 mg, 1.81 mmol, 75%) as a pale yellow oil. LCMS: (System 2, Method C) m/z 221.2/223.2 $(M+H)^+$ $(ES^+)$.

Step 3

To a solution of 2,2,2-trichloroethyl 3-hydroxypropanoate (1.00 g, 4.52 mmol), 4-(4-methoxybenzyloxy)-2-methylene-4-oxobutanoic acid (1.13 g, 4.52 mmol), DMAP (441 mg, 3.62 mmol) and EDC·HCl (1.30 g, 6.78 mmol) in DCM (23 mL) at 0° C. was added DIPEA (1.75 g, 13.56 mmol), and the resulting pale-yellow mixture was stirred at room temperature for 2 h. The mixture was quenched with dilute aqueous HCl (0.5 M) to pH=6, the phases were separated and the aqueous phase was extracted with DCM (2×25 mL). The combined organic layers were washed with brine, dried over $Na_2SO_4$ and filtered. The filtrate was concentrated under reduced pressure at 30° C., and the residue was purified by flash column chromatography (25 g silica, 0-10% MTBE/petroleum ether) to give 4-(4-methoxybenzyl) 1-(3-oxo-3-(2,2,2-trichloroethoxy)propyl) 2-methylenesuccinate (890 mg, 1.96 mmol, 43%) as a yellow oil LCMS: (System 2, Method C) m/z 475.0/477.0/479.0 $(M+Na)^+$ $(ES^+)$.

Step 4

A solution of 4-(4-methoxybenzyl) 1-(3-oxo-3-(2,2,2-trichloroethoxy)propyl) 2-methylenesuccinate (890 mg, 1.96 mmol) in TFA (5 mL) in DCM (10 mL) was stirred at room temperature for 2 h. The mixture was filtered, the filtrate was concentrated under reduced pressure at 25° C. and the residue was purified by reversed phase column chromatography (40 g C18 silica; flow rate: 60 mL/min; 60-80% MeCN/10 mM formic acid/water; collection wavelength: 214 nm). The collected fractions were concentrated under reduced pressure at 25° C. to remove MeCN, and the residue was lyophilized to give 3-((3-oxo-3-(2,2,2-trichloroethoxy)propoxy)carbonyl)but-3-enoic acid (500 mg, 1.50 mmol, 76%) as a yellow oil. LCMS: (System 2, Method C) m/z 354.9/356.9/358.9 $(M+Na)^+$ $(ES^+)$.

Intermediate 17—4-bromo-6-fluoro-2,3-dihydro-1H-inden-1-ol Enantiomer 1 and Intermediate 18—4-bromo-6-fluoro-2,3-dihydro-1H-inden-1-ol Enantiomer 2

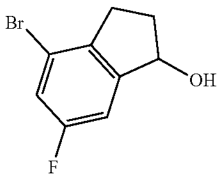

Racemic 4-bromo-6-fluoro-2,3-dihydro-1H-inden-1-ol was prepared by an analogous method as that used in the preparation of Intermediate 3 and Intermediate 4. LCMS: (System 2, Method C) m/z 213.0/215.2 $(M-OH)^+$ $(ES^+)$.

Racemic 4-bromo-6-fluoro-2,3-dihydro-1H-inden-1-ol (1.9 g, 8.26 mmol) was resolved using chiral SFC (Column: CHIRALPAK AY-5, 5 μm 30×250 mm; Column temperature: 35° C.; Flow Rate: 40 mL/min; solvent system: 10% $IPA/CO_2$; collection wavelength: 215 nm). The SFC fractions were concentrated under reduced pressure at 40° C. to remove IPA to give 4-bromo-6-fluoro-2,3-dihydro-1H-inden-1-ol Enantiomer 1 as the first eluting peak (940 mg, 4.07 mmol, 50%) and 4-bromo-6-fluoro-2,3-dihydro-1H-inden-1-ol Enantiomer 2 as the second eluting peak (950 mg, 4.11 mmol, 50%). Chiral SFC analysis (Column: CHIRALPAK AY-3 3 μm 4.6×100 mm; Column temperature: 35° C.; Flow rate: 2.5 mL/min; Solvent system: 10% $IPA/CO_2$; Collection wavelength: 214 nm): 4-bromo-6-fluoro-2,3-dihydro-1H-inden-1-ol Enantiomer 1: Rt=1.133 min, 100% ee; 4-bromo-6-fluoro-2,3-dihydro-1H-inden-1-ol Enantiomer 2: Rt=1.357 min, 100% ee.

Intermediate 19—5-(trifluoromethyl)-2,3-dihydro-1H-inden-1-ol

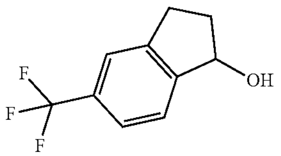 [SMILES: OC1CCc2cc(C(F)(F)F)ccc21]

Racemic 5-(trifluoromethyl)-2,3-dihydro-1H-inden-1-ol was prepared by an analogous method as that used in the preparation of Intermediate 3 and Intermediate 4. $^1H$ NMR (400 MHz, $CDCl_3$) δ: 7.51 (s, 3H), 5.28 (q, J=6.6 Hz, 1H), 3.16-3.03 (m, 1H), 2.94-2.80 (m, 1H), 2.63-2.49 (m, 1H), 2.06-1.93 (m, 1H), 1.80 (d, J=6.9 Hz, 1H).

Intermediate 20—6-(trifluoromethoxy)-2,3-dihydro-1H-inden-1-ol

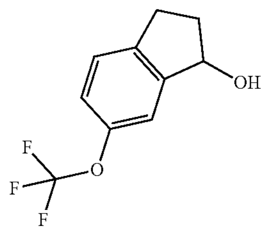 [SMILES: OC1CCc2ccc(OC(F)(F)F)cc21]

Racemic 6-(trifluoromethoxy)-2,3-dihydro-1H-inden-1-ol was prepared by an analogous method as that used in the preparation of Intermediate 3 and Intermediate 4. LCMS: (System 2, Method C) m/z 201.2 $(M-OH)^+$ $(ES^+)$.

Intermediate 21—4-chloro-6-fluoro-2,3-dihydro-1H-inden-1-ol Enantiomer 1 and Intermediate 22—4-chloro-6-fluoro-2,3-dihydro-1H-inden-1-ol Enantiomer 2

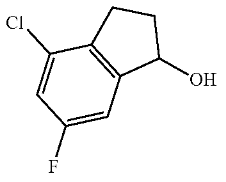 [SMILES: OC1CCc2c(Cl)cc(F)cc21]

Racemic 4-chloro-6-fluoro-2,3-dihydro-1H-inden-1-ol was prepared by an analogous method as that used in the preparation of Intermediate 3 and Intermediate 4. $^1H$ NMR (400 MHz, DMSO-d6) δ: 7.26 (dd, J=9.0, 2.4 Hz, 1H), 7.10 (d, J=8.4, 2.4 Hz, 1H), 5.52 (d, J=6.0 Hz, 1H), 5.08 (q, J=6.6 Hz, 1H), 2.95-2.82 (m, 1H), 2.76-2.61 (m, 1H), 2.45-2.33 (m, 1H), 1.89-1.75 (m, 1H).

Racemic 4-chloro-6-fluoro-2,3-dihydro-1H-inden-1-ol (1.79 g, 4.60 mmol) was resolved using chiral SFC (Column: CHIRALPAK AY-5, 5 μm 30×250 mm; Column temperature: 35° C.; Flow Rate: 15 mL/min; solvent system: 15% $IPA/CO_2$; collection wavelength: 214 nm). The SFC fractions were concentrated under reduced pressure at 35° C. to remove IPA to give 4-chloro-6-fluoro-2,3-dihydro-1H-inden-1-ol Enantiomer 1 as the first eluting peak (700 mg, 3.75 mmol, 39%) and 4-chloro-6-fluoro-2,3-dihydro-1H-inden-1-ol Enantiomer 2 as the second eluting peak (730 mg, 3.91 mmol, 40%). Chiral SFC analysis (Column: CHIRALPAK AY-3 3 μm 4.6×100 mm; Column temperature: 35° C.; Flow rate: 2 mL/min; Solvent system: 15% $IPA/CO_2$; Collection wavelength: 200-400 nm): 4-chloro-6-fluoro-2,3-dihydro-1H-inden-1-ol Enantiomer 1: Rt=1.026 min, 100% ee; 4-chloro-6-fluoro-2,3-dihydro-1H-inden-1-ol Enantiomer 2: Rt=1.219 min, 100% ee.

Intermediate 23—5,6-dichloro-2-methyl-2,3-dihydro-1H-inden-2-ol

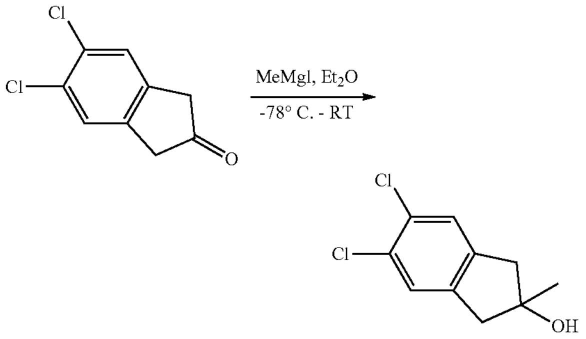

To a solution of 5-chloro-1H-inden-2(3H)-one (Intermediate 5 Step 4, 3.20 g, 15.92 mmol) in diethyl ether (60 mL) at −78° C. was slowly added a solution of methylmagnesium iodide in diethyl ether (3 M, 8.0 mL, 24.0 mmol) dropwise, and the resulting mixture was stirred at room temperature for 4 h. The reaction mixture was quenched with saturated aqueous $NH_4Cl$ solution (40 mL), and extracted with MTBE (2×50 mL). The combined organic layers were washed with brine, dried over $Na_2SO_4$, filtered and concentrated under reduced pressure at 30° C. The residue was purified by flash column chromatography (40 g silica, 0-13% MTBE/petroleum ether) to give 5,6-dichloro-2-methyl-2,3-dihydro-1H-inden-2-ol (660 mg, 3.04 mmol, 19%) as a pale-yellow oil. LCMS: (System 2, Method C) m/z 199.2/201.2 $(M-OH)^+$ $(ES^+)$.

Intermediate 24—3-((2,2,2-trichloroethoxy)carbonyl)but-3-enoic acid

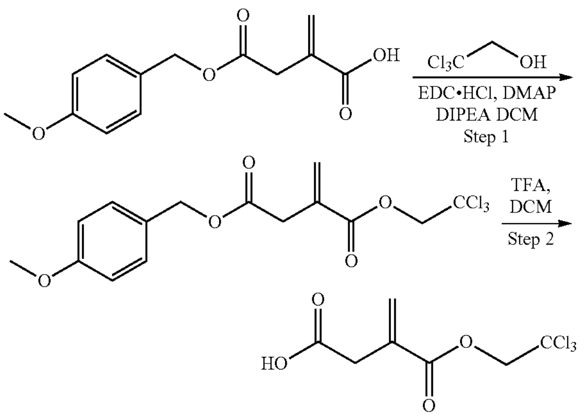

Step 1

To a solution of 4-((4-methoxybenzyl)oxy)-2-methylene-4-oxobutanoic acid (30.0 g, 120 mmol), 2,2,2-trichloroethan-1-ol (19.7 g, 132 mmol), DMAP (11.7 g, 96 mmol) and DIPEA (46.4 g, 360 mmol) in DCM (500 mL) at 0° C. was added EDC·HCl (34.6 g, 180 mmol), and the resulting pale-yellow mixture was stirred at room temperature overnight. The mixture was quenched with dilute aqueous HCl (0.5 M), the phases were separated and the aqueous layer was extracted with DCM (3×500 mL). The combined organic phases were washed with brine, dried over $Na_2SO_4$ and filtered. The filtrate was concentrated under reduced pressure at 30° C., and the residue was purified by flash column chromatography (120 g silica, 0-20% MTBE/petroleum ether) to give 4-(4-methoxybenzyl) 1-(2,2,2-trichloroethyl) 2-methylenesuccinate (35 g, 91.7 mmol, 76%) as a colorless oil. LCMS: (System 2, Method C) m/z 402.8/404.8 $(M+Na)^+$ $(ES^+)$.

Step 2

A solution of 4-(4-methoxybenzyl) 1-(2,2,2-trichloroethyl) 2-methylenesuccinate (35.0 g, 91.7 mmol) in TFA (40 mL) and DCM (80 mL) was stirred at room temperature for 16 h. The mixture was concentrated under reduced pressure at 30° C. and the residue was purified by reversed phase column chromatography (330 g C18 silica; flow rate: 60 mL/min; 60-80% MeCN/10 mM formic acid/water; collection wavelength: 214 nm). The collected fractions were concentrated under reduced pressure at 30° C. to remove MeCN, and the residue was lyophilized to give 3-((2,2,2-trichloroethoxy)carbonyl)but-3-enoic acid (23.0 g, 88.0 mmol, 96%) as a colorless oil. LCMS: (System 2, Method C) m/z 282.8/284.8 $(M+Na)^+$ $(ES^+)$.

Intermediate 25—4-((4,6-dichloro-2,3-dihydro-1H-inden-1-yl)oxy)-2-methylene-4-oxobutanoic acid Enantiomer 1

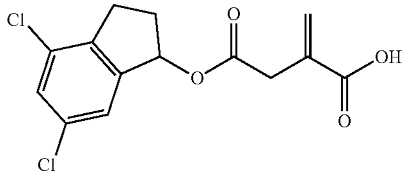 [SMILES: C=C(CC(=O)OC1CCc2c(Cl)cc(Cl)cc21)C(=O)O]

Prepared by an analogous method to Example 5 starting from 4,6-dichloro-2,3-dihydro-1H-inden-1-ol Enantiomer 1 (Intermediate 3, 1.00 g, 4.92 mmol) and 3-((2,2,2-trichloroethoxy)carbonyl)but-3-enoic acid (Intermediate 24, 1.67 g, 6.40 mmol). The crude product was purified by reversed phase column chromatography (330 g C18 silica; flow rate: 60 mL/min; 60-80% MeCN/10 mM formic acid/water; collection wavelength: 214 nm). The collected fractions were concentrated under reduced pressure at 30° C. to remove MeCN, and the residue was lyophilized to give 4-((4,6-dichloro-2,3-dihydro-1H-inden-1-yl)oxy)-2-methylene-4-oxobutanoic acid Enantiomer 1 (680 mg, 2.16 mmol) as a white solid. LCMS: (System 2, Method C) m/z 337.0/339.0 $(M+Na)^+$ $(ES^+)$.

Intermediate 26—4-methoxybenzyl (S)-4,4,4-trifluoro-3-hydroxybutanoate and Intermediate 27—4-methoxybenzyl (R)-4,4,4-trifluoro-3-hydroxybutanoate

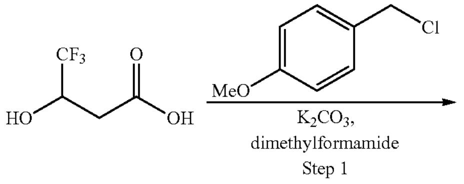

-continued

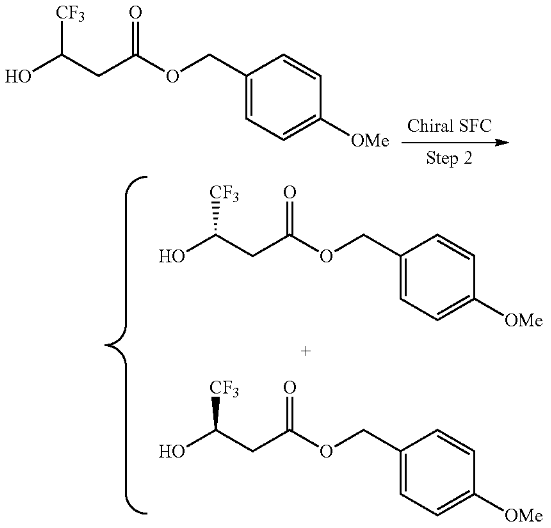

To a mixture of 4,4,4-trifluoro-3-hydroxybutanoic acid (45 g, 285 mmol) and $K_2CO_3$ (39.3 g, 285 mmol) in dimethylformamide (1200 mL) was added PMBCl (44.5 g, 285 mmol) at 0° C., and the reaction mixture was stirred at room temperature overnight. The reaction mixture was quenched with water and extracted with EtOAc. The organic layers were washed with water and brine, dried over anhydrous $Na_2SO_4$ and filtered. The filtrate was concentrated under reduced pressure at 40° C. and the residue was purified by flash column chromatography (120 g $SiO_2$, 0-40% MTBE/petroleum ether) to give 4-methoxybenzyl 4,4,4-trifluoro-3-hydroxybutanoate (55 g, 198 mmol, 70%) as a white solid. LCMS (System 2, Method B) m/z 301.2 $(M+Na)^+$ $(ES^+)$.

Step 2

4-Methoxybenzyl 4,4,4-trifluoro-3-hydroxybutanoate (55 g, 198 mmol) was resolved into separate enantiomers using chiral SFC (Column: CHIRALPAK AD-5 5 µm 30×250 mm; Column temperature: 35° C.; Flow rate: 45 mL/min; Solvent system: 20% IPA/$CO_2$; Collection wavelength: 215 nm). The collected fractions were concentrated under reduced pressure at 40° C. to give 4-methoxybenzyl (S)-4,4,4-trifluoro-3-hydroxybutanoate (21 g, 75.5 mmol, 38%) as the first eluting peak and 4-methoxybenzyl (R)-4,4,4-trifluoro-3-hydroxybutanoate (21 g, 75.5 mmol, 38%) as the second eluting peak. Both compounds were isolated as white solids. Chiral SFC analysis (Column: CHIRALPAK AD-3 3 µm 4.6×100 mm; Column temperature: 35° C.; Flow rate: 2 mL/min; Solvent system: 20% (0.2% (7M $NH_3$/MeOH) in MeOH)/$CO_2$; Collection wavelength: 215 nm): 4-methoxybenzyl (S)-4,4,4-trifluoro-3-hydroxybutanoate Rt=0.943 min, 99.1% ee; 4-methoxybenzyl (R)-4,4,4-trifluoro-3-hydroxybutanoate Rt=1.281 min, 99.4% ee.

Intermediate 28—2,2,2-trichloroethyl (S)-4,4,4-trifluoro-3-hydroxybutanoate

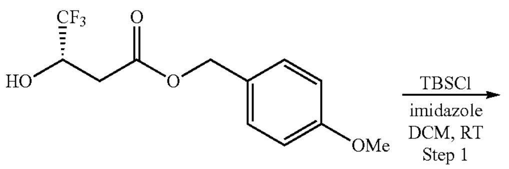

-continued

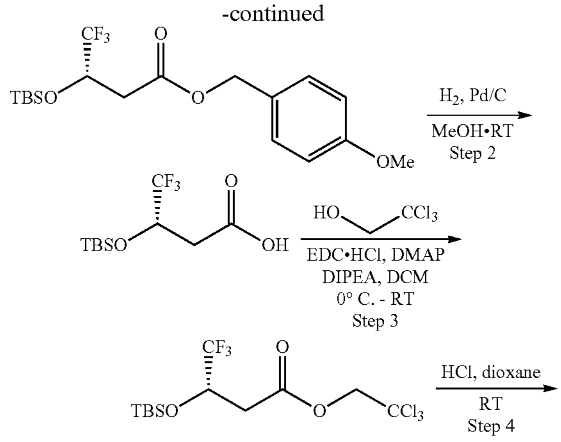

Step 1

A mixture of 4-methoxybenzyl (S)-4,4,4-trifluoro-3-hydroxybutanoate (Intermediate 26, 4.00 g, 14.4 mmol), tert-butylchlorodimethylsilane (5.43 g, 36.0 mmol) and imidazole (2.94 g, 43.2 mmol) in DCM (60 mL) was stirred at room temperature overnight. The mixture was quenched with $H_2O$ (50 mL), the phases were separated and the aqueous phase was extracted with DCM (2×500 mL). The combined organic phases were washed with brine, dried over $Na_2SO_4$ and filtered. The filtrate was concentrated under reduced pressure at 25° C., and the residue was purified by flash column chromatography (40 g silica, 0-10% MTBE/petroleum ether) to give 4-methoxybenzyl (S)-3-((tert-butyldimethylsilyl)oxy)-4,4,4-trifluorobutanoate (5.1 g, 13.0 mmol, 91%) as a pale yellow oil. LCMS (System 2, Method C) m/z 415.0 $(M+Na)^+$ $(ES^+)$.

Step 2

To a solution of (S)-3-((tert-butyldimethylsilyl)oxy)-4,4,4-trifluorobutanoate (5.1 g, 13.0 mmol) in MeOH (60 mL) was added 10% palladium on carbon (1.02 g) and the mixture was stirred at room temperature under an atmosphere of hydrogen for 3 h. The mixture was filtered through Celite and the filtrate was concentrated under reduced pressure at 35° C. to give crude (S)-3-((tert-butyldimethylsilyl)oxy)-4,4,4-trifluorobutanoic acid (3.9 g, 14.3 mmol, 100%) as a pale yellow oil, which was used directly in the next step. $^1H$ NMR (400 MHz, $CDCl_3$) δ: 4.54-4.43 (m, 1H), 2.80-2.61 (m, 2H), 0.87 (s, 9H), 0.13 (s, 3H), 0.09 (s, 3H). One exchangeable proton not observed.

Step 3

A mixture of (S)-3-((tert-butyldimethylsilyl)oxy)-4,4,4-trifluorobutanoic acid (3.9 g, 14.3 mmol), 2,2,2-trichloroethanol (4.27 g, 28.7 mmol), DMAP (2.63 g, 21.5 mmol), EDC·HCl (5.51 g, 28.7 mmol) and DIPEA (5.55 g, 43.0 mmol) in DCM (70 mL) at 0° C. was stirred overnight and allowed to warm to room temperature. The mixture was quenched with dilute aqueous HCl (0.5 M, 50 mL), the phases were separated, and the aqueous layer was extracted with DCM (2×50 mL). The combined organic phases were washed with brine, dried over $Na_2SO_4$ and filtered. The filtrate was concentrated under reduced pressure at 35° C., and the residue was purified by flash column chromatography (80 g silica, 0-9% MTBE/petroleum ether) to give 2,2,2-trichloroethyl (S)-3-((tert-butyldimethylsilyl)oxy)-4,4,4-trifluorobutanoate (2.9 g, 7.20 mmol, 56%) as a yellow oil. $^1H$ NMR (400 MHz, $CDCl_3$) δ: 4.81-4.72 (m, 2H), 4.59-4.49 (m, 1H), 2.90-2.75 (m, 2H), 0.91-0.81 (m, 9H), 0.14 (s, 3H), 0.10 (s, 3H).

Step 4

A solution of 2,2,2-trichloroethyl (S)-3-((tert-butyldimethylsilyl)oxy)-4,4,4-trifluorobutanoate (2.9 g, 7.20 mmol) in HCl solution in 1,4-dioxane (4 M, 60 mL) was stirred at room temperature for 2 days. The mixture was concentrated under reduced pressure at 35° C. and the residue was purified by flash column chromatography (0-10% EtOAc/petroleum ether) to give 2,2,2-trichloroethyl (S)-4,4,4-trifluoro-3-hydroxybutanoate (340 mg, 1.17 mmol, 16%) as a yellow oil. $^1H$ NMR (400 MHz, $CDCl_3$) δ: 4.88-4.74 (m, 2H), 4.59-4.47 (m, 1H), 3.01 (d, J=5.6 Hz, 1H), 2.96-2.81 (m, 2H).

Intermediate 29—2,2,2-trichloroethyl (R)-4,4,4-trifluoro-3-hydroxybutanoate

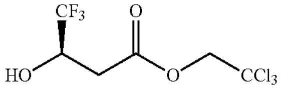

Prepared by an analogous procedure to Intermediate 28 starting from 4-methoxybenzyl (R)-4,4,4-trifluoro-3-hydroxybutanoate (Intermediate 27, 4.00 g, 14.4 mmol). Yield: 600 mg, 2.07 mmol. Yellow oil. $^1H$ NMR (400 MHz, $CDCl_3$) δ: 4.89-4.72 (m, 2H), 4.61-4.46 (m, 1H), 3.08 (d, J=5.6 Hz, 1H), 2.97-2.80 (m, 2H).

Intermediate 30—5,7-dichloro-1,2,3,4-tetrahydronaphthalen-1-ol Enantiomer 1 and Intermediate 31—5,7-dichloro-1,2,3,4-tetrahydronaphthalen-1-ol Enantiomer 2

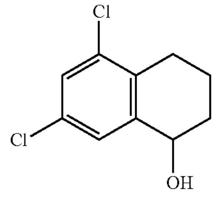 [SMILES: OC1CCCc2c(Cl)cc(Cl)cc21]

Racemic 5,7-dichloro-1,2,3,4-tetrahydronaphthalen-1-ol was prepared by an analogous method as that used in the preparation of Intermediate 3 and Intermediate 4. $^1H$ NMR (400 MHz, $CDCl_3$) δ: 7.38 (d, J=2.2 Hz, 1H), 7.28 (d, J=2.3 Hz, 1H), 4.74-4.65 (m, 1H), 2.83-2.71 (m, 1H), 2.70-2.58 (m, 1H), 2.02-1.93 (m, 2H), 1.85-1.74 (m, 2H). One exchangeable proton not observed.

Racemic 5,7-dichloro-1,2,3,4-tetrahydronaphthalen-1-ol (980 mg, 4.51 mmol) was resolved using chiral SFC (Column: CHIRALPAK AY-5, 5 μm 30×250 mm; Column temperature: 35° C.; Flow Rate: 45 mL/min; solvent system: 15% $MeCN/CO_2$; collection wavelength: 214 nm). The SFC fractions were concentrated under reduced pressure at 35° C. to remove MeCN to give 5,7-dichloro-1,2,3,4-tetrahydronaphthalen-1-ol Enantiomer 1 as the first eluting peak (400 mg, 1.8 mmol, 40%) and 5,7-dichloro-1,2,3,4-tetrahydronaphthalen-1-ol Enantiomer 2 as the second eluting peak (430 mg, 2.0 mmol, 43%). Chiral SFC analysis (Column: CHIRALPAK AY-3 3 μm 4.6×100 mm; Column temperature: 35° C.; Flow rate: 2 mL/min; Solvent system: 15% (1/1 MeCN/MeOH)/$CO_2$; Collection wavelength: 200-400 nm): 5,7-dichloro-1,2,3,4-tetrahydronaphthalen-1-ol Enantiomer 1: Rt=1.596 min, 100% ee; 5,7-dichloro-1,2,3,4-tetrahydronaphthalen-1-ol Enantiomer 2: Rt=1.864 min, 97.3% ee.

Intermediate 32—5,6-difluoro-1,1,3,3-tetramethyl-2,3-dihydro-1H-inden-2-ol

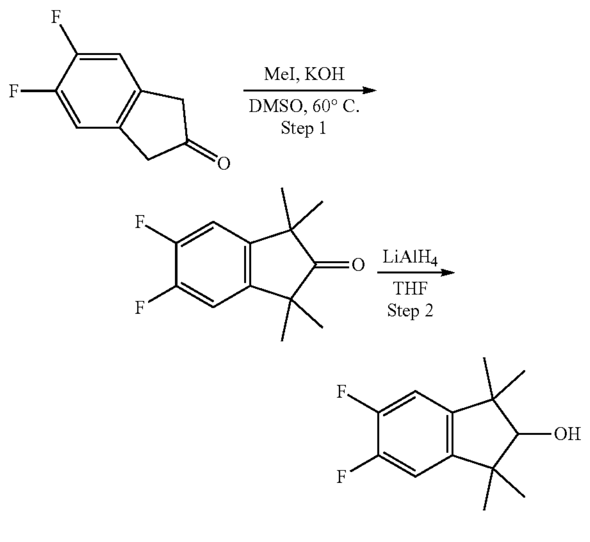

Step 1

A mixture of potassium hydroxide (2.27 g, 40.5 mmol) in DMSO (20 mL) was stirred at 60° C. for 30 minutes, then a mixture of 5,6-difluoro-1,3-dihydro-2H-inden-2-one (850 mg, 5.06 mmol) and methyl iodide (7.18 g, 50.6 mmol) were added at 60° C. The resulting suspension was stirred at 60° C. for 4 h. The mixture was cooled to room temperature, quenched with water (30 mL) and extracted with MTBE (3×20 mL). The combined organic layers were washed with water (3×20 mL), dried over $Na_2SO_4$, filtered, and concentrated under reduced pressure at 30° C. to give crude 5,6-difluoro-1,1,3,3-tetramethyl-1,3-dihydro-2H-inden-2-one (850 mg, 3.79 mmol, 75%) as a colorless oil. $^1H$ NMR (400 MHz, $CDCl_3$) δ: 7.04 (t, J=8.8 Hz, 2H), 1.31 (s, 12H).

Step 2

To a solution of 5,6-difluoro-1,1,3,3-tetramethyl-1,3-dihydro-2H-inden-2-one (850 mg, 3.79 mmol) in THF (15 mL) at 0° C. was added lithium aluminium hydride (296 mg, 7.78 mmol) in portions. The suspension was stirred at room temperature for 2 h, then the mixture was cooled to 0° C., and quenched by sequentially adding water (300 mg), 10% aqueous NaOH (300 mg) and water (900 mg). The resulting mixture was filtered, and the filtrate was concentrated under reduced pressure at 30° C. to give crude 5,6-difluoro-1,1,3,3-tetramethyl-2,3-dihydro-1H-inden-2-ol (850 mg, 3.76 mmol, 99%) as a pale yellow oil. $^1H$ NMR (400 MHz, $CDCl_3$) δ: 6.91 (t, J=9.0 Hz, 2H), 3.83-3.78 (m, 1H), 1.32 (s, 6H), 1.15 (s, 6H). One exchangeable proton not observed.

Intermediate 33—5-(trifluoromethyl)-2,3-dihydro-1H-inden-1-ol Enantiomer 1 and Intermediate 34—5-(trifluoromethyl)-2,3-dihydro-1H-inden-1-ol Enantiomer 2

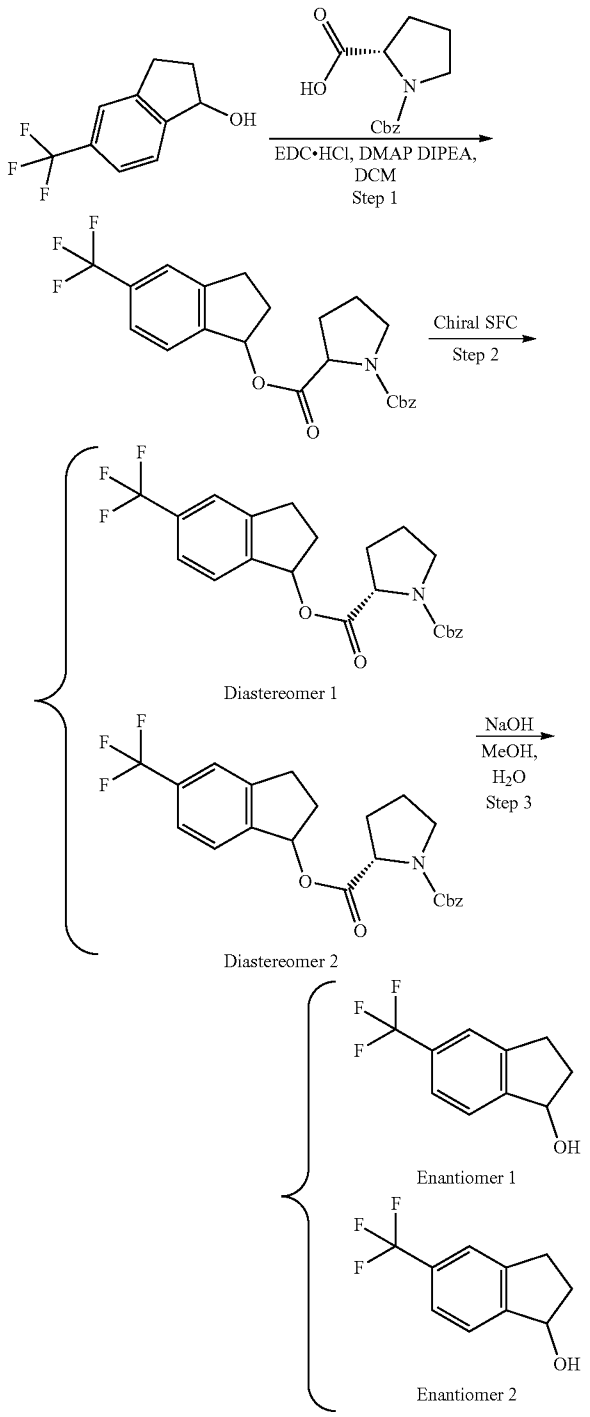

Step 1

To a solution of 5-(trifluoromethyl)-2,3-dihydro-1H-inden-1-ol (Intermediate 19, 1.00 g, 4.95 mmol), ((benzyloxy)carbonyl)-L-proline (1.85 g, 7.42 mmol) and DMAP (905 mg, 7.42 mmol) in DCM (25 mL) at 0° C. was added EDC·HCl (1.90 g, 9.90 mmol) and DIPEA (2.55 g, 19.8 mmol), and the resulting pale-yellow mixture was stirred at room temperature overnight. The reaction mixture was adjusted to pH=5 with dilute aqueous HCl (0.5 M), the phases were separated and the aqueous layer was extracted with DCM (2×25 mL). The combined organic phases were washed with brine, dried over $Na_2SO_4$ and filtered. The filtrate was concentrated under reduced pressure at 25° C., and the residue was purified by flash column chromatography (12 g silica, 0-10% MTBE/petroleum ether) to give 1-benzyl 2-(5-(trifluoromethyl)-2,3-dihydro-1H-inden-1-yl) (2S)-pyrrolidine-1,2-dicarboxylate (1.30 g, 3.00 mmol, 60%) as a yellow oil. LCMS: (System 2, Method C) m/z 456.0 $(M+Na)^+$ $(ES^+)$.

Step 2

The diastereomers of 1-benzyl 2-(5-(trifluoromethyl)-2,3-dihydro-1H-inden-1-yl) (2S)-pyrrolidine-1,2-dicarboxylate (1.30 g, 3.00 mmol) were separated using chiral SFC (Column: CHIRALPAK AD-5, 5 μm 30×250 mm; Column temperature: 35° C.; Flow Rate: 45 mL/min; solvent system: 20% $MeOH/CO_2$; collection wavelength: 215 nm). The SFC fractions were concentrated under reduced pressure at 35° C. to remove MeOH to give 1-benzyl 2-(5-(trifluoromethyl)-2,3-dihydro-1H-inden-1-yl) (2S)-pyrrolidine-1,2-dicarboxylate Diastereomer 1 as the first eluting peak (600 mg, 1.38 mmol, 46%) and 1-benzyl 2-(5-(trifluoromethyl)-2,3-dihydro-1H-inden-1-yl) (2S)-pyrrolidine-1,2-dicarboxylate Diastereomer 2 as the second eluting peak (600 mg, 1.38 mmol, 46%). Chiral SFC analysis (Column: CHIRALPAK AD-3 3 μm 4.6×100 mm; Column temperature: 35° C.; Flow rate: 2 mL/min; Solvent system: 20% $MeOH/CO_2$; Collection wavelength: 200-400 nm): 1-benzyl 2-(5-(trifluoromethyl)-2,3-dihydro-1H-inden-1-yl) (2S)-pyrrolidine-1,2-dicarboxylate Diastereomer 1: Rt=1.446 min, 100% ee; 1-benzyl 2-(5-(trifluoromethyl)-2,3-dihydro-1H-inden-1-yl) (2S)-pyrrolidine-1,2-dicarboxylate Diastereomer 2: Rt=2.130 min, 100% ee.

Step 3

The individual diastereomers of 1-benzyl 2-(5-(trifluoromethyl)-2,3-dihydro-1H-inden-1-yl) (2S)-pyrrolidine-1,2-dicarboxylate (600 mg, 1.38 mmol) were separately dissolved in $MeOH:H_2O$ (2:1, 7.5 mL), treated with NaOH (110 mg, 2.76 mmol) and stirred at room temperature overnight. The separate mixtures were concentrated under reduced pressure at 25° C., the residues were adjusted to pH=5 with dilute aqueous HCl (0.5 M), the phases were separated, and the aqueous layers were extracted with EtOAc (2×5 mL). The separated organic phases were washed with brine, dried over $Na_2SO_4$ and filtered. The filtrates were concentrated under reduced pressure at 25° C. to give 5-(trifluoromethyl)-2,3-dihydro-1H-inden-1-ol Enantiomer 1 (250 mg, 1.24 mmol, 89%) from 1-benzyl 2-(5-(trifluoromethyl)-2,3-dihydro-1H-inden-1-yl) (2S)-pyrrolidine-1,2-dicarboxylate Diastereomer 1 and 5-(trifluoromethyl)-2,3-dihydro-1H-inden-1-ol Enantiomer 2 (250 mg, 1.24 mmol, 89%) from 1-benzyl 2-(5-(trifluoromethyl)-2,3-dihydro-1H-inden-1-yl) (2S)-pyrrolidine-1,2-dicarboxylate Diastereomer 2, both as yellow solids. 5-(trifluoromethyl)-2,3-dihydro-1H-inden-1-ol Enantiomer 1: $^1H$ NMR (400 MHz, $CDCl_3$) δ: 7.51 (s, 3H), 5.28 (t, J=6.5 Hz, 1H), 3.15-3.03 (m, 1H), 2.93-2.80 (m, 1H), 2.63-2.50 (m, 1H), 2.06-1.92 (m, 1H), 1.83 (s, 1H). 5-(trifluoromethyl)-2,3-dihydro-1H-inden-1-ol Enantiomer 2: LCMS: (System 2, Method C) m/z 185.2 $(M-OH)^+$ $(ES^+)$.

Intermediate 35—6-(trifluoromethoxy)-2,3-dihydro-1H-inden-1-ol Enantiomer 1 and Intermediate 36—6-(trifluoromethoxy)-2,3-dihydro-1H-inden-1-ol Enantiomer 2

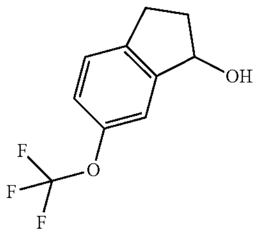 [SMILES: OC1CCc2ccc(OC(F)(F)F)cc21]

Racemic 6-(trifluoromethoxy)-2,3-dihydro-1H-inden-1-ol (Intermediate 20, 1.40 g, 6.42 mmol) was resolved using chiral SFC (Column: CHIRALPAK AD-5, 5 μm 30×250 mm; Column temperature: 35° C.; Flow Rate: 45 mL/min; solvent system: 20% $IPA/CO_2$; collection wavelength: 215 nm). The SFC fractions were concentrated under reduced pressure at 35° C. to remove IPA to give 6-(trifluoromethoxy)-2,3-dihydro-1H-inden-1-ol Enantiomer 1 as the first eluting peak (650 mg, 3.0 mmol, 46%) and 6-(trifluoromethoxy)-2,3-dihydro-1H-inden-1-ol Enantiomer 2 as the second eluting peak (600 mg, 2.8 mmol, 42%). Chiral SFC analysis (Column: CHIRALPAK AD-3 3 μm 4.6×100 mm; Column temperature: 35° C.; Flow rate: 2 mL/min; Solvent system: 15% $IPA/CO_2$; Collection wavelength: 200-400 nm): 6-(trifluoromethoxy)-2,3-dihydro-1H-inden-1-ol Enantiomer 1: Rt=0.878 min, 98.7% ee; 5,7-dichloro-1,2,3,4-tetrahydronaphthalen-1-ol Enantiomer 2: Rt=1.007 min, 96.2% ee.

Intermediate 37—2-methylene-4-oxo-4-((5-(trifluoromethyl)-2,3-dihydro-1H-inden-1-yl)oxy)butanoic acid

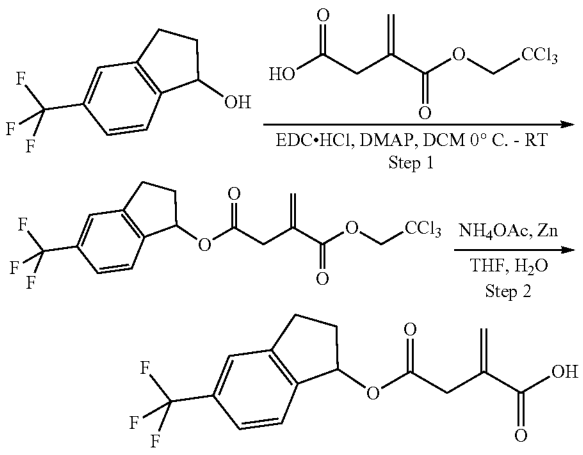

Step 1

To a solution of 5-(trifluoromethyl)-2,3-dihydro-1H-inden-1-ol (Intermediate 19, 200 mg, 0.99 mmol), 3-((2,2,2-trichloroethoxy)carbonyl)but-3-enoic acid (Intermediate 24, 285 mg, 1.09 mmol) and DMAP (97 mg, 0.79 mmol) in DCM (5 mL) at 0° C. was added EDC·HCl (285 mg, 1.49 mmol), and the resulting pale yellow mixture was stirred at room temperature for 20 min. The mixture was quenched with dilute aqueous HCl (0.5 M, 2 mL), the phases were separated and the aqueous phase was extracted with DCM (3×5 mL). The combined organic phases were washed with brine, dried over Na2SO4 and filtered. The filtrate was concentrated under reduced pressure at 25° C., and the residue was purified by flash column chromatography (12 g silica, 0-20% MTBE/petroleum ether) to give 1-(2,2,2-trichloroethyl) 4-(5-(trifluoromethyl)-2,3-dihydro-1H-inden-1-yl) 2-methylenesuccinate (250 mg, 0.56 mmol, 56%) as a colorless oil. LCMS: (System 2, Method C) m/z 466.8 $(M+Na)^+$ $(ES^+)$.

Step 2

A mixture of 1-(2,2,2-trichloroethyl) 4-(5-(trifluoromethyl)-2,3-dihydro-1H-inden-1-yl) 2-methylenesuccinate (250 mg, 0.56 mmol), ammonium acetate (431 mg, 5.60 mmol) and zinc powder (182 mg, 2.80 mmol) in THF (1 mL) and H2O (0.2 mL) was stirred at room temperature for 2 h. The reaction mixture was filtered, and the filtrate was diluted with H2O (3 mL). The phases were separated and the aqueous layer was extracted with EtOAc (2×5 mL). The combined organic phases were washed with brine, dried over Na2SO4 and filtered. The mixture was concentrated under reduced pressure at 25° C. and the residue was purified by preparative HPLC (Column: Waters X-Bridge C18 OBD 10 μm 19×250 mm; Flow Rate: 20 mL/min; solvent system: MeCN/(0.2% formic acid/water); gradient: 55-95% MeCN; collection wavelength: 214 nm). The collected fractions were concentrated under reduced pressure at 30° C. to remove MeCN, and the residue was lyophilized to give 2-methylene-4-oxo-4-((5-(trifluoromethyl)-2,3-dihydro-1H-inden-1-yl)oxy)butanoic acid (95 mg, 0.30 mmol, 54% yield) as a white solid. LCMS: (System 2, Method C) m/z 336.9 (M+Na)+ (ES+). 1H NMR (400 MHz, DMSO-d6) δ: 12.70 (br, 1H), 7.68 (s, 1H), 7.59 (d, J=8.0 Hz, 1H), 7.51 (d, J=8.0 Hz, 1H), 6.20-6.11 (m, 2H), 5.77 (s, 1H), 3.13-3.01 (m, 1H), 2.99-2.87 (m, 1H), 2.57-2.43 (m, 1H), 2.07-1.95 (m, 1H). Two protons obscured by solvent peak.

Intermediate 38—6-(trifluoromethyl)-1,2,3,4-tetrahydronaphthalen-1-ol Enantiomer 1 and Intermediate 39—6-(trifluoromethyl)-1,2,3,4-tetrahydronaphthalen-1-ol Enantiomer 2

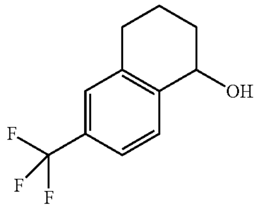 [SMILES: OC1CCCc2cc(C(F)(F)F)ccc21]

Racemic 6-(trifluoromethyl)-1,2,3,4-tetrahydronaphthalen-1-ol was prepared by an analogous method as that used in the preparation of Intermediate 3 and Intermediate 4. LCMS: (System 2, Method C) m/z 199.0 (M-OH)+ (ES+).

Racemic 6-(trifluoromethyl)-1,2,3,4-tetrahydronaphthalen-1-ol (1.0 g, 4.63 mmol) was resolved into separate enantiomers by an analogous procedure to that used to prepare Intermediate 33 and Intermediate 34. The diasteromers formed at Step 1 were separated using chiral SFC (Column: CHIRALPAK AD-5, 5 μm 30×250 mm; Column temperature: 35° C.; Flow Rate: 45 mL/min; solvent system: 15% MeOH/CO2; collection wavelength: 215 nm). The SFC fractions were concentrated under reduced pressure at 35° C. to remove MeOH to give 1-benzyl 2-(6-(trifluoromethyl)-1,2,3,4-tetrahydronaphthalen-1-yl) (2S)-pyrrolidine-1,2-dicarboxylate Diastereomer 1 as the first eluting peak (890 mg, 1.99 mmol, 46%) and 1-benzyl 2-(6-(trifluoromethyl)-1,2,3,4-tetrahydronaphthalen-1-yl) (2S)-pyrrolidine-1,2-dicarboxylate Diastereomer 2 as the second eluting peak (800 mg, 1.79 mmol, 42%). Chiral SFC analysis (Column: CHIRALPAK AD-3 3 μm 4.6×100 mm; Column temperature: 35° C.; Flow rate: 2 mL/min; Solvent system: 15% MeOH/CO2; Collection wavelength: 200-400 nm): 1-benzyl 2-(6-(trifluoromethyl)-1,2,3,4-tetrahydronaphthalen-1-yl) (2S)-pyrrolidine-1,2-dicarboxylate Diastereomer 1: Rt=1.764 min, 98.9% ee; 1-benzyl 2-(6-(trifluoromethyl)-1,2,3,4-tetrahydronaphthalen-1-yl) (2S)-pyrrolidine-1,2-dicarboxylate Diastereomer 2: Rt=2.137 min, 100% ee.

The individual diastereomers were then hydrolysed to give 6-(trifluoromethyl)-1,2,3,4-tetrahydronaphthalen-1-ol Enantiomer 1 (400 mg, 1.85 mmol, 93%) from 1-benzyl 2-(6-(trifluoromethyl)-1,2,3,4-tetrahydronaphthalen-1-yl) (2S)-pyrrolidine-1,2-dicarboxylate Diastereomer 1 and 6-(trifluoromethyl)-1,2,3,4-tetrahydronaphthalen-1-ol Enantiomer 2 (380 mg, 1.16 mmol, 98%) from 1-benzyl 2-(6-(trifluoromethyl)-1,2,3,4-tetrahydronaphthalen-1-yl) (2S)-pyrrolidine-1,2-dicarboxylate Diastereomer 2, both as yellow solids. 6-(Trifluoromethyl)-1,2,3,4-tetrahydronaphthalen-1-ol Enantiomer 1: LCMS: (System 2, Method C) m/z 199.2 (M-OH)+ (ES+). 6-(Trifluoromethyl)-1,2,3,4-tetrahydronaphthalen-1-ol Enantiomer 2: LCMS: (System 2, Method C) m/z 199.2 (M-OH)+ (ES+).

Intermediate 40—2-methylene-4-oxo-4-((6-(trifluoromethyl)-1,2,3,4-tetrahydronaphthalen-1-yl)oxy) butanoic acid (Enantiomer 1)

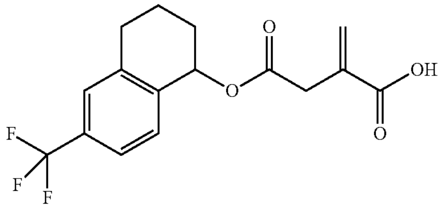 [SMILES: C=C(CC(=O)OC1CCCc2cc(C(F)(F)F)ccc21)C(=O)O]

Prepared by an analogous procedure to that used to prepare Intermediate 37, starting from 6-(trifluoromethyl)-1,2,3,4-tetrahydronaphthalen-1-ol Enantiomer 1 (Intermediate 38, 200 mg, 0.93 mmol). Yield 143 mg, 0.44 mmol). White solid. LCMS: (System 2, Method B) 350.9 $(M+Na)^+$. $^1H$ NMR (400 MHz, DMSO-d6) δ: 12.69 (s, 1H), 7.55-7.48 (m, 2H), 7.43 (d, J=8.0 Hz, 1H), 6.14 (d, J=1.6 Hz, 1H), 5.92 (t, J=5.1 Hz, 1H), 5.77 (s, 1H), 3.34 (s, 2H), 2.95-2.84 (m, 1H), 2.83-2.71 (m, 1H), 2.03-1.92 (m, 1H), 1.91-1.74 (m, 3H).

Intermediate 41—2-methylene-4-oxo-4-((6-(trifluoromethyl)-1,2,3,4-tetrahydronaphthalen-1-yl)oxy)butanoic acid (Enantiomer 2)

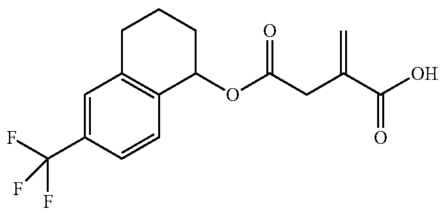 [SMILES: C=C(CC(=O)OC1CCCc2cc(C(F)(F)F)ccc21)C(=O)O]

Prepared by an analogous procedure to that used to prepare Intermediate 37, starting from 6-(trifluoromethyl)-1,2,3,4-tetrahydronaphthalen-1-ol Enantiomer 2 (Intermediate 39, 200 mg, 0.93 mmol). Yield 108 mg, 0.33 mmol). White solid. LCMS: (System 2, Method B) 350.9 $(M+Na)^+$. $^1H$ NMR (400 MHz, DMSO-d6) δ: 12.73 (s, 1H), 7.55-7.48 (m, 2H), 7.43 (d, J=8.0 Hz, 1H), 6.14 (d, J=1.7 Hz, 1H), 5.92 (t, J=5.1 Hz, 1H), 5.77 (s, 1H), 2.95-2.84 (m, 1H), 2.83-2.71 (m, 1H), 2.03-1.92 (m, 1H), 1.91-1.74 (m, 3H). Two protons obscured by solvent peak.

Example 1—2-((4-((5-chloro-2,3-dihydro-1H-inden-2-yl)oxy)-2-methylene-4-oxobutanoyl)oxy)acetic acid

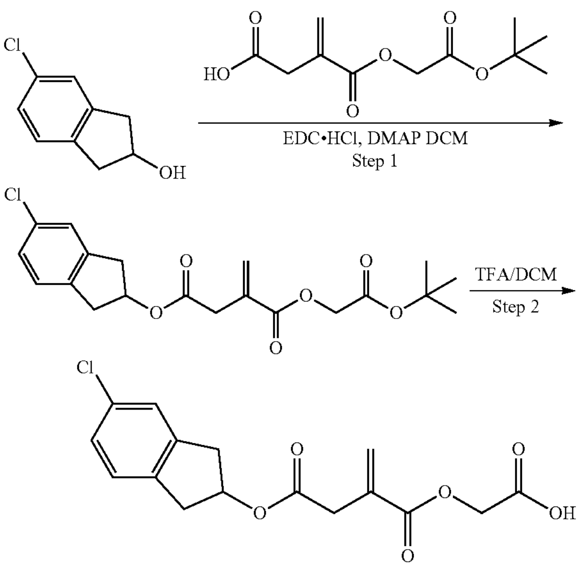

Step 1

To a solution of 5-chloro-2,3-dihydro-1H-inden-2-ol (Intermediate 2, 220 mg, 1.30 mmol), 3-((2-(tert-butoxy)-2-oxoethoxy)carbonyl)but-3-enoic acid (Intermediate 1, 318 mg, 1.30 mmol) and DMAP (127 mg, 1.04 mmol) in DCM (5 mL) at 0° C. was added EDC·HCl (374 mg, 1.95 mmol), and the resulting pale yellow mixture was stirred at room temperature for 20 min. The reaction mixture was adjusted to pH=5 with dilute aqueous HCl (0.5 M) and the phase were separated. The aqueous layer was extracted with DCM (2×5 mL), then the combined organic phases were washed with brine, dried over $Na_2SO_4$ and filtered. The filtrate was concentrated under reduced pressure 30° C., and the residue was purified by flash column chromatography (12 g $SiO_2$, 0-10% MTBE/petroleum ether) to give 1-(2-(tert-butoxy)-2-oxoethyl) 4-(5-chloro-2,3-dihydro-1H-inden-2-yl) 2-methylenesuccinate (250 mg, 0.633 mmol, 48%) as a yellow oil. LCMS: (System 2, Method C) 417.2/419.2 $(M+Na)^+$.

Step 2

A solution of 1-(2-(tert-butoxy)-2-oxoethyl) 4-(5-chloro-2,3-dihydro-1H-inden-2-yl) 2-methylenesuccinate (250 mg, 0.63 mmol) in TFA (2 mL) and DCM (4 mL) was stirred at room temperature for 16 h. The mixture was concentrated under reduced pressure at 30° C. and the residue was purified by preparative HPLC (Column: Waters X-Bridge C18 OBD 10 μm 19×250 mm; Flow Rate: 20 mL/min; solvent system: MeCN/(0.2% formic acid/water); gradient: 45-95% MeCN; collection wavelength: 214 nm). The collected fractions were concentrated under reduced pressure at 25° C. to remove MeCN, and the residue was lyophilized to give 2-((4-((5-chloro-2,3-dihydro-1H-inden-2-yl)oxy)-2-methylene-4-oxobutanoyl)oxy)acetic acid (143 mg, 0.42 mmol, 66%) as a white solid. LCMS: (System 2, Method B) m/z 361.0/363.0 $(M+Na)^+$ $(ES^+)$. $^1H$ NMR (400 MHz, DMSO-d6) δ: 13.10 (br, 1H), 7.32 (s, 1H), 7.27 (d, J=8.1 Hz, 1H), 7.21 (dd, J=8.0, 2.0 Hz 1H), 6.25 (s, 1H), 5.89 (s, 1H), 5.47-5.38 (m, 1H), 4.59 (s, 2H), 3.33-3.18 (m, 4H), 2.94-2.83 (m, 2H).

The following compounds were prepared by an analogous method:

| Example No. | Alcohol used in step 1/Example Structure/Name | LCMS/¹H NMR data |
|---|---|---|
| 10 | 6,8-dichloro-1,2,3,4-tetrahydronaphthalen-2-ol Enantiomer 1 (Intermediate 12)<br>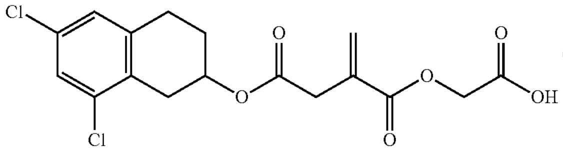<br>2-((4-((6,8-dichloro-1,2,3,4-tetrahydronaphthalen-2-yl)oxy)-2-methylene-4-oxobutanoyl)oxy)acetic acid (Enantiomer 1) | LCMS (System 2, Method B) m/z 408.9/411.0 $(M + Na)^+$ $(ES^+)$. $^1$H NMR (400 MHz, DMSO-d6) δ: 13.08 (s, 1H), 7.43 (d, J = 2.2 Hz, 1H), 7.25 (d, J = 2.2 Hz, 1H), 6.26 (s, 1H), 5.91 (s, 1H), 5.22-5.12 (m, 1H), 4.56 (s, 2H), 3.38 (s, 2H), 3.00 (dd, J = 17.8, 5.1 Hz, 1H), 2.91-2.73 (m, 2H), 2.71 (dd, J = 17.8, 5.4 Hz, 1H), 1.94-1.82 (m, 2H). |
| 11 | 6,8-dichloro-1,2,3,4-tetrahydronaphthalen-2-ol Enantiomer 2 (Intermediate 13)<br>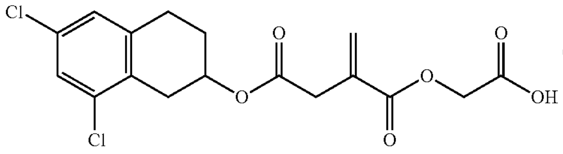<br>2-((4-((6,8-dichloro-1,2,3,4-tetrahydronaphthalen-2-yl)oxy)-2-methylene-4-oxobutanoyl)oxy)acetic acid (Enantiomer 2) | LCMS (System 2, Method B) m/z 409.0/411.0 $(M + Na)^+$ $(ES^+)$. $^1$H NMR (400 MHz, DMSO-d6) δ: 13.11 (s, 1H), 7.43 (d, J = 2.1 Hz, 1H), 7.25 (d, J = 2.1 Hz, 1H), 6.26 (s, 1H), 5.91 (s, 1H), 5.22-5.12 (m, 1H), 4.56 (s, 2H), 3.38 (s, 2H), 3.00 (dd, J = 17.8, 5.1 Hz, 1H), 2.91-2.73 (m, 2H), 2.71 (dd, J = 17.8, 5.4 Hz, 1H), 1.93-1.83 (m, 2H). |
| 26 | 5,6-difluoro-1,1,3,3-tetramethyl-2,3-dihydro-1H-inden-2-ol (Intermediate 32)<br>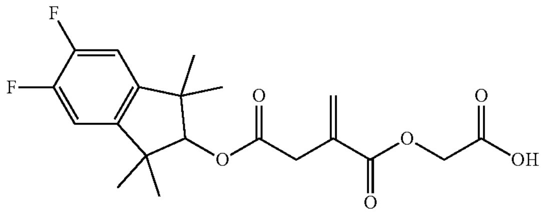<br>2-((4-((5,6-difluoro-1,1,3,3-tetramethyl-2,3-dihydro-1H-inden-2-yl)oxy)-2-methylene-4-oxobutanoyl)oxy)acetic acid | LCMS (System 2, Method B) m/z 418.9 $(M + Na)^+$ $(ES^+)$. $^1$H NMR (400 MHz, DMSO-d6) δ: 13.14 (br, 1H), 7.33 (t, J = 9.3 Hz, 2H), 6.33 (s, 1H), 6.00 (s, 1H), 4.97 (s, 1H), 4.64 (s, 2H), 3.52 (s, 2H), 1.27 (s, 6H), 1.09 (s, 6H). |

Example 2—2-((4-((4,6-dichloro-2,3-dihydro-1H-inden-1-yl)oxy)-2-methylene-4-oxobutanoyl)oxy) acetic acid (Enantiomer 1)

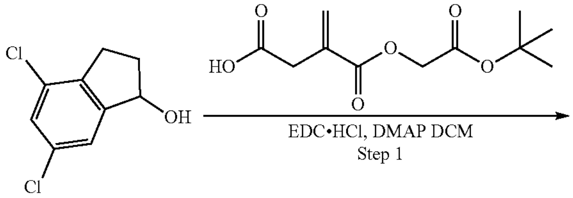

-continued

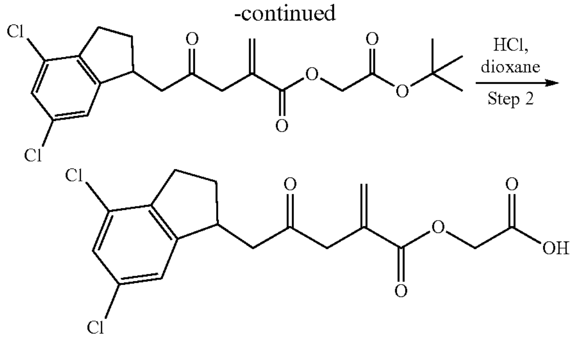

Step 1

To a solution of 4,6-dichloro-2,3-dihydro-1H-inden-1-ol Enantiomer 1 (Intermediate 3, 250 mg, 1.23 mmol), 3-((2-(tert-butoxy)-2-oxoethoxy)carbonyl)but-3-enoic acid (Intermediate 1, 301 mg, 1.23 mmol) and DMAP (120 mg, 0.98 mmol) in DCM (6 mL) at 0° C. was added EDC·HCl (354 mg, 1.85 mmol), and the resulting pale yellow mixture was stirred at room temperature for 20 min. The reaction mixture adjusted pH=5 with dilute aqueous HCl (0.5 M), the phases were separated and the aqueous phase was extracted with DCM (2×6 mL). The combined organic phases were washed with brine, dried over $Na_2SO_4$ and filtered. The filtrate was concentrated under reduced pressure at 30° C., and the residue was purified by flash column chromatography (12 g $SiO_2$, 0-10% MTBE/petroleum ether) to give 1-(2-(tert-butoxy)-2-oxoethyl) 4-(4,6-dichloro-2,3-dihydro-1H-inden-1-yl) 2-methylenesuccinate (Enantiomer 1) (300 mg, 0.70 mmol, 56%) as a yellow oil. LCMS: (System 2, Method C) m/z 451.0/452.9 $(M+Na)^+$ $(ES^+)$.

Step 2

A solution of 1-(2-(tert-butoxy)-2-oxoethyl) 4-(4,6-dichloro-2,3-dihydro-1H-inden-1-yl) 2-methylenesuccinate (Enantiomer 1) (300 mg, 0.70 mmol) in HCl solution in 1,4-dioxane (4 M, 3 mL) was stirred at room temperature overnight. The mixture was concentrated under reduced pressure at 30° C., and the residue was purified by preparative HPLC (Column: Waters X-Bridge C18 OBD 10 μm 19×250 mm; Flow Rate: 20 mL/min; solvent system: MeCN/(0.2% formic acid/water); gradient: 55-95% MeCN; collection wavelength: 214 nm). The collected fractions were concentrated under reduced pressure at 40° C. to remove MeCN, and the residue was lyophilized to give 2-((4-((4,6-dichloro-2,3-dihydro-1H-inden-1-yl)oxy)-2-methylene-4-oxobutanoyl)oxy)acetic acid (Enantiomer 1) (94 mg, 0.25 mmol, 36%) as a colorless oil. LCMS: (System 2, Method B) m/z 395.0/396.9 $(M+Na)^+$ $(ES^+)$. $^1H$ NMR (400 MHz, DMSO-d6) δ: 13.11 (s, 1H), 7.57 (d, J=1.8 Hz, 1H), 7.34 (d, J=1.8 Hz, 1H), 6.29 (s, 1H), 6.17-6.11 (m, 1H), 5.94 (s, 1H), 4.63 (d, J=2.1 Hz, 2H), 3.42 (s, 2H), 3.04-2.92 (m, 1H), 2.90-2.79 (m, 1H), 2.57-2.45 (m, 1H), 2.08-1.97 (m, 1H).

The following compounds were prepared by an analogous method:

| Example No. | Alcohol used in step 1/Example Structure/Name | LCMS/$^1H$ NMR data |
|---|---|---|
| 3 | 4,6-dichloro-2,3-dihydro-1H-inden-1-ol Enantiomer 2 (Intermediate 4) 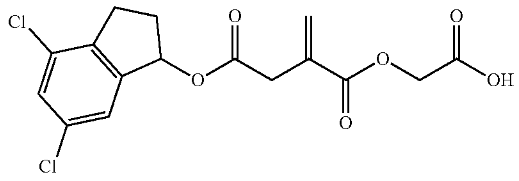 2-((4-((4,6-dichloro-2,3-dihydro-1H-inden-1-yl)oxy)-2-methylene-4-oxobutanoyl)oxy)acetic acid (Enantiomer 2) | LCMS (System 2, Method B) m/z 395.0/396.9 $(M + Na)^+$ $(ES^+)$. $^1H$ NMR (400 MHz, DMSO-d6) δ: 13.11 (s, 1H), 7.57 (d, J = 1.8 Hz, 1H), 7.34 (d, J = 1.8 Hz, 1H), 6.29 (s, 1H), 6.17-6.11 (m, 1H), 5.94 (s, 1H), 4.63 (d, J = 2.2 Hz, 2H), 3.42 (s, 2H), 3.04-2.92 (m, 1H), 2.90-2.79 (m, 1H), 2.57-2.45 (m, 1H), 2.08-1.97 (m, 1H). |
| 4 | 5,6-dichloro-2,3-dihydro-1H-inden-2-ol (Enantiomer 5) 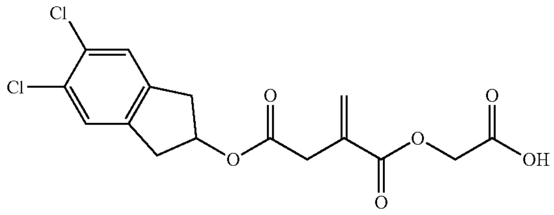 2-((4-((5,6-dichloro-2,3-dihydro-1H-inden-2-yl)oxy)-2-methylene-4-oxobutanoyl)oxy)acetic acid | LCMS (System 2, Method B) m/z 395.0/397.0 $(M + Na)^+$ $(ES^+)$. $^1H$ NMR (400 MHz, DMSO-d6) δ: 13.13 (br, 1H), 7.53 (s, 2H), 6.25 (d, J = 1.2 Hz, 1H), 5.89 (d, J = 1.2 Hz, 1H), 5.46-5.40 (m, 1H), 4.59 (s, 2H), 3.33 (s, 2H), 3.31-3.21 (m, 2H), 2.90 (dd, J = 17.6, 2.2 Hz, 2H0HH h). |

Example 5—2-((4-((5,6-dichloro-2,3-dihydro-1H-inden-1-yl)oxy)-2-methylene-4-oxobutanoyl)oxy) acetic acid (Enantiomer 1)

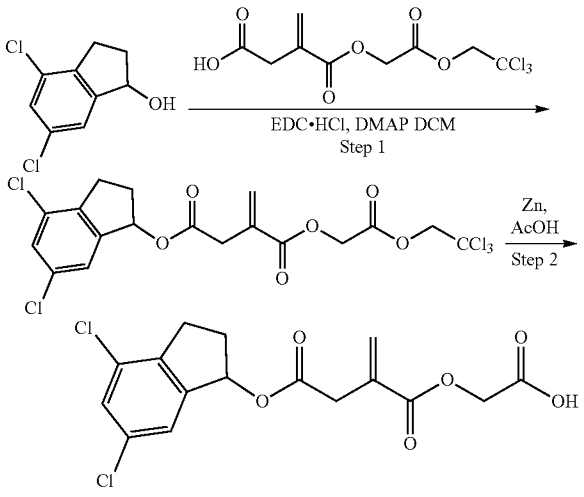

Step 1

To a solution of 5,6-dichloro-2,3-dihydro-1H-inden-1-ol Enantiomer 1 (Intermediate 7, 200 mg, 0.99 mmol), 3-((2-oxo-2-(2,2,2-trichloroethoxy)ethoxy)carbonyl)but-3-enoic acid (Intermediate 6, 315 mg, 0.99 mmol) and DMAP (97 mg, 0.79 mmol) in DCM (5 mL) at 0° C. was added EDC·HCl (285 mg, 1.48 mmol), and the resulting pale yellow mixture was stirred at room temperature for 20 min. The mixture was quenched with saturated aqueous $NH_4Cl$ solution (5 mL), the phases were separated, and the aqueous layer was extracted with DCM (2×5 mL). The combined organic phases were washed with brine, dried over $Na_2SO_4$ and filtered. The filtrate was concentrated under reduced pressure at 40° C., and the residue was purified by flash column chromatography (25 g $SiO_2$, 0-12% MTBE/petroleum ether) to give 4-(5,6-dichloro-2,3-dihydro-1H-inden-1-yl) 1-(2-oxo-2-(2,2,2-trichloroethoxy)ethyl) 2-methylenesuccinate (Enantiomer 1) (270 mg, 0.54 mmol, 54%) as a pale yellow oil. LCMS: (System 2, Method C) m/z 526.8/528.8 $(M+Na)^+$ $(ES^+)$.

Step 2

To a solution of 4-(5,6-dichloro-2,3-dihydro-1H-inden-1-yl) 1-(2-oxo-2-(2,2,2-trichloroethoxy)ethyl) 2-methylenesuccinate (Enantiomer 1) (270 mg, 0.54 mmol) in AcOH (5 mL) was added zinc powder (140 mg, 2.16 mmol), and the reaction mixture was stirred at room temperature overnight. The reaction mixture was filtered, and the filtrate was concentrated under reduced pressure at 35° C. The residue was purified by preparative HPLC (Column: Waters X-Bridge C18 OBD 10 μm 19×250 mm; Flow Rate: 20 mL/min; solvent system: MeCN/(0.2% formic acid/water); gradient: 45-95% MeCN; collection wavelength: 214 nm). The collected fractions were concentrated under reduced pressure at 35° C. to remove MeCN, and the residue was lyophilized to give 2-((4-((5,6-dichloro-2,3-dihydro-1H-inden-1-yl)oxy)-2-methylene-4-oxobutanoyl)oxy)acetic acid (Enantiomer 1) (119 mg, 0.32 mmol, 59%) as a white solid. LCMS: (System 2, Method B) m/z 395.0/397.0 $(M+Na)^+$ $(ES^+)$. $^1H$ NMR (400 MHz, DMSO-d6) δ: 13.12 (br, 1H), 7.61 (s, 1H), 7.53 (s, 1H), 6.29 (d, J=1.1 Hz, 1H), 6.07 (dd, J=7.2, 4.2 Hz, 1H), 5.94 (d, J=1.2 Hz, 1H), 4.63 (d, J=1.9 Hz, 2H), 3.41 (s, 2H), 3.04-2.92 (m, 1H), 2.90-2.78 (m, 1H), 2.50-2.40 (m, 1H), 2.06-1.95 (m, 1H).

The following compounds were prepared by an analogous method:

| Example No. | Alcohol used in step 1/Example Structure/Name | LCMS/$^1H$ NMR data |
|---|---|---|
| 6 | 5,6-dichloro-2,3-dihydro-1H-inden-1-ol Enantiomer 2 (Intermediate 8) 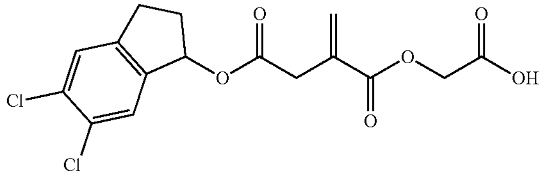 2-((4-((5,6-dichloro-2,3-dihydro-1H-inden-1-yl)oxy)-2-methylene-4-oxobutanoyl)oxy)acetic acid (Enantiomer 2) | LCMS (System 2, Method B) m/z 395.0/397.0 $(M + Na)^+$ $(ES^+)$. $^1H$ NMR (400 MHz, DMSO-d6) δ: 13.11 (br, 1H), 7.61 (s, 1H), 7.52 (s, 1H), 6.29 (s, 1H), 6.07 (dd, J = 7.2, 4.3 Hz, 1H), 5.94 (d, J = 1.3 Hz, 1H), 4.63 (d, J = 1.9 Hz, 2H), 3.41 (s, 2H), 3.05-2.92 (m, 1H), 2.90-2.78 (m, 1H), 2.50-2.40 (m, 1H), 2.07-1.95 (m, 1H). |
| 8 | 5,7-dichloro-2,3-dihydro-1H-inden-1-ol Enantiomer 1 (Intermediate 10) 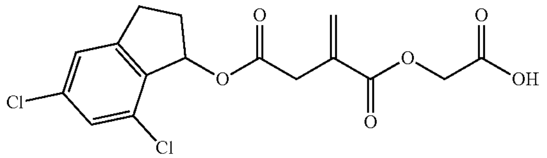 2-((4-((5,7-dichloro-2,3-dihydro-1H-inden-1-yl)oxy)-2-methylene-4-oxobutanoyl)oxy)acetic acid (Enantiomer 1) | LCMS (System 2, Method B) m/z 394.9/396.9 $(M + Na)^+$ $(ES^+)$. $^1H$ NMR (400 MHz, DMSO-d6) δ: 13.08 (br, 1H), 7.47 (d, J = 1.8 Hz, 1H), 7.42 (d, J = 1.8 Hz, 1H), 6.28 (d, J = 1.2 Hz, 1H), 6.19 (dd, J = 7.0, 2.2 Hz, 1H), 5.94 (d, J = 1.3 Hz, 1H), 4.63 (d, J = 2.8 Hz, 2H), 3.38 (s, 2H), 3.16-3.03 (m, 1H), 2.98-2.86 (m, 1H), 2.50-2.38 (m, 1H), 2.05-1.94 (m, 1H). |

-continued

| Example No. | Alcohol used in step 1/Example Structure/Name | LCMS/$^1$H NMR data |
|---|---|---|
| 9 | 5,7-dichloro-2,3-dihydro-1H-inden-1-ol Enantiomer 2 (Intermediate 11)<br>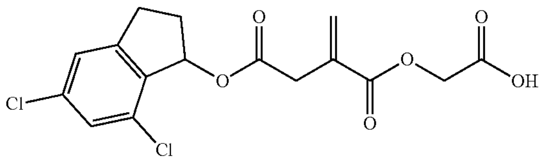<br>2-((4-((5,7-dichloro-2,3-dihydro-1H-inden-1-yl)oxy)-2-methylene-4-oxobutanoyl)oxy)acetic acid (Enantiomer 2) | LCMS (System 2, Method B) m/z 395.0/396.9 $(M + Na)^+$ $(ES^+)$. $^1$H NMR (400 MHz, DMSO-d6) δ: 13.10 (br, 1H), 7.47 (d, J = 1.8 Hz, 1H), 7.42 (d, J = 1.7 Hz, 1H), 6.28 (d, J = 1.1 Hz, 1H), 6.19 (dd, J = 7.0, 2.2 Hz, 1H), 5.94 (s, 1H), 4.63 (d, J = 2.8 Hz, 2H), 3.38 (s, 2H), 3.15-3.03 (m, 1H), 2.98-2.86 (m, 1H), 2.50-2.38 (m, 1H), 2.06-1.94 (m, 1H). |
| 12 | 5-bromo-6-methoxy-2,3-dihydro-1H-inden-1-ol Enantiomer 1 (Intermediate 14)<br>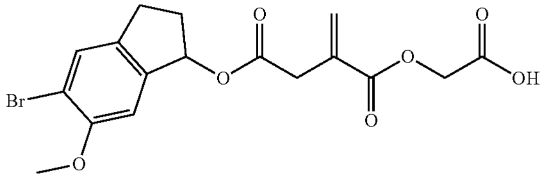<br>2-((4-((5-bromo-6-methoxy-2,3-dihydro-1H-inden-1-yl)oxy)-2-methylene-4-oxobutanoyl)oxy)acetic acid (Enantiomer 1) | LCMS (System 2, Method B) m/z 435.0/437.0 $(M + Na)^+$ $(ES^+)$. $^1$H NMR (400 MHz, DMSO-d6) δ: 13.10 (br, 1H), 7.52 (s, 1H), 7.02 (s, 1H), 6.29 (d, J = 1.2 Hz, 1H), 6.06 (dd, J = 7.2, 4.1 Hz, 1H), 5.94 (d, J = 1.2 Hz, 1H), 4.63 (d, J = 1.5 Hz, 2H), 3.80 (s, 3H), 3.41 (s, 2H), 2.99-2.86 (m, 1H), 2.83-2.71 (m, 1H), 2.50-2.38 (m, 1H), 2.04-1.91 (m, 1H). |
| 13 | 5-bromo-6-methoxy-2,3-dihydro-1H-inden-1-ol Enantiomer 2 (Intermediate 15)<br>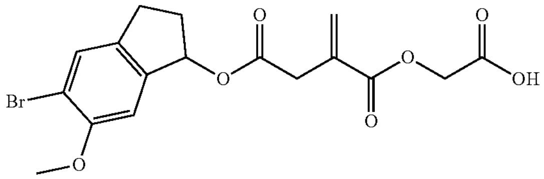<br>2-((4-((5-bromo-6-methoxy-2,3-dihydro-1H-inden-1-yl)oxy)-2-methylene-4-oxobutanoyl)oxy)acetic acid (Enantiomer 2) | LCMS (System 2, Method B) m/z 435.0/436.9 $(M + Na)^+$ $(ES^+)$. $^1$H NMR (400 MHz, DMSO-d6) δ: 13.09 (br, 1H), 7.52 (s, 1H), 7.02 (s, 1H), 6.29 (d, J = 1.2 Hz, 1H), 6.06 (dd, J = 7.1, 4.1 Hz, 1H), 5.94 (d, J = 1.2 Hz, 1H), 4.63 (d, J = 1.5 Hz, 2H), 3.80 (s, 3H), 3.41 (s, 2H), 2.99-2.87 (m, 1H), 2.83-2.71 (m, 1H), 2.50-2.38 (m, 1H), 2.04-1.92 (m, 1H). |
| 15 | 4-bromo-6-fluoro-2,3-dihydro-1H-inden-1-ol Enantiomer 1 (Intermediate 17)<br>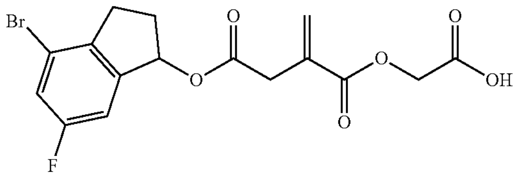<br>2-((4-((4-bromo-6-fluoro-2,3-dihydro-1H-inden-1-yl)oxy)-2-methylene-4-oxobutanoyl)oxy)acetic acid (Enantiomer 1) | LCMS (System 2, Method B) m/z 422.6/424.6 $(M + Na)^+$ $(ES^+)$. $^1$H NMR (400 MHz, DMSO-d6) δ: 13.12 (br, 1H), 7.53 (dd, J = 8.8, 2.4 Hz, 1H), 7.17 (dd, J = 8.3, 2.3 Hz, 1H), 6.29 (s, 1H), 6.16 (dd, J = 7.3, 4.5 Hz, 1H), 5.94 (d, J = 1.2 Hz, 1H), 4.63 (s, 2H), 3.42 (s, 2H), 2.99-2.87 (m, 1H), 2.85-2.74 (m, 1H), 2.57-2.49 (m, 1H), 2.08-1.96 (m, 1H). |
| 16 | 4-bromo-6-fluoro-2,3-dihydro-1H-inden-1-ol Enantiomer 2 | LCMS (System 2, Method B) m/z 422.8/424.8 $(M + Na)^+$ $(ES^+)$. |

Example 7—2-((4-((5-chloro-2-methyl-2,3-dihydro-1H-inden-2-yl)oxy)-2-methylene-4-oxobutanoyl)oxy)acetic acid

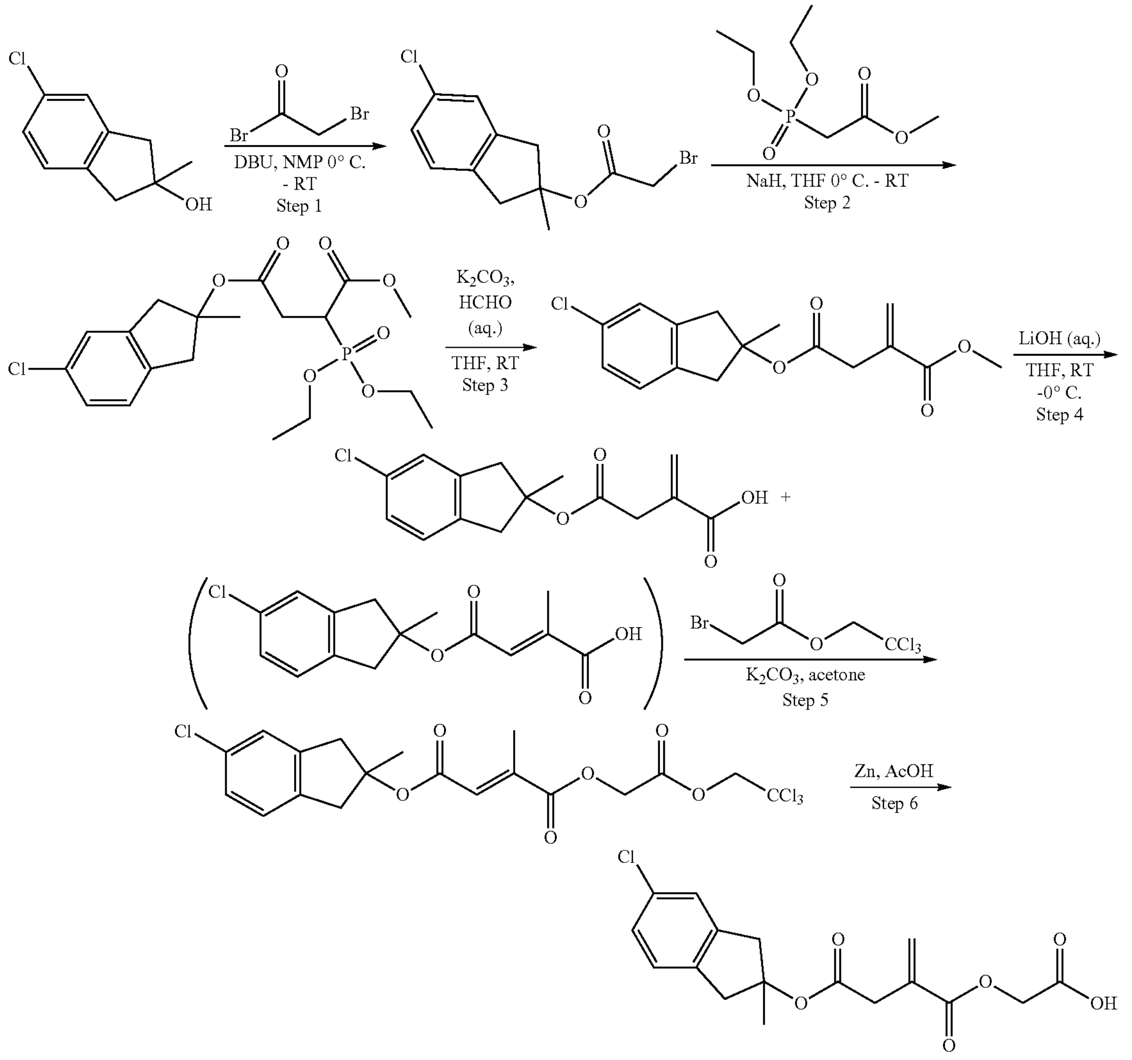

Step 1

To a solution of 5-chloro-2-methyl-2,3-dihydro-1H-inden-2-ol (Intermediate 9, 690 mg, 3.78 mmol) and DBU (862 mg, 5.67 mmol) in 1-methyl-2-pyrrolidinone (10 mL) at 0° C. was slowly added 2-bromoacetyl bromide (1.14 g, 5.67 mmol) dropwise and the mixture was stirred at room temperature for 16 h. The reaction mixture was then diluted with water (10 mL) and MTBE (10 mL), the phases were separated, and the aqueous layer was extracted with MTBE (2×10 mL). The combined organic layers were washed with brine, dried over $Na_2SO_4$, filtered and concentrated under reduced pressure at 40° C. The residue was purified by flash column chromatography (25 g $SiO_2$, 0-6% MTBE/petroleum ether) to give 5-chloro-2-methyl-2,3-dihydro-1H-inden-2-yl 2-bromoacetate (420 mg, 1.38 mmol, 37%) as a colorless oil. $^1H$ NMR (400 MHz, $CDCl_3$) δ: 7.19-7.07 (m, 3H), 3.76 (s, 2H), 3.39 (dd, J=16.7, 9.9 Hz, 2H), 3.14 (dd, J=16.7, 7.3 Hz, 2H), 1.68 (s, 3H).

Step 2

To a solution of methyl 2-(diethoxyphosphoryl)acetate (319 mg, 1.52 mmol) in THF (6 mL) at 0° C. was added NaH suspension in mineral oil (60 wt. %, 61 mg, 1.52 mmol), and the reaction mixture was stirred at 0° C. for 0.5 h. A solution of 5-chloro-2-methyl-2,3-dihydro-1H-inden-2-yl 2-bromoacetate (420 mg, 1.38 mmol) in THF (2 mL) was then added, and the reaction mixture was stirred at room temperature overnight. The reaction mixture was quenched with saturated aqueous $NH_4Cl$ solution, the phases were separated and the aqueous phase was extracted with EtOAc (2×10 mL). The combined organic layers were washed with brine, dried over $Na_2SO_4$, filtered and concentrated under reduced pressure at 30° C. to give 4-(5-chloro-2-methyl-2,3-dihydro-1H-inden-2-yl) 1-methyl 2-(diethoxyphosphoryl)succinate (500 mg, 1.16 mmol, 84%) as a colorless oil. The crude product was used directly in the next step. LCMS: (System 2, Method C) m/z 455.0/457.0 $(M+Na)^+$ $(ES^+)$.

Step 3

To a mixture of 4-(5-chloro-2-methyl-2,3-dihydro-1H-inden-2-yl) 1-methyl 2-(diethoxyphosphoryl)succinate (500 mg, 1.16 mmol) and potassium carbonate (247 mg, 1.78 mmol) in THF (5 mL) was added formaldehyde solution in water (37 wt. %, 4.8 mL, 5.95 mmol) at room temperature, and the reaction mixture was stirred at room temperature for 2 h. The reaction mixture was diluted with $H_2O$ (5 mL), the phases were separated and the aqueous phase was extracted with MTBE (2×10 mL). The combined organic layers were washed with $H_2O$ (2×5 mL) and brine, dried over $Na_2SO_4$, filtered and concentrated under reduced pressure at 30° C. The residue was purified by flash column chromatography (25 g $SiO_2$, 0-10% MTBE/petroleum ether) to give 4-(5-chloro-2-methyl-2,3-dihydro-1H-inden-2-yl) 1-methyl 2-methylenesuccinate (270 mg, 0.87 mmol, 75%) as a colorless oil. LCMS: (System 2, Method B) m/z 331.0/333.0 $(M+Na)^+$ $(ES^+)$.

Step 4

To a solution of 4-(5-chloro-2-methyl-2,3-dihydro-1H-inden-2-yl) 1-methyl 2-methylenesuccinate (270 mg, 0.87 mmol) in THF (3 mL) was added LiOH solution in water (2 M, 0.9 mL, 1.74 mmol), and the reaction mixture was stirred at room temperature for 5 h and at 0° C. for 16 h. The solvent was removed under reduced pressure at 30° C., and the residue was diluted with water (5 mL) and washed with MTBE (2×10 mL). The separated aqueous layer was acidified to pH=3 using dilute aqueous HCl (0.5 M) and extracted with MTBE (3×10 mL). The combined organic layers were washed with brine, dried over $Na_2SO_4$, filtered and concentrated under reduced pressure at 30° C. to give a 4:1 mixture of 4-((5-chloro-2-methyl-2,3-dihydro-1H-inden-2-yl)oxy)-2-methylene-4-oxobutanoic acid and (E)-4-((5-chloro-2-methyl-2,3-dihydro-1H-inden-2-yl)oxy)-2-methyl-4-oxobut-2-enoic acid (200 mg, 0.68 mmol, 77%) as a pale yellow oil, which was used directly in the next step. LCMS: (System 2, Method C) m/z 317.2/319.2 $(M+Na)^+$ $(ES^+)$.

Step 5

To a solution of a 4:1 mixture of 4-((5-chloro-2-methyl-2,3-dihydro-1H-inden-2-yl)oxy)-2-methylene-4-oxobutanoic acid and (E)-4-((5-chloro-2-methyl-2,3-dihydro-1H-inden-2-yl)oxy)-2-methyl-4-oxobut-2-enoic acid (200 mg, 0.68 mmol), and potassium carbonate (141 mg, 1.02 mmol) in acetone (5 mL) was added 2,2,2-trichloroethyl 2-bromoacetate (184 mg, 0.68 mmol), and the reaction mixture was stirred at room temperature overnight. The reaction mixture was filtered and the filtrate was concentrated under reduced pressure at 30° C. The residue was purified by flash column chromatography (25 g $SiO_2$, 0-10% MTBE/petroleum ether) to give 4-(5-chloro-2-methyl-2,3-dihydro-1H-inden-2-yl) 1-(2-oxo-2-(2,2,2-trichloroethoxy)ethyl) 2-methylenesuccinate (200 mg, 0.41 mmol, 61%) as a pale yellow oil. LCMS: (System 2, Method C) m/z 504.9/507.0/508.8 $(M+Na)^+$ $(ES^+)$.

Step 6

To a solution of 4-(5-chloro-2-methyl-2,3-dihydro-1H-inden-2-yl) 1-(2-oxo-2-(2,2,2-trichloroethoxy)ethyl) 2-methylenesuccinate (200 mg, 0.41 mmol) in AcOH (2 mL) was added zinc powder (133 mg, 2.05 mmol), and the reaction mixture was stirred at room temperature for 2 days. The reaction mixture was diluted with acetonitrile (5 mL), filtered and the filtrate was concentrated under reduced pressure at 15° C. The residue was diluted with ethyl acetate (5 mL) and water (5 mL), the phases were separated and the aqueous layer was extracted with ethyl acetate (2×5 mL). The combined ethyl acetate layers were concentrated under reduced pressure at 15° C., and the residue was purified by preparative HPLC (Column: Waters X-Bridge C18 OBD 10 μm 19×250 mm; Flow Rate: 20 mL/min; solvent system: MeCN/0.2% formic acid/water; gradient: 45-95% MeCN; collection wavelength: 214 nm). The collected fractions were concentrated under reduced pressure at 15° C. to remove MeCN, and the residue was lyophilized to give 2-((4-((5-chloro-2-methyl-2,3-dihydro-1H-inden-2-yl)oxy)-2-methylene-4-oxobutanoyl)oxy)acetic acid (26 mg, 0.074 mmol, 18%) as a colorless oil. LCMS: (System 2, Method B) m/z 375.0/377.0 $(M+Na)^+$ $(ES^+)$. $^1H$ NMR (400 MHz, $CDCl_3$) δ: 7.17-7.05 (m, 3H), 6.42 (s, 1H), 5.78 (s, 1H), 4.71 (s, 2H), 3.41-3.29 (m, 4H), 3.10 (dd, J=16.7, 6.7 Hz, 2H), 1.63 (s, 3H). One exchangeable proton not observed.

Example 14—3-((4-((4,6-dichloro-2,3-dihydro-1H-inden-1-yl)oxy)-2-methylene-4-oxobutanoyl)oxy) propanoic acid (Enantiomer 1)

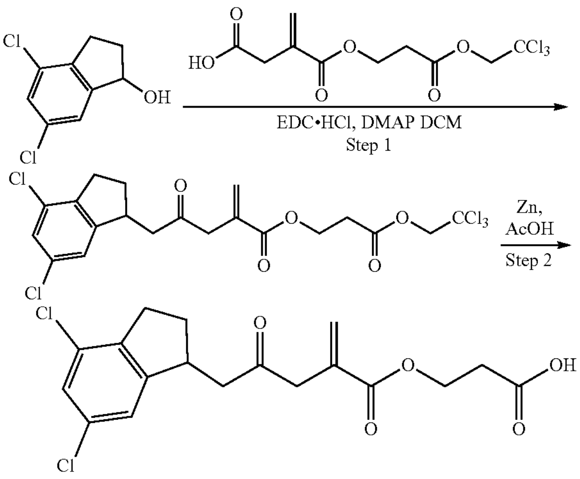

Step 1

To a solution of 3-((3-oxo-3-(2,2,2-trichloroethoxy) propoxy)carbonyl)but-3-enoic acid (Intermediate 16, 400 mg, 1.20 mmol), 4,6-dichloro-2,3-dihydro-1H-inden-1-ol Enantiomer 1 (Intermediate 3, 202 mg, 1.00 mmol) and DMAP (98 mg, 0.80 mmol) in DCM (5 mL) at 0° C. was added EDC·HCl (288 mg, 1.50 mmol), and the resulting pale-yellow mixture was stirred at room temperature for 20 min. The mixture was quenched with dilute aqueous HCl and adjusted to pH=6, the phases were separated, and the aqueous phase was extracted with DCM (2×5 mL). The separated organic layers were washed with brine, dried over $Na_2SO_4$ and filtered. The filtrate was concentrated under reduced pressure at 25° C., and the residue was purified by flash column chromatography (12 g silica, 0-10% MTBE/petroleum ether) to give 4-(4,6-dichloro-2,3-dihydro-1H-inden-1-yl) 1-(3-oxo-3-(2,2,2-trichloroethoxy)propyl) 2-methylenesuccinate Enantiomer 1 (320 mg, 0.62 mmol, 61%) as a yellow oil. LCMS: (System 2, Method C) m/z 538.6/540.6/542.6 $(M+Na)^+$ $(ES^+)$.

Step 2

A mixture of 4-(4,6-dichloro-2,3-dihydro-1H-inden-1-yl) 1-(3-oxo-3-(2,2,2-trichloroethoxy)propyl) 2-methylenesuccinate Enantiomer 1 (320 mg, 0.62 mmol) and zinc powder (283 mg, 4.32 mmol) in AcOH (3 mL) was stirred at room temperature for 2 days. The mixture was filtered, and the filtrate was concentrated under reduced pressure at 25° C. and the residue was purified by preparative HPLC (Column: Waters X-Bridge C18 OBD 10 μm 19×250 mm; Flow Rate: 20 mL/min; solvent system: MeCN/0.2% formic acid/water; gradient: 55-95% MeCN; collection wavelength: 214 nm). The collected fractions were concentrated under reduced pressure at 25° C. to remove MeCN, and the residue was lyophilized to give 3-((4-((4,6-dichloro-2,3-dihydro-1H-inden-1-yl)oxy)-2-methylene-4-oxobutanoyl)oxy)propanoic acid (Enantiomer 1) (98 mg, 0.25 mmol, 41%) as a colorless oil. LCMS: (System 2, Method B) m/z 408.8/410.8 $(M+Na)^+$ $(ES^+)$. $^1H$ NMR (400 MHz, DMSO-d6) δ: 12.37 (br, 1H), 7.57 (d, J=1.9 Hz, 1H), 7.34 (d, J=1.8 Hz, 1H), 6.17 (d, J=1.3 Hz, 1H), 6.14 (dd, J=7.3, 4.4 Hz, 1H), 5.85 (d, J=1.4 Hz, 1H), 4.31-4.18 (m, 2H), 3.38 (s, 2H), 3.04-2.92 (m, 1H), 2.91-2.79 (m, 1H), 2.58 (t, J=6.2 Hz, 2H), 2.54-2.52 (m, 1H), 2.09-1.95 (m, 1H).

Example 21—2-((4-((5,6-dichloro-2-methyl-2,3-dihydro-1H-inden-2-yl)oxy)-2-methylene-4-oxobutanoyl)oxy)acetic acid

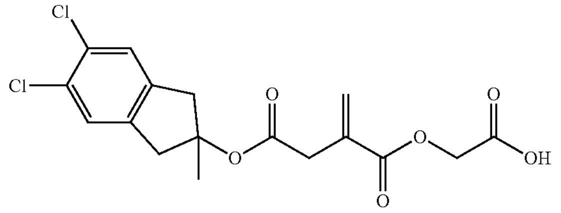 [SMILES: C=C(CC(=O)OC1(C)Cc2cc(Cl)c(Cl)cc2C1)C(=O)OCC(=O)O]

Prepared by an analogous method to Example 7 starting from 5,6-dichloro-2-methyl-2,3-dihydro-1H-inden-2-ol (Intermediate 23, 660 mg, 3.04 mmol), except that in Step 4 IPA was used as solvent in place of THF. The crude product was purified by preparative HPLC (Column: Waters X-Bridge C18 OBD 10 μm 19×250 mm; Flow Rate: 20 mL/min; solvent system: MeCN/0.2% formic acid/water; gradient: 58-95% MeCN; collection wavelength: 214 nm). The collected fractions were concentrated under reduced pressure at 15° C. to remove MeCN, and the residue was lyophilized to give 2-((4-((5,6-dichloro-2-methyl-2,3-dihydro-1H-inden-2-yl)oxy)-2-methylene-4-oxobutanoyl)oxy)acetic acid (58 mg, 0.15 mmol) as a white solid. LCMS: (System 2, Method B) m/z 408.9/410.8 $(M+Na)^+$ $(ES^+)$. $^1H$ NMR (400 MHz, DMSO-d6) δ: 13.02 (br, 1H), 7.49 (s, 2H), 6.24 (d, J=1.2 Hz, 1H), 5.87 (d, J=1.3 Hz, 1H), 4.57 (s, 2H), 3.30 (s, 2H), 3.28 (d, J=17.1 Hz, 2H), 3.09 (d, J=17.0 Hz, 2H), 1.56 (s, 3H).

Example 22—(3R)-3-((4-((4,6-dichloro-2,3-dihydro-1H-inden-1-yl)oxy)-2-methylene-4-oxobutanoyl)oxy)-4,4,4-trifluorobutanoic acid (Diastereomer A)

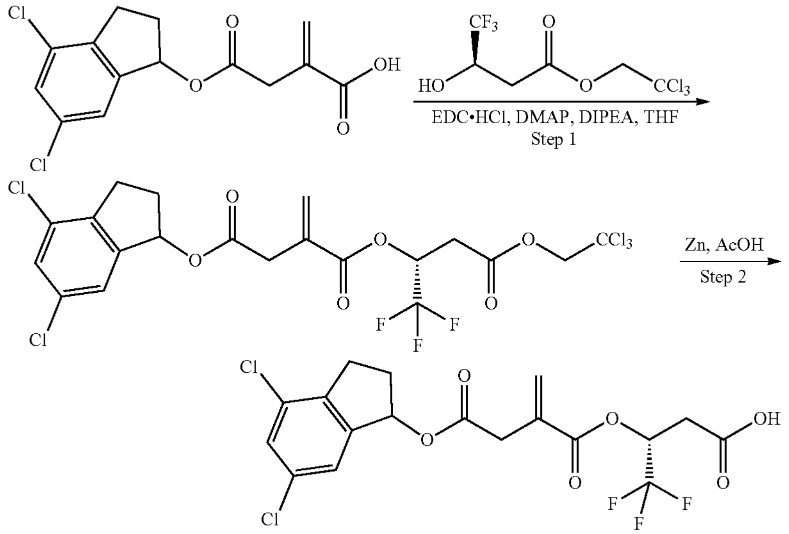

Step 1

To a solution of 4-((4,6-dichloro-2,3-dihydro-1H-inden-1-yl)oxy)-2-methylene-4-oxobutanoic acid Enantiomer 1 (Intermediate 25, 330 mg, 1.05 mmol), 2,2,2-trichloroethyl (R)-4,4,4-trifluoro-3-hydroxybutanoate (Intermediate 29, 302 mg, 1.05 mmol), DMAP (102 mg, 0.84 mmol) and EDC·HCl (302 mg, 1.58 mmol) in THF (5 mL) at 0° C. was added DIPEA (406 mg, 3.15 mmol), and the resulting pale-yellow mixture was stirred at room temperature for 6 h. The reaction mixture was adjusted to pH=5 with dilute aqueous HCl (0.5 M), the phases were separated, and the aqueous layer was extracted with EtOAc (2×5 mL). The combined organic phases were washed with brine, dried over $Na_2SO_4$ and filtered. The filtrate was concentrated under reduced pressure at 25° C., and the residue was purified by flash column chromatography (12 g silica, 0-10% MTBE/petroleum ether) to give 4-(4,6-dichloro-2,3-dihydro-1H-inden-1-yl) 1-((R)-1,1,1-trifluoro-4-oxo-4-(2,2,2-trichloroethoxy)butan-2-yl) 2-methylenesuccinate Diastereomer A (200 mg, 0.34 mmol, 32%) as a yellow oil. LCMS: (System 2, Method C) m/z 606.5/608.6 $(M+Na)^+$ $(ES^+)$.

Step 2

A mixture of 4-(4,6-dichloro-2,3-dihydro-1H-inden-1-yl) 1-((R)-1,1,1-trifluoro-4-oxo-4-(2,2,2-trichloroethoxy)butan-2-yl) 2-methylenesuccinate Diastereomer A (200 mg, 0.34 mmol) and zinc powder (155 mg, 2.38 mmol) in AcOH (2 mL) was stirred at room temperature for 20 h. The reaction mixture was filtered, and the filtrate was quenched with $H_2O$ (2 mL), the phases were separated and the aqueous phase was extracted with EtOAc (2×5 mL). The combined organic layers were washed with brine, dried over $Na_2SO_4$ and filtered. The mixture was concentrated under reduced pressure at 25° C. and the residue was purified by preparative HPLC (Column: Waters Sunfire Prep C18 OBD 10 μm 19×250 mm; Flow Rate: 20 mL/min; solvent system: MeCN/0.2% formic acid/water; gradient: 60-95% MeCN;

collection wavelength: 214 nm). The collected fractions were concentrated under reduced pressure at 25° C. to remove MeCN, and the residue was lyophilized to give (3R)-3-((4-((4,6-dichloro-2,3-dihydro-1H-inden-1-yl)oxy)-2-methylene-4-oxobutanoyl)oxy)-4,4,4-trifluorobutanoic acid (Diastereomer A) (98 mg, 0.22 mmol, 62%) as a colorless oil. LCMS: (System 2, Method B) m/z 476.8/478.8 $(M+Na)^+$ $(ES^+)$. $^1H$ NMR (400 MHz, DMSO-d6) δ: 12.83 (br, 1H), 7.57 (d, J=1.9 Hz, 1H), 7.32 (d, J=1.8 Hz, 1H), 6.31 (s, 1H), 6.13 (dd, J=7.3, 4.4 Hz, 1H), 5.99 (s, 1H), 5.82-5.71 (m, 1H), 3.44 (s, 2H), 3.03-2.91 (m, 2H), 2.90-2.80 (m, 1H), 2.79-2.69 (m, 1H), 2.57-2.45 (m, 1H), 2.07-1.96 (m, 1H).

Example 23—(3S)-3-((4-((4,6-dichloro-2,3-dihydro-1H-inden-1-yl)oxy)-2-methylene-4-oxobutanoyl)oxy)-4,4,4-trifluorobutanoic acid (Diastereomer B)

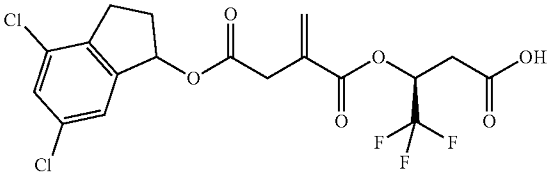 [SMILES: C=C(CC(=O)OC1CCc2c(Cl)cc(Cl)cc21)C(=O)O[C@@H](CC(=O)O)C(F)(F)F]

Prepared by an analogous procedure to Example 22 starting from 4-((4,6-dichloro-2,3-dihydro-1H-inden-1-yl)oxy)-2-methylene-4-oxobutanoic acid Enantiomer 1 (Intermediate 25, 350 mg, 1.11 mmol) and 2,2,2-trichloroethyl (S)-4,4,4-trifluoro-3-hydroxybutanoate (Intermediate 28, 320 mg, 1.11 mmol). The crude product was purified by preparative HPLC (Column: Waters Sunfire Prep C18 OBD 10 μm 19×250 mm; Flow Rate: 20 mL/min; solvent system: MeCN/0.2% formic acid/water; gradient: 60-95% MeCN; collection wavelength: 214 nm). The collected fractions were concentrated under reduced pressure at 25° C. to remove MeCN, and the residue was lyophilized to give (3S)-3-((4-((4,6-dichloro-2,3-dihydro-1H-inden-1-yl)oxy)-2-methylene-4-oxobutanoyl)oxy)-4,4,4-trifluorobutanoic acid (Diastereomer B) (54 mg, 0.15 mmol) as a colorless oil. LCMS: (System 2, Method B) m/z 476.8/478.8 $(M+Na)^+$ $(ES^+)$. $^1H$ NMR (400 MHz, DMSO-d6) δ: 12.90 (s, 1H), 7.57 (d, J=1.8 Hz, 1H), 7.34 (d, J=1.9 Hz, 1H), 6.31 (s, 1H), 6.13 (dd, J=7.3, 4.4 Hz, 1H), 5.99 (s, 1H), 5.82-5.72 (m, 1H), 3.44 (s, 2H), 3.02-2.90 (m, 2H), 2.90-2.80 (m, 1H), 2.80-2.70 (m, 1H), 2.56-2.44 (m, 1H), 2.06-1.95 (m, 1H).

Biological Example 1—THP-1 AlphaLISA IL-1β and IL-6 Cytokine Assay

Measuring Inhibitory Effects on IL-1β and IL-6 Cytokine Output from THP-1s

The cytokine inhibition profiles of compounds of formula (I) were determined in a differentiated THP-1 cell assay. All assays were performed in RPMI-1640 growth medium (Gibco), supplemented with 10% fetal bovine serum (FBS; Gibco), 1% penicillin-streptomycin and 1% sodium pyruvate unless specified otherwise. The IL-1β and IL-6 cytokine inhibition assays were each run in a background of differentiated THP-1 cells as described below. All reagents described were from Sigma-Aldrich unless specified otherwise. Compounds were prepared as 10 mM DMSO stocks.

Assay Procedure

THP-1 cells were expanded as a suspension up to 80% confluence in appropriate growth medium. Cells were harvested, suspended, and treated with an appropriate concentration of phorbol 12-myristate 13-acetate (PMA) over a 72 hr period (37° C./5% $CO_2$).

Following 72 hrs of THP-1 cell incubation, cellular medium was removed and replaced with fresh growth media containing 1% of FBS. Working concentrations of compounds were prepared separately in 10% FBS treated growth medium and pre-incubated with the cells for 30 minutes (37° C./5% $CO_2$). Following the 30 minute compound pre-incubation, THP-1s were treated with an appropriate concentration of LPS and the THP-1s were subsequently incubated for a 24 hr period (37° C./5% $CO_2$). An appropriate final concentration of Nigericin was then dispensed into the THP-1 plates and incubated for 1 hour (37° C./5% $CO_2$) before THP-1 supernatants were harvested and collected in separate polypropylene 96-well holding plates.

Reagents from each of the IL-1β and IL-6 commercial kits (Perkin Elmer) were prepared and run according to the manufacturer's instructions. Subsequently, fluorescence signal detection in a microplate reader was measured (EnVision® Multilabel Reader, Perkin Elmer).

Percentage inhibition was calculated per cytokine by normalising the sample data to the high and low controls used within each plate (+/− LPS respectively). Percentage inhibition was then plotted against compound concentration and the 50% inhibitory concentration ($IC_{50}$) was determined from the resultant concentration-response curve.

A number of Example compounds of formula (I) were tested and the results are shown in Table 1 below. Dimethyl itaconate and dimethyl fumarate were included as comparator compounds.

TABLE 1

THP-1 cell IL-1β and IL-6 $IC_{50}$ values (μM)

| Compound | IL-1β ($IC_{50}$) | IL-6 ($IC_{50}$) |
|---|---|---|
| dimethyl fumarate | 14.4 | 9.3 |
| dimethyl itaconate | >100 | >100 |
| Example 1 | 29.2 | 10.2 |
| Example 2 | 4.0 | 4.3 |
| Example 3 | 5.6 | 3.6 |
| Example 4 | 12.0 | 4.6 |
| Example 5 | 12.3 | NT* |
| Example 6 | 9.9 | NT |
| Example 7 | >31.6 | 8.2 |
| Example 8 | 10.6 | NT |
| Example 9 | 11.7 | NT |
| Example 10 | 6.6 | NT |
| Example 11 | 6.1 | NT |
| Example 12 | 46.4 | NT |
| Example 13 | 34.9 | NT |
| Example 14 | 2.8 | NT |
| Example 15 | 2.4 | NT |
| Example 16 | 2.6 | NT |
| Example 17 | 2.8 | NT |
| Example 18 | 2.1 | NT |
| Example 19 | 2.2 | NT |
| Example 20 | 1.4 | 3.9 |
| Example 21 | 7.9 | 3.2 |
| Example 22 | 1.7 | 1.2 |
| Example 23 | 1.2 | 1.2 |
| Example 24 | 3.3 | 4.1 |
| Example 25 | 4.8 | 6.2 |
| Example 26 | 7.9 | 3.0 |
| Example 27 | 11.9 | 8.6 |
| Example 28 | 11.7 | 7.6 |
| Example 29 | 11.4 | 5.8 |
| Example 30 | 7.9 | 20.6 |
| Example 31 | 9.6 | 9.6 |

NT* = not tested

All compounds of formula (I) shown in Table 1 exhibited improved cytokine-lowering potencies compared to dimethyl itaconate as shown by the IL-1β and IL-6 values (where measured). Preferred compounds shown in Table 1 exhibited improved cytokine-lowering potencies compared to dimethyl fumarate for IL-1β and IL-6.

A number of Example compounds of formula (XVI) were tested and the results are shown in Table 2 below. Dimethyl itaconate was included as a comparator compound.

TABLE 2

| THP-1 cell IL-1β values (μM) | |
|---|---|
| Compound | IL-1β ($IC_{50}$) |
| dimethyl itaconate | >100 |
| Intermediate 25 | 43.2 |
| Intermediate 37 | 18.3 |
| Intermediate 40 | 5.3 |
| Intermediate 41 | 31.7 |

All compounds of formula (XVI) shown in Table 2 exhibited improved cytokine-lowering potencies compared to dimethyl itaconate as shown by the lower IL-1β $IC_{50}$ values.

Biological Example 2—NRF2+/−GSH Activation Assay

Measuring Compound Activation Effects on the Anti-Inflammatory Transcription Factor NRF2 in DiscoverX PathHunter NRF2 Translocation Kit Potency and efficacy of compounds of formula (I) against the target of interest to activate NRF2 (nuclear factor erythroid 2-related factor 2) were determined using the PathHunter NRF2 translocation kit (DiscoverX). The NRF2 translocation assay was run using an engineered recombinant cell line, utilising enzyme fragment complementation to determine activation of the Keap1-NRF2 protein complex and subsequent translocation of NRF2 into the nucleus. Enzyme activity was quantified using a chemiluminescent substrate consumed following the formation of a functional enzyme upon PK-tagged NRF2 translocation into the nucleus.

The assay was run under either +/−GSH (glutathione) conditions to determine the attenuating activities of GSH against target compounds.

Additionally, a defined concentration of dimethyl fumarate was used as the 'High' control to normalise test compound activation responses to.

Assay Procedure

U2OS PathHunter eXpress cells were thawed from frozen prior to plating. Following plating, U2OS cells were incubated for 24 hrs (37° C./5% $CO_2$) in commercial kit provided cell medium.

Following 24 hrs of U2OS incubation, cells were directly treated with an appropriate final concentration of compound, for −GSH conditions, or for +GSH conditions, an intermediate plate containing 6× working concentrations of compound stocks was prepared in a 6 mM working concentration of GSH solution (solubilised in sterile PBS). Following a 30 minute compound-GSH pre-incubation (37° C./5% $CO_2$) for +GSH treatment, plated U2OS cells were incubated with an appropriate final concentration of compound and GSH.

Following compound (+/−GSH) treatment, the U2OS plates were incubated for a further 6 hours (37° C./5% $CO_2$) before detection reagent from the PathHunter NRF2 commercial kit was prepared and added to test plates according to the manufacturer's instructions. Subsequently, the luminescence signal detection in a microplate reader was measured (PHERAstar®, BMG Labtech).

Percentage activation was calculated by normalising the sample data to the high and low controls used within each plate (+/−DMF). Percentage activation/response was then plotted against compound concentration and the 50% activation concentration ($EC_{50}$) was determined from the plotted concentration-response curve.

A number of compounds of formula (I) were tested in this assay, and the results are shown in Table 3 below. Dimethyl itaconate and dimethyl fumarate were included as comparator compounds.

TABLE 3

| NRF2 activation | | | | |
|---|---|---|---|---|
| | −GSH | | +GSH | |
| Compound | $EC_{50}$ (μM) | $E_{max}$ (%) | $EC_{50}$ (μM) | $E_{max}$ (%) |
| dimethyl fumarate | 6.0 | 100 | >100 | 19 |
| dimethyl itaconate | 21.4 | 137 | 56.4 | 77 |
| Example 1 | 25.6 | 139 | 34.6 | 125 |
| Example 2 | 9.0 | 196 | 11.4 | 166 |
| Example 3 | 9.8 | 229 | 15.8 | 211 |
| Example 4 | 7.5 | 196 | 16.5 | 182 |
| Example 5 | 10.8 | 280 | 19.5 | 246 |
| Example 6 | 8.3 | 242 | 17.4 | 215 |
| Example 7 | 14.5 | 155 | 22.3 | 135 |
| Example 8 | 4.8 | 268 | 16.4 | 264 |
| Example 9 | 8.1 | 244 | 20.6 | 204 |
| Example 14 | 27.8 | 193 | 36.7 | 118 |
| Example 17 | 29.2 | 305 | 35.4 | 184 |
| Example 18 | 8.7 | 121 | 18.4 | 105 |
| Example 19 | 18.1 | 224 | 10.1 | 48 |
| Example 20 | 12.9 | 234 | 31.8 | 155 |
| Example 21 | 5.6 | 151 | 4.0 | 55 |
| Example 24 | 6.0 | 148 | 5.7 | 84 |
| Example 25 | 6.0 | 205 | 10.6 | 147 |
| Example 26 | 4.1 | 216 | 7.7 | 145 |
| Example 27 | 12.2 | 157 | 35.1 | 139 |
| Example 27 (further measurement) | 22.2 | 201 | 37.5 | 136 |
| Example 28 | 8.0 | 160 | 22.5 | 139 |
| Example 29 | 5.9 | 147 | 18.7 | 141 |
| Example 29 (further measurement) | 11.5 | 211 | 25.9 | 175 |
| Example 30 | 21.6 | 225 | 28.7 | 182 |
| Example 31 | 11.3 | 141 | 22.9 | 137 |

All compounds of formula (I) shown in Table 3 exhibited a lower $EC_{50}$ and/or a higher $E_{max}$ compared with dimethyl fumarate and/or dimethyl itaconate (where tested) in the −GSH assay. All compounds of formula (I) in Table 3 that were tested exhibited a lower $EC_{50}$ and a higher $E_{max}$ compared with dimethyl fumarate in the +GSH assay, i.e., unlike dimethyl fumarate, the NRF2-activating properties of the compounds of formula (I) are largely retained in the presence of glutathione (GSH).

Biological Example 3—Hepatocyte Stability Assay

Defrosted cryo-preserved hepatocytes (viability >70%) were used to determine the metabolic stability of a compound via calculation of intrinsic clearance ($Cl_{int}$; a measure of the removal of a compound from the liver in the absence of blood flow and cell binding). Clearance data are particularly important for in vitro work as they can be used in combination with in vivo data to predict the half-life and oral bioavailability of a drug.

The metabolic stability in hepatocytes assay involves a time-dependent reaction using both positive and negative controls. The cells were pre-incubated at 37° C. and spiked with test compound (and positive control); samples were taken at pre-determined time intervals were analysed to monitor the change in concentration of the initial drug compound over 60 minutes. A buffer incubation reaction (with no hepatocytes present) acted as a negative control and two cocktail solutions, containing compounds with known high and low clearance values (verapamil/7-hydroxycoumarin and propranolol/diltiazem), acted as positive controls.

1. The assay was run with a cell concentration of $0.5\times10^6$ cells/mL in Leibovitz buffer.
2. All compounds and controls were run in duplicate.
3. Compound concentration was 10 μM.
4. All compounds and controls were incubated with both cells and buffer to show turnover was due to hepatic metabolism.
5. All wells on the incubation plate had 326.7 μL of either cells or buffer added.
6. Prior to assay, cell and buffer-only incubation plates were preincubated for 10 mins at 37° C.
7. The assay was initiated by adding compounds, 3.3 μL of 1 mM in 10% DMSO-90% Buffer; final DMSO concentration was 0.1%.
8. Samples were taken at regular timepoints (0, 5, 10, 20, 40, 60 min) until 60 mins.
9. Sample volume was 40 μL and was added to 160 μL of crash solvent (acetonitrile with internal standard) and stored on ice.
10. At the end of the assay, the crash plates were centrifuged at 3500 rpm for 20 mins at 4° C.
11. 80 μL of clear supernatant was removed and mixed with 80 μL of deionised water before being analysed by LC-MS/MS.

Raw LC-MS/MS data was exported to, and analysed in, Microsoft Excel for determination of intrinsic clearance. The percentage remaining of a compound was monitored using the peak area of the initial concentration as 100%. Intrinsic clearance and half-life values were calculated using a graph of the natural log of percentage remaining versus the time of reaction in minutes. Half-life (min) and intrinsic clearance ($Cl_{int}$ in μL $min^{-1}$ $10^{-6}$ cells) values were calculated using the gradient of the graph (the elimination rate constant, k) and Equations 1 and 2.

$$t_{\frac{1}{2}} = \frac{\ln 2}{k} \qquad \text{\{Equation 1\}}$$

$$Cl_{int} = \left(\frac{\ln 2}{t_{\frac{1}{2}}}\right) \times \left(\frac{350}{0.175}\right) \qquad \text{\{Equation 2\}}$$

A number of compounds of formula (I) were tested in this assay, and the results are shown in Table 4 below. 4-Octyl itaconate was included as a comparator compound.

TABLE 4

Hepatocyte stability

| Compound | Species | $Cl_{int}$ (μL $min^{-1}$ $10^{-6}$ cells) | T½ (min) |
|---|---|---|---|
| 4-octyl itaconate | Human | 401 | 4 |
| | Mouse | 351 | 4 |
| Example 1 | Human | 3 | 449 |
| | Mouse | 46 | 41 |
| Example 2 | Human | 13 | 116 |
| | Mouse | 51 | 37 |
| Example 3 | Human | 16 | 93 |
| | Mouse | >460 | <3 |
| Example 4 | Human | 13 | 119 |
| | Mouse | 83 | 16 |
| Example 5 | Human | 11 | 140 |
| | Mouse | 431 | 3 |
| Example 6 | Human | 8 | 207 |
| | Mouse | 69 | 19 |
| Example 7 | Human | 17 | 86 |
| | Mouse | 142 | 10 |
| Example 8 | Human | 15 | 106 |
| | Mouse | 316 | 4 |
| Example 9 | Human | 4 | 428 |
| | Mouse | 61 | 21 |
| Example 10 | Human | 18 | 81 |
| | Mouse | 225 | 7 |
| Example 11 | Human | 24 | 62 |
| | Mouse | 311 | 5 |
| Example 14 | Human | 19 | 75 |
| | Mouse | 224 | 7 |
| Example 15 | Human | 9 | 165 |
| | Mouse | 51 | 24 |
| Example 16 | Human | 15 | 95 |
| | Mouse | >460 | <3 |
| Example 17 | Human | 6 | 227 |
| | Mouse | 72 | 21 |
| Example 18 | Human | NT | NT |
| | Mouse | 146 | 10 |
| Example 19 | Human | 4 | 335 |
| | Mouse | 37 | 41 |
| Example 20 | Human | 11 | 125 |
| | Mouse | >460 | <3 |
| Example 21 | Human | 37 | 35 |
| | Mouse | 483 | 3 |
| Example 22 | Human | 252 | 7 |
| | Mouse | >460 | <3 |
| Example 23 | Human | 190 | 9 |
| | Mouse | >460 | <3 |
| Example 24 | Human | 54 | 32 |
| | Mouse | 56 | 34 |
| Example 25 | Human | 29 | 58 |
| | Mouse | >460 | <3 |
| Example 26 | Mouse | >460 | <3 |
| | Human | 9 | 166 |
| Example 27 | Mouse | 97 | 16 |
| | Human | 9 | 169 |
| Example 28 | Mouse | 49 | 32 |
| | Human | 21 | 75 |
| Example 29 | Mouse | 92 | 17 |
| | Human | 10 | 152 |
| Example 30 | Human | 19 | 81 |
| | Mouse | 393 | 4 |
| Example 31 | Human | 29 | 61 |
| | Mouse | 272 | 6 |

*NT means not tested in this assay

All compounds of formula (I) that are shown in Table 4 have improved metabolic stabilities compared with 4-octyl itaconate, as shown by their intrinsic clearance ($Cl_{int}$) and half-life ($T_{1/2}$) values in this assay in at least human hepatocytes (where tested). Preferred compounds exhibited lower intrinsic clearance ($Cl_{int}$) and longer half-life ($T_{1/2}$) values compared with 4-octyl itaconate in both human and mouse hepatocytes.

REFERENCES

The following publication cited in this specification are herein incorporated by reference in their entirety.

Ackermann et al. *Proc. Soc. Exp. Bio. Med.* 1949, 72(1), 1-9.
Andersen J. L. et al. *Nat. Commun.* 2018, 9, 4344.
Angiari S. and O'Neill L. A. *Cell Res.* 2018, 28, 613-615.
Bagavant G. et al. *Indian J. Pharm. Sci.* 1994, 56, 80-85.
Bambouskova M. et al. *Nature* 2018, 556, 501-504.
Blewett M. M. et al. *Sci. Sign.* 2016, 9 (445), rs10; 6.
Brennan M. S. et al. *PLoS One* 2015, 10, e0120254.
Brück J. et al. *Exp. Dermatol.* 2018, 27, 611-624.
Cocco M. et al. *J. Med. Chem.* 2014, 57, 10366-10382.
Cocco M. et al. *J. Med. Chem.* 2017, 60, 3656-3671.
Cordes T. et al. *J. Biol. Chem.* 2016, 291, 14274-14284.
Cordes T. et al. *Mol. Metab.* 2020, 32, 122-135.
Daly R. et al. *medRxiv* 2019, 19001594; doi: https://doi.org/10.1101/19001594.
Daniels B. P. et al. *Immunity* 2019, 50(1), 64-76.e4.
Dibbert S. et al. *Arch. Dermatol. Res.* 2013, 305, 447-451.
ElAzzouny M. et al. *J. Biol. Chem.* 2017, 292, 4766-4769.
Gillard G. O. et al. *J. Neuroimmunol.* 2015, 283, 74-85.
Gu L. et al. *Immunol. Cell Biol.* 2020 doi:10.1111/imcb.12316.
Hanke T. et al. *Pharmacol. Therapeut.* 2016, 157, 163-187.
Hunt T. et al. *Consortium of Multiple Sclerosis Centers* 2015 *Annual Meeting,* 27-30 May 2015, Indianapolis, IN, USA: Poster DX37.
Kornberg M. D. et al. *Science* 2018, 360, 449-453.
Kulkarni R. A. et al. *Nat. Chem. Biol.* 2019 10.1038/s41589-018-0217-y.
Lampropoulou V. et al. *Cell Metab.* 2016, 24, 158-166.
Lehmann J. C. U. et al. *J. Invest. Dermatol.* 2007, 127, 835-845.
Liao S.-T. et al. *Nat. Commun.* 2019, 10(1), 5091.
Liu H. et al. *Cell Commun. Signal.* 2018, 16, 81.
McGuire V. A. et al. *Sci. Rep.* 2016, 6, 31159.
Michelucci A. et al. *Proc. Natl. Acad. Sci. USA* 2013, 110, 7820-7825.
Mills E. A. et al. *Front. Neurol.* 2018, 9, 5.
Mills E. L. et al. *Cell* 2016, 167, 457-470.
Mills E. L. et al. *Nature* 2018, 556, 113-117.
Mrowietz U. et al. *Trends Pharmacol. Sci.* 2018, 39, 1-12.
Müller S. et al. *J. Dermatol. Sci.* 2017, 87, 246-251.
Murphy M. P. and O'Neill L. A. J. *Cell* 2018, 174, 780-784.
O'Neill L. A. J. and Artyomov M. N. *Nat. Rev. Immunol.* 2019 273-281.
Olagnier D. et al. *Nat. Commun.* 2018, 9, 3506.
Schmidt T. J. et al. *Bioorg. Med. Chem.* 2007, 15, 333-342.
Shan Q. et al. *Biochem. Biophys. Res. Commun.* 2019, 517, 538-544.
Straub R. H. and Schradin C. *Evol. Med. Public Health* 2016, 1, 37-51S.
Straub R. H. and Cutolo M. *Rheumatology* 2016, 55 (Suppl. 2), ii6-ii14.
Sun X. et al., *FASEB J.* 2019, 33, 12929-12940.
Tang C. et al. *Cell Physiol. Biochem.* 2018, 51, 979-990.
Tang C. et al. *Biochem. Biophys. Res. Commun.* 2019, 508, 921-927.
Tang H. et al. *Biochem. Biophys. Res. Commun.* 2008, 375, 562-565.
Tian et al. *Eur. J. Pharmacol.* 2020, 873, 172989.
van der Reest J. et al. *Nat. Commun.* 2018, 9, 1581.
von Glehn F. et al. *Mult. Scler. Relat. Disord.* 2018, 23, 46-50.
Yi F. et al. *Hepatology* 2020, 873, 172989.
Yu X.-H. et al. *Immunol. Cell Biol.* 2019, 97, 134-141.
Zhang S. et al. *Bioorg. Med. Chem.* 2012, 20, 6073-6079.
Zhang D. et al. *Int. Immunopharmacol.* 2019, 77, 105924.
Zhao C. et al. *Microb. Pathogen.* 2019, 133, 103541.
Zhao G. et al. *Biochem. Biophys. Res. Commun.* 2014, 448, 303-307.

MISCELLANEOUS

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. A compound of formula (I):

(I)

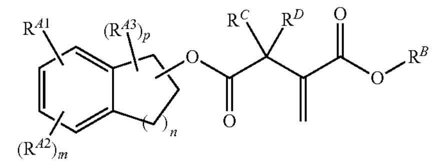

wherein:

$R^{A1}$ is selected from the group consisting of H, halo, $C_{1-4}$alkyl, $C_{1-4}$haloalkyl, $C_{1-4}$alkoxy, $C_{1-4}$haloalkoxy, —$SC_{1-4}$alkyl, —$SC_{1-4}$haloalkyl and $SF_5$;

$R^{A2}$ is selected from the group consisting of halo, $C_{1-4}$alkyl, $C_{1-4}$haloalkyl, $C_{1-4}$alkoxy and $C_{1-4}$haloalkoxy;

$R^{A3}$ is $C_{1-2}$alkyl;

m is 0, 1 or 2;

n is 1 or 2;

p is 0 or 1; and $R^B$ is selected from the group consisting of $CH_2COOH$, $CH_2CH_2COOH$, $CH_2$tetrazolyl and $CH_2CH_2$tetrazolyl, wherein $R^B$ is optionally substituted on an available carbon atom by one or more $R^{B1}$ wherein $R^{B1}$ is selected from the group consisting of difluoromethyl, trifluoromethyl and methyl, and/or wherein $R^B$ is optionally substituted by two $R^{B1}$ groups, attached to the same carbon atom, that are joined to form a $C_{3-6}$ cycloalkyl or a 4-6-membered heterocyclyl ring; and $R^C$ and $R^D$ are each independently H, $C_{1-2}$ alkyl, hydroxy, methoxy or fluoro;

or a pharmaceutically acceptable salt and/or solvate thereof.

2. The compound or a pharmaceutically acceptable salt and/or solvate thereof according to claim 1 wherein $R^{A1}$ is halo.

3. The compound or a pharmaceutically acceptable salt and/or solvate thereof according to claim 1 wherein $R^{A2}$ is halo.

4. The compound or a pharmaceutically acceptable salt and/or solvate thereof according to claim 1 wherein m is 1.

5. The compound or a pharmaceutically acceptable salt and/or solvate thereof according to claim 1 wherein n is 1.

6. The compound or a pharmaceutically acceptable salt and/or solvate thereof according to claim 1 wherein p is 0.

7. The compound or a pharmaceutically acceptable salt and/or solvate thereof according to claim 1 wherein $R^B$ is $CH_2COOH$ optionally substituted on an available carbon atom by one or more $R^{B1}$; or wherein $R^B$ is $CH_2CH_2COOH$ optionally substituted on an available carbon atom by one or more $R^{B1}$.

8. The compound or a pharmaceutically acceptable salt and/or solvate thereof according to claim 1 wherein $R^B$ is not substituted.

9. The compound or a pharmaceutically acceptable salt and/or solvate thereof according to claim 1 wherein $R^B$ is substituted by one or more $R^{B1}$, wherein $R^{B1}$ is trifluoromethyl.

10. The compound or a pharmaceutically acceptable salt and/or solvate thereof according to claim 1, wherein $R^C$ is H and/or wherein $R^D$ is H.

11. The compound according to claim 1 which is selected from the list consisting of:

2-((4-((5-chloro-2,3-dihydro-1H-inden-2-yl)oxy)-2-methylene-4-oxobutanoyl)oxy)acetic acid;

2-((4-((4,6-dichloro-2,3-dihydro-1H-inden-1-yl)oxy)-2-methylene-4-oxobutanoyl)oxy)acetic acid (Enantiomer 1);

2-((4-((4,6-dichloro-2,3-dihydro-1H-inden-1-yl)oxy)-2-methylene-4-oxobutanoyl)oxy)acetic acid (Enantiomer 2);

2-((4-((5,6-dichloro-2,3-dihydro-1H-inden-2-yl)oxy)-2-methylene-4-oxobutanoyl)oxy)acetic acid;

2-((4-((5,6-dichloro-2,3-dihydro-1H-inden-1-yl)oxy)-2-methylene-4-oxobutanoyl)oxy)acetic acid (Enantiomer 1);

2-((4-((5,6-dichloro-2,3-dihydro-1H-inden-1-yl)oxy)-2-methylene-4-oxobutanoyl)oxy)acetic acid (Enantiomer 2);

2-((4-((5-chloro-2-methyl-2,3-dihydro-1H-inden-2-yl)oxy)-2-methylene-4-oxobutanoyl)oxy)acetic acid;

2-((4-((5,7-dichloro-2,3-dihydro-1H-inden-1-yl)oxy)-2-methylene-4-oxobutanoyl)oxy)acetic acid (Enantiomer 1);

2-((4-((5,7-dichloro-2,3-dihydro-1H-inden-1-yl)oxy)-2-methylene-4-oxobutanoyl)oxy)acetic acid (Enantiomer 2);

2-((4-((6,8-dichloro-1,2,3,4-tetrahydronaphthalen-2-yl)oxy)-2-methylene-4-oxobutanoyl)oxy)acetic acid (Enantiomer 1);

2-((4-((6,8-dichloro-1,2,3,4-tetrahydronaphthalen-2-yl)oxy)-2-methylene-4-oxobutanoyl)oxy)acetic acid (Enantiomer 2);

2-((4-((5-bromo-6-methoxy-2,3-dihydro-1H-inden-1-yl)oxy)-2-methylene-4-oxobutanoyl)oxy)acetic acid (Enantiomer 1);

2-((4-((5-bromo-6-methoxy-2,3-dihydro-1H-inden-1-yl)oxy)-2-methylene-4-oxobutanoyl)oxy)acetic acid (Enantiomer 2);

3-((4-((4,6-dichloro-2,3-dihydro-1H-inden-1-yl)oxy)-2-methylene-4-oxobutanoyl)oxy)propanoic acid (Enantiomer 1);

2-((4-((4-bromo-6-fluoro-2,3-dihydro-1H-inden-1-yl)oxy)-2-methylene-4-oxobutanoyl)oxy)acetic acid (Enantiomer 1);

2-((4-((4-bromo-6-fluoro-2,3-dihydro-1H-inden-1-yl)oxy)-2-methylene-4-oxobutanoyl)oxy)acetic acid (Enantiomer 2);

2-((2-methylene-4-oxo-4-((5-(trifluoromethyl)-2,3-dihydro-1H-inden-1-yl)oxy) butanoyl)oxy)acetic acid;

2-((2-methylene-4-oxo-4-((6-(trifluoromethoxy)-2,3-dihydro-1H-inden-1-yl)oxy)butanoyl)oxy)acetic acid;

2-((4-((4-chloro-6-fluoro-2,3-dihydro-1H-inden-1-yl)oxy)-2-methylene-4-oxobutanoyl)oxy)acetic acid (Enantiomer 1);

2-((4-((4-chloro-6-fluoro-2,3-dihydro-1H-inden-1-yl)oxy)-2-methylene-4-oxobutanoyl)oxy)acetic acid (Enantiomer 2);

2-((4-((5,6-dichloro-2-methyl-2,3-dihydro-1H-inden-2-yl)oxy)-2-methylene-4-oxobutanoyl)oxy)acetic acid;

(3R)-3-((4-((4,6-dichloro-2,3-dihydro-1H-inden-1-yl)oxy)-2-methylene-4-oxobutanoyl)oxy)-4,4,4-trifluorobutanoic acid (Diastereomer A);

(3S)-3-((4-((4,6-dichloro-2,3-dihydro-1H-inden-1-yl)oxy)-2-methylene-4-oxobutanoyl)oxy)-4,4,4-trifluorobutanoic acid (Diastereomer B);

2-((4-((5,7-dichloro-1,2,3,4-tetrahydronaphthalen-1-yl)oxy)-2-methylene-4-oxobutanoyl)oxy)acetic acid (Enantiomer 1);

2-((4-((5,7-dichloro-1,2,3,4-tetrahydronaphthalen-1-yl)oxy)-2-methylene-4-oxobutanoyl)oxy)acetic acid (Enantiomer 2);

2-((4-((5,6-difluoro-1,1,3,3-tetramethyl-2,3-dihydro-1H-inden-2-yl)oxy)-2-methylene-4-oxobutanoyl)oxy)acetic acid;

2-((2-methylene-4-oxo-4-((5-(trifluoromethyl)-2,3-dihydro-1H-inden-1-yl)oxy) butanoyl)oxy)acetic acid (Enantiomer 1);

2-((2-methylene-4-oxo-4-((6-(trifluoromethoxy)-2,3-dihydro-1H-inden-1-yl)oxy) butanoyl)oxy)acetic acid (Enantiomer 1);

2-((2-methylene-4-oxo-4-((5-(trifluoromethyl)-2,3-dihydro-1H-inden-1-yl)oxy) butanoyl)oxy)acetic acid (Enantiomer 2);

2-((2-methylene-4-oxo-4-((6-(trifluoromethoxy)-2,3-dihydro-1H-inden-1-yl)oxy) butanoyl)oxy)acetic acid (Enantiomer 2); and 2-((2-methylene-4-oxo-4-((6-(trifluoromethyl)-1,2,3,4-tetrahydronaphthalen-1-yl)oxy) butanoyl)oxy)acetic acid (Enantiomer 1);

or a pharmaceutically acceptable salt and/or solvate of any one thereof.

12. A pharmaceutical composition comprising a compound or a pharmaceutically acceptable salt and/or solvate thereof according to claim 1.

13. A compound selected from the group consisting of:

(a) a compound of formula (II):

(II)

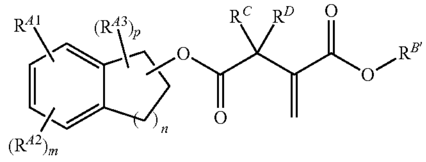

wherein $R^{A1}$, $R^{A2}$, $R^{A3}$, $R^C$, $R^D$, m, n and p are defined in claim 1 and $R^{B'}$ is a protected derivative of $R^B$;

or a salt thereof;

(b) a compound of formula (XI):

(XI)

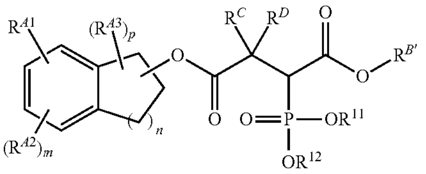

wherein $R^{A1}$, $R^{A2}$, $R^{A3}$, $R^C$, $R^D$, m, n and p are defined in claim 1, $R^{B'}$ is a protected derivative of $R^B$, and $R^{11}$ and $R^{12}$ are independently $C_{1-4}$ alkyl optionally substituted with halo;

or a salt thereof;

(c) a compound of formula (XII):

(XII)

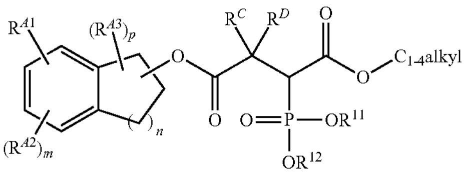

wherein $R^{A1}$, $R^{A2}$, $R^{A3}$, $R^C$, $R^D$, m, n and p are defined in claim 1, and $R^{11}$ and $R^{12}$ are independently $C_{1-4}$ alkyl optionally substituted with halo;

or a salt thereof; and (d) a compound of formula (XIV):

(XIV)

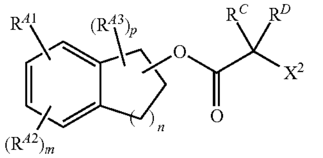

wherein $R^{A1}$, $R^{A2}$, $R^{A3}$, $R^C$, $R^D$, m, n and p are defined in claim 1, and $X^2$ is a leaving group;

or a salt thereof.

14. A compound of formula (XVI):

(XVI)

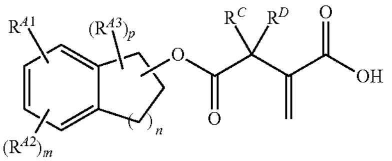

or a salt thereof;

wherein $R^{A1}$, $R^{A2}$, $R^{A3}$, $R^C$, $R^D$, m, n and p are defined in claim 1;

or a salt thereof.

15. A compound according to claim 14 selected from the group consisting of:

1-(2-(tert-butoxy)-2-oxoethyl) 4-(5-chloro-2,3-dihydro-1H-inden-2-yl) 2-methylenesuccinate;

1-(2-(tert-butoxy)-2-oxoethyl) 4-(4,6-dichloro-2,3-dihydro-1H-inden-1-yl) 2-methylenesuccinate (enantiomer 1);

1-(2-(tert-butoxy)-2-oxoethyl) 4-(4,6-dichloro-2,3-dihydro-1H-inden-1-yl) 2-methylenesuccinate (enantiomer 2);

1-(2-(tert-butoxy)-2-oxoethyl) 4-(5,6-dichloro-2,3-dihydro-1H-inden-2-yl) 2-methylenesuccinate;

4-(5,6-dichloro-2,3-dihydro-1H-inden-1-yl) 1-(2-oxo-2-(2,2,2-trichloroethoxy)ethyl) 2-methylenesuccinate (enantiomer 1);

4-(5,6-dichloro-2,3-dihydro-1H-inden-1-yl) 1-(2-oxo-2-(2,2,2-trichloroethoxy)ethyl) 2-methylenesuccinate (enantiomer 2);

4-(5-chloro-2-methyl-2,3-dihydro-1H-inden-2-yl) 1-(2-oxo-2-(2,2,2-trichloroethoxy)ethyl) 2-methylenesuccinate;

4-(5,7-dichloro-2,3-dihydro-1H-inden-1-yl) 1-(2-oxo-2-(2,2,2-trichloroethoxy)ethyl) 2-methylenesuccinate (enantiomer 1);

4-(5,7-dichloro-2,3-dihydro-1H-inden-1-yl) 1-(2-oxo-2-(2,2,2-trichloroethoxy)ethyl) 2-methylenesuccinate (enantiomer 2);

3-((3-oxo-3-(2,2,2-trichloroethoxy)propoxy)carbonyl) but-3-enoic acid;

3-((2,2,2-trichloroethoxy)carbonyl)but-3-enoic acid;

4-(4,6-dichloro-2,3-dihydro-1H-inden-1-yl) 1-(3-oxo-3-(2,2,2-trichloroethoxy)propyl) 2-methylenesuccinate; and 4-(4,6-dichloro-2,3-dihydro-1H-inden-1-yl) 1-((R)-1,1,1-trifluoro-4-oxo-4-(2,2,2-trichloroethoxy)butan-2-yl) 2-methylenesuccinate;

or a salt thereof.

* * * * *